US 8,597,395 B2
Dec. 3, 2013

(12) United States Patent
Goodwin

(10) Patent No.: US 8,597,395 B2
(45) Date of Patent: Dec. 3, 2013

(54) METHODS OF REDUCING PLANT ABIOTIC STRESS BY APPLYING A COMPOSITION COMPRISING LIGNINS, TANNINS, AND HYDROCARBONS

(75) Inventor: Brian B. Goodwin, Collierville, TN (US)

(73) Assignee: Floratine Biosciences, Inc., Collierville, TN (US)

( * ) Notice: Subject to any disclaimer, the term of this patent is extended or adjusted under 35 U.S.C. 154(b) by 239 days.

(21) Appl. No.: 12/892,564

(22) Filed: Sep. 28, 2010

(65) Prior Publication Data

US 2011/0078816 A1 Mar. 31, 2011

Related U.S. Application Data

(60) Provisional application No. 61/246,453, filed on Sep. 28, 2009.

(51) Int. Cl.
*A01N 25/02* (2006.01)
*A01N 27/00* (2006.01)
*A01N 65/00* (2009.01)
*C12Q 1/68* (2006.01)
*A01H 3/00* (2006.01)
*A01H 3/04* (2006.01)

(52) U.S. Cl.
USPC .......... 71/64.1; 71/64.01; 504/100; 536/23.1; 536/25.3; 530/500

(58) Field of Classification Search
None
See application file for complete search history.

(56) References Cited

U.S. PATENT DOCUMENTS

| | | | |
|---|---|---|---|
| 2,200,532 A | 12/1939 | Sherman | |
| 3,958,016 A | 5/1976 | Galle et al. | |
| 4,069,034 A | 1/1978 | Hoover | |
| 4,245,432 A | 1/1981 | Dannelly | |
| 4,249,343 A | 2/1981 | Dannelly | |
| 4,272,920 A | 6/1981 | Dawson | |
| 4,337,077 A | 6/1982 | Rutherford | |
| 4,367,609 A | 1/1983 | Lloyd | |
| 4,698,090 A | 10/1987 | Marihart | |
| 4,769,221 A | 9/1988 | Marihart | |
| 4,786,307 A | 11/1988 | Marihart | |
| 4,828,600 A | 5/1989 | McCabe et al. | |
| 4,875,921 A | 10/1989 | Paau | |
| 4,878,936 A | 11/1989 | Handelsman et al. | |
| 5,026,416 A | 6/1991 | Alexander | |
| 5,044,116 A | 9/1991 | Gago et al. | |
| 5,087,475 A | 2/1992 | Bazin et al. | |
| 5,129,180 A | 7/1992 | Stewart | |
| 5,178,661 A * | 1/1993 | van der Watt et al. ............ 71/24 |
| 5,204,368 A | 4/1993 | Cronje et al. | |
| 5,250,500 A | 10/1993 | Jones et al. | |
| 5,300,127 A | 4/1994 | Williams | |
| RE34,670 E | 7/1994 | Williams et al. | |
| 5,599,769 A | 2/1997 | Hacker et al. | |
| 5,665,671 A | 9/1997 | Zanin | |
| 5,747,020 A | 5/1998 | Rutherford et al. | |
| 5,849,320 A | 12/1998 | Turnblad et al. | |
| 5,928,997 A | 7/1999 | Bauer et al. | |
| 5,951,978 A | 9/1999 | Red'kina | |
| 6,022,744 A | 2/2000 | Tetteroo et al. | |
| 6,077,505 A | 6/2000 | Parke et al. | |
| 6,080,220 A | 6/2000 | Sequi et al. | |
| 6,080,319 A | 6/2000 | Alther | |
| 6,083,877 A | 7/2000 | Kinnersley et al. | |
| 6,090,750 A | 7/2000 | Chollet et al. | |
| 6,121,193 A | 9/2000 | Segaud et al. | |
| 6,199,318 B1 | 3/2001 | Stewart et al. | |
| 6,261,996 B1 | 7/2001 | Klittich et al. | |
| 6,277,787 B1 | 8/2001 | Malefyt et al. | |
| 6,372,008 B1 * | 4/2002 | Boote et al. ...................... 71/63 |
| 6,434,884 B1 | 8/2002 | Hartung | |
| 6,453,608 B1 | 9/2002 | Flanagan et al. | |
| 6,557,298 B2 | 5/2003 | Obert et al. | |
| 6,698,137 B2 | 3/2004 | Muhr | |
| 6,855,536 B2 | 2/2005 | Loh et al. | |
| 6,911,415 B1 | 6/2005 | Ueland et al. | |
| 7,001,869 B2 | 2/2006 | Johnson | |
| 7,003,914 B2 | 2/2006 | Legro et al. | |
| 7,182,951 B1 | 2/2007 | Balachander et al. | |
| 7,213,367 B2 | 5/2007 | Wertz et al. | |
| 7,393,678 B2 | 7/2008 | Triplett et al. | |
| 7,510,590 B2 | 3/2009 | Anaya-Olvera | |
| 7,687,434 B2 | 3/2010 | De Billot et al. | |
| 2002/0095864 A1 | 7/2002 | Obert et al. | |
| 2002/0134012 A1 | 9/2002 | Ding et al. | |
| 2003/0044382 A1 | 3/2003 | Selvig et al. | |
| 2003/0130120 A1 | 7/2003 | Ziemer et al. | |
| 2003/0228679 A1 | 12/2003 | Smith et al. | |

(Continued)

FOREIGN PATENT DOCUMENTS

| | | |
|---|---|---|
| CA | 1328238 | 4/1994 |
| CA | 2056107 | 7/1998 |

(Continued)

OTHER PUBLICATIONS

Schulze et al. Environment as stress factor: stress physiology of plants. Plant Ecology. Springer. 2005. pp. 7-11.*

(Continued)

*Primary Examiner* — Cathy Kingdon Worley
*Assistant Examiner* — Ashley K Buran
(74) *Attorney, Agent, or Firm* — Christopher J. Knors; Moore & Van Allen PLLC

(57) ABSTRACT

A method of regulating plant genes is provided. The method provides improved drought stress or salinity stress for plants. The method comprises treating a part of a plant or the locus thereof with a composition of matter, the composition of matter comprising an agriculturally acceptable mixture of compounds of natural organic material of defined composition.

21 Claims, 18 Drawing Sheets

(56) References Cited

U.S. PATENT DOCUMENTS

| | | | |
|---|---|---|---|
| 2003/0228981 A1 | 12/2003 | Wertz et al. | |
| 2004/0077498 A1 | 4/2004 | Lynch | |
| 2004/0118040 A1 | 6/2004 | Asrar et al. | |
| 2005/0197251 A1 | 9/2005 | Ding et al. | |
| 2005/0197253 A1 | 9/2005 | Stoller et al. | |
| 2006/0032120 A1 | 2/2006 | McPherson | |
| 2006/0032281 A1 | 2/2006 | Meyer | |
| 2006/0229203 A1 | 10/2006 | Peltonen et al. | |
| 2007/0039365 A1 | 2/2007 | King et al. | |
| 2007/0068072 A1 | 3/2007 | Xavier et al. | |
| 2007/0074451 A1 | 4/2007 | Pearce et al. | |
| 2007/0212772 A1 | 9/2007 | Hill et al. | |
| 2008/0004178 A1 | 1/2008 | Ding et al. | |
| 2008/0242544 A1 | 10/2008 | Duckham et al. | |
| 2008/0274885 A1 | 11/2008 | Martin et al. | |
| 2009/0105076 A1 | 4/2009 | Stewart et al. | |
| 2009/0105077 A1 | 4/2009 | Bhatti et al. | |
| 2010/0016162 A1 | 1/2010 | Goodwin | |
| 2011/0053771 A1 | 3/2011 | Goodwin | |
| 2011/0077155 A1 | 3/2011 | Goodwin | |
| 2012/0015805 A1* | 1/2012 | Goodwin | 504/100 |
| 2012/0196747 A1* | 8/2012 | Goodwin | 504/100 |
| 2013/0005570 A1* | 1/2013 | Goodwin | 504/101 |

FOREIGN PATENT DOCUMENTS

| | | | |
|---|---|---|---|
| EP | 164908 | 9/1989 | |
| EP | 560943 | 3/1999 | |
| EP | 949975 | 10/2002 | |
| EP | 1464635 A1 | 10/2004 | |
| EP | 1238714 | 3/2005 | |
| JP | 05-194951 | * 8/1993 | C09K 17/00 |
| WO | WO9013420 | 11/1990 | |
| WO | WO9015138 | 12/1990 | |
| WO | WO9210081 | 6/1992 | |
| WO | WO9517806 | 7/1995 | |
| WO | WO03020028 | 3/2003 | |
| WO | WO03020837 | 3/2003 | |
| WO | WO03094614 | 11/2003 | |
| WO | WO2007024753 | 3/2007 | |
| WO | WO2007143791 | 12/2007 | |
| WO | WO2009068195 | 6/2009 | |
| WO | WO2009068213 | 6/2009 | |

OTHER PUBLICATIONS

Jonak et al. Stress signaling in plants: a mitogen-activated protein kinase pathway is activated by cold and drought. PNAS. 1996. 93: 11274-11279.*

Wershaw, "Evaluation of Conceptual methods of natural matter (Humus) from a a consideration of the chemical and biochemical processes of Humification," 2004, US Dept. of the Interior, US geological survey; Scientific Investigations Report 2004-5121; pp. 5,6, and 11.*

Machine English translation of JP 05-194951 (1993).*

Johnson et al. Genetic control of plant growth. New Phytologist. 2001. 191: 319-333.*

Zhang. Influence of plant growth regulators on turgrass growth, antioxidant status, and drought tolerance. Dissertation. Virginia Polytechnic Institute and State University. 1997.*

Shandong Chuangxin Humic Acid Technology Co., Ltd. Humic Acid + Amino Acid Powder. http://www.humicacidcorp.com/. 2009. p. 1.*

Shandong Chuangxin Humic Acid Technology Co., Ltd. Nitro Humic Acid. http://www.humicacidcorp.com/. 2009. pp. 1-2.*

Korean Intellectual Property Office, PCT International Preliminary Report on Patentability and Written Opinion of the International Searching Authority for International Application No. PCT/US2010/050520, dated Apr. 3, 2012.

Korean Intellectual Property Office, PCT International Search Report and Written Opinion of the International Searching Authority for International Application No. PCT/US2010/050520, dated Jun. 22, 2011.

Wershaw, Robert L., "Evaluation of Conceptual Models of Natural Organic Matter (Humus) From a Consideration of the Chemical and Biochemical Processes of Humification", Scientific Investigations Report 2004-5121, US Department of the Interior, US Geological Survey (2004).

Pandey, Girdhar, et al., "ABR1, an APETALA2-Domain Transcription Factor that Functions as a Repressor of ABA Response in Arabidopsis", Plant Physiology, vol. 139, No. 3, pp. 1185-1193 (Nov. 2005).

http://ihss.gatech.edu/ihss2/whatarehs.html, What are Humic Substances? (Dec. 2007).

http://ihss.gatech.edu/ihss2/sources.html, Source Materials for IHSS Samples (Aug. 1, 2009).

Landec AG Inc.—Seeds of Innovation, IntelliCoat Early Plant Corn, Reference Guide.

Chinese Patent Office, Chinese Patent Application No. 2013070300854820 Office Action dated Jul. 8, 2013, pp. 1-8.

European Patent Office, European Patent Application No. 10819641.1 Extended European Search Report dated Jul. 8, 2013. pp. 1-6.

Collaberative, "Humus", Wikipedia, Internet Article, Jan. 1, 2002, URL: http://en.wikipedia.org/wiki/Humus, retreived on Jun. 24, 2013, p. 1.

Steinberg, et al., "Humic Substances, Part 2: Interactions with Organisms", Environ Sci Pollut Res Int (2008) 15(2), pp. 128-235.

* cited by examiner

CP  CONTROL

METHODS OF REDUCING PLANT ABIOTIC STRESS BY APPLYING A COMPOSITION COMPRISING LIGNINS, TANNINS, AND HYDROCARBONS

CROSS REFERENCE TO RELATED APPLICATION

This application claims the benefit of U.S. Provisional Patent Application No. 61/246,453 filed on Sep. 28, 2009, the contents of which are hereby incorporated by reference herein in its entirety.

TECHNICAL FIELD

The present invention relates to composition of matter for improving stress resistance in plants. Specifically, the method comprises contacting a part of a plant or the locus thereof with a composition of matter comprising an agriculturally acceptable complex mixture of dissolved organic material characterized by natural organic matter that is partially humified.

BACKGROUND

Various mixtures of organic compounds have been proposed in the art as fertilizer additives. Specifically, a humic acid composition, BIO-LIQUID COMPLEX™, is stated by Bio Ag Technologies International (1999) to assist in transferring micronutrients, more specifically cationic nutrients, from soil to plant.

TRIFLEX™ Bloom Formula nutrient composition of American Agritech is described as containing "phosphoric acid, potassium phosphate, magnesium sulfate, potassium sulfate, potassium silicate sodium silicate." TRIFLEX™ Grow Formula 2-4-1 nutrient composition of American Agritech is described as containing "potassium nitrate, magnesium nitrate, ammonium nitrate, potassium phosphate, potassium sulfate, magnesium sulfate, potassium silicate, and sodium silicate." Both compositions are said to be "fortified with selected vitamins, botanical tissue culture ingredients, essential amino acids, seaweed, humic acid, fulvic acid and carbohydrates." These products are said to be formulated primarily for "soilless hydrogardening" (i.e., hydroponic cultivation) of fruit and flower crops, but are also said to outperform conventional chemical fertilizers in container soil gardens. Their suitability or otherwise for foliar application as opposed to application to the hydroponic or soil growing medium is not mentioned.

The trademark MONARCH™, owned by Actagro, LLC is a fertilizer composition containing 2-20-15 primary plant nutrients with 3% non plant food organic compositions derived from natural organic materials.

Plants in general are susceptible to a variety of environmental stresses, including for example, drought, salinity, low light, water logging, disease, pests, and temperature. Conventional nutritional plant treatments are generally unable or incapable of providing plants with resistance to environmental stresses and are therefore are limited to providing benefit to otherwise healthy or flourishing plants. However, commercial agronomical processes require additional plant treatments to reduce plant stress or enhance the plants ability to resist common environmental stresses and/or to recover from such stresses quickly. Typical examples of common environmental stresses include continuous periods without water (drought), exposure to salt water, flooding, prolonged darkness, and temperature variations/frost. Exposure to such stresses generally can result in poor or no yields, but also can display reduced root growth, and/or reduced leaf growth or count, and/or reduced stalk weight and/strength, and/or reduced fruit size and/or weight and/or nutritional value. While a plant may possess some natural defenses to such stresses, there is a need to provide to plants enhanced abilities to respond and/or recover to such stresses to allow for maximizing agronomical production.

SUMMARY

Compositions of matter (hereafter also referred to as "CP"; CAS Reg. No.1175006-56-0) providing plants enhanced stress resistance abilities so as to respond and/or recover to environmental stresses and allow for maximizing agronomical production. The disclosed compositions of matter provide for gene regulation in plants that improve and/or enhance the plants responses to common environmental stresses. This gene regulation includes, among other mechanisms, regulation of transcription factors. Application of CP to a plant prior, during, or shortly thereafter a stress condition improves the plant's ability to resistant and/or recover argronomically from the stress as compared to a similarly situated plant not treated with CP.

Greenhouse and field experiments have demonstrated that CP can promote plant growth and development so as to increase crop yields. Physiological studies indicate that the composition of matter disclosed herein provides improved nutrient availability and mobility inside the plants. Additionally, CP augments synthesis or availability of plant hormones, and/or CP possesses synergetic actions with some of these plant hormones. At the molecular level, plant growth and development activities are controlled and/or influenced by genes and gene expression. It is likely that CP acts through triggering or altering the expression of critical genes involved in plant growth, development, stress tolerance, and/or disease resistance.

The potent effects of the above-mentioned compositions of matter on plant gene expression provides for wide application of these products in agriculture, horticulture, and landscaping.

DETAILED DESCRIPTION

Materials and Methods

Figure 1:
FIG. 1. Photograph representing the effect of a CP composition application on *Arabidopsis* root formation vs. control.

The composition of matter disclosed herein comprises a mixture of organic molecules isolated and extracted from sources rich in natural organic matter into an aqueous solution. The natural organic matter is primarily derived from plant materials that have been modified to varying degrees over time in a soil environment. Some of the plant materials have been recently deposited in the environment. At least a part of the natural organic matter has passed through a partial process of humification to become partially humified natural organic matter. Humification includes microbial, fungal, and/or environmental (heat, pressure, sunlight, lightning, fire, etc.) degradation and/or oxidation of natural organic matter. Most preferably, CP contains natural organic matter that has not substantially undergone humification (partially humified natural organic matter). In one aspect, the natural organic matter is obtained from environments typically containing or providing 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, or up to 500 ppm of dissolved organic matter (DOM). In other aspects, the natural organic matter is obtained from environments typically containing or providing about 500 ppm, 1000 ppm, 1500 ppm, 2000 ppm, 2500 ppm, 3000 ppm or more DOM.

Natural organic matter is extremely complex, with thousands of compounds generally present, depending upon the source and the environmental conditions prevalent about the source. Humic substances such as Fulvic Acid (CAS Reg. No. 479-66-3) and Humic Acid (CAS Reg. No. 1415-93-6) are examples of organic complexes that are derived from natural organic matter, however, CP is chemically and biologically unique from Fulvic and Humic acid, as detailed below.

CP contains dissolved organic matter, the organic matter being formed during the process of humification as described above, such as microbial, fungicidal, and/or environmental (heat, pressure, sunlight, lightning, fire, etc.) degradation processes. Other natural or synthetic natural organic matter degradation processes may be involved or may be used. In one aspect, CP contains predominately natural organic matter that has not undergone substantial humification (e.g., partially humified natural organic matter). The amount of humification may be determined and characterized using known methods, for example, by 13C NMR.

In one aspect, CP is obtained by removing a natural organic matter from its source, optionally processing, and/or concentrating to provide a CP composition having a dissolved organic matter (DOM) concentration level of about 10×, 25×, 50×, 100×, 200×, 300×, 400×, 500×, 600×, 700×, 800×, 900×, 1000×, 1500×, 2000×, 2500×, 3000×, 3500×, 4000×, 4500×, or 5000× relative to its original source. In another aspect, CP concentrations of dissolved organic matter (DOM) concentration level can be about 7500×, 10,000×, 15,000×, 20,000×, 25,000×, and up to 50,000×. CP compositions may be adjusted such that the concentration of DOM is between about 10 ppm to about 700,000 ppm. Preferably, CP may be adjusted such that the concentration of DOM is between about 1000 ppm to about 500,000 ppm. CP compositions may be adjusted to a DOM value represented by any ppm value between 1000 ppm and 50,000 ppm, inclusive of any ppm value in 500 ppm increments (e.g., 10,500 ppm, 11,000 ppm, 11,500 ppm, 12,000 ppm, etc.) in aqueous solution. Other DOM concentrations may be used, for example, an extremely concentrated composition of between about 75,000 ppm and about 750,000 ppm can be prepared. For example, a concentrate of about 30,000× that of the original source can contain about 550,000 ppm of DOM. In certain aspects, CP compositions are approximately between about 91% to about 99% water, the remaining organic material being primarily DOM with minor amounts of alkali-, alkali earth-, and transition metal salts. In yet other aspects, the DOM of the CP composition has been dried or lyophilized in a form suitable for reconstitution with an aqueous solution.

CP compositions contain a complex mixture of substances, typically a heterogeneous mixture of compounds for which no single structural formula will suffice. Detailed chemical and biological testing has shown that CP is a unique composition both in its biological effect on plants and its chemical composition compared to Humic and Fulvic acids. Elemental and spectroscopic characterization of CP material differentiates it from most other humic-based organic complexes, such as Humic and Fulvic Acids, as further discussed below. Blending of CP compositions may be performed to provide consistency of material and to compensate for the normal variations of a naturally-derived material.

CP compositions may be applied to the seed, foliage, or to any other part of the plant or its locus. Application rate of CP can be between about 0.01 gram/hectare to about 10.0 gram/hectare dry weight, between about 0.2 gram/hectare to about 2.0 gram/hectare dry weight, between 0.3 gram/hectare to about 1.5 gram/hectare dry weight, or between about 0.4 gram/hectare to about 1.0 gram/hectare dry weight applied in the soil or as a foliar application to the foliage or the locus of the plant.

Characterization Methods

The organic compounds making up CP can be characterized in a variety of ways (e.g., by molecular weight, distribution of carbon among different functional groups, relative elemental composition, amino acid content, carbohydrate content, etc.). In one aspect, CP was characterized relative to known standards of humic-based substances.

For purposes of characterizing carbon distribution among different functional groups, suitable techniques include, without limitation, 13C-NMR, elemental analysis, Fourier transform ion cyclotron resonance mass spectroscopy (FTICR-MS) and Fourier transform infrared spectroscopy (FTIR). The chemical characterization of CP and Humic substance standards were carried out using Electro spray Ionization Fourier Transform Ion Cyclotron Resonance Mass Spectroscopy (ESI-FTICR-MS), Fourier Transform Infrared Spectroscopy (FTIR) and elemental analysis for metals using ICP-AES, conducted by Huffman Laboratories, Inc. and the University of Washington.

Elemental, molecular weight, and spectroscopic characterization of CP is consistent with an organic complex that consists primarily of lignin and tannin compounds (and mixtures of condensed and un-condensed tannin), condensed aromatics and trace amounts of lipid and inorganics. Thousands of compounds are present, with molecular weights ranging from 225 to 700 daltons, the majority of compounds having between about 10 to about 39 carbon atoms per molecule. CP compositions are generally composed of carbon, oxygen, and hydrogen, with small amounts of nitrogen, and sulfur. CP compositions may also contain potassium and iron at levels above 5%.

The elemental composition of the dissolved solids typically present in CP compositions is given in Table A. If the organic compounds are separated from the inorganic elements, the elemental breakdown is: C 55%, H 4%, O 38%, N 1.8%, and S 2.2%.

TABLE A

Average Elemental Composition of dissolved solids, based upon average values from 10 different CP lots.

| Element | % |
| --- | --- |
| Carbon | 35.1 |
| Oxygen | 24.6 |
| Hydrogen | 2.5 |
| Sulfur | 2.1 |
| Nitrogen | 1.3 |
| Potassium | 27.3 |
| Iron | 6.1 |
| Calcium | 0.2 |
| Sodium | 0.2 |
| Phosphorous | 0.1 |
| Other | 0.5 |

Among the classes of organic compounds present in CP, analysis generally reveals that there are lignin and tannin (mixture of condensed and un-condensed), condensed aromatics, unidentified substances and some lipids present. In one aspect, the CP composition is characterized in that at least 10% of the total % compounds present in the CP composition is tannins and/or condensed tannins. In another aspect, the CP composition is characterized in that at least 15% of the total % compounds present in the CP composition is tannins and/or condensed tannins. In another aspect, the CP composition is characterized in that at least 20% of the total % compounds present in the CP composition is tannins and/or condensed tannins. Each of these classes of compounds is further characterized by a rather narrow Mw range and number of carbons/molecule. The breakdown of the number and percentage of each of the various compound classes, their MW's and carbon atoms/molecule (Carbon Range) for a representative sampling of CP is given in Table B1.

TABLE B1

Compound Classes in CP along with size and carbon ranges for compounds in each class. Based upon composite of 3 different production batches. Results for individual batches are very similar.

| Compound Class | # Compounds | % of Total | Size Range (daltons) | Carbon Range |
| --- | --- | --- | --- | --- |
| Lignin | 1139 | 57 | 226-700 | 11 to 39 |
| Tannin | 587 | 30 | 226-700 | 10 to 31 |
| Condensed Aromatic | 220 | 11 | 238-698 | 13 to 37 |
| Lipid | 18 | 1 | 226-480 | 14 to 30 |
| Carbohydrate | 1 | 0 | 653 | 24 |
| Other | 23 | 1 | 241-651 | 12 to 33 |

A breakdown of the number and percentage of each of the various compound classes, their MW's and carbon atoms/molecule (Carbon Range) for a second representative sampling based upon an average of 3 different production batches for the composition of matter is given in Table B2.

TABLE B2

Compound Classes in the composition of matter, along with size and carbon ranges for compounds in each class. Based upon average of 3 different CP production batches. Results for individual batches are very similar.

| Compound Class | #Compounds | % of Total | Size Range (daltons) | Carbon Range |
| --- | --- | --- | --- | --- |
| Lignin | 711 | 56 | 226-700 | 11 to 39 |
| Tannin | 410 | 33 | 226-700 | 10 to 31 |
| Condensed Aromatic | 122 | 10 | 238-698 | 13 to 37 |
| Lipid | 12 | ~1 | 226-480 | 14 to 30 |
| Carbohydrate | 1 | 0 | 653 | 24 |
| Other | 14 | ~1 | 241-651 | 12 to 33 |

Table C, summarizes the oxygen-to-carbon (O/C) and hydrogen-to-carbon (H/C) ratios used in defining the classes described above. In one aspect, the CP composition is characterized in that the O/C ratio of the dissolved organic matter is greater than about 0.4 as measured by mass spectroscopy. In one aspect, the CP composition is characterized in that the H/C ratio of the dissolved organic matter is greater than about 0.8 as measured by mass spectroscopy. In another aspect, the CP composition is characterized in that the H/C ratio of the dissolved organic matter is greater than about 0.85 as measured by mass spectroscopy.

TABLE C

Elemental Ratios and chemical classifications used in characterizing CP samples.

| Class | O/C | H/C | Aromaticity Index |
| --- | --- | --- | --- |
| Lignin | 0.15-0.6 | 0.6-1.7 | <0.7 |
| Tannin | 0.6-1.0 | 0.5-1.4 | <0.7 |
| Condensed Aromatic | 0.1-0.7 | 0.3-0.7 | >0.7 |
| Lipid | 0-0.2 | 1.8-2.2 | |
| Carbohydrate | 0.6-1.0 | 1.8-2.2 | |

Comparison of CP with Humic Substance Standards

Comparative elemental and structural characterization of Humic Substances verses CP was performed. Three humic substances standards from the International Humic Substances Society were used: Leonardite Humic Acid (LHA), Pahokee Peat Humic Acid (PPHA), and Suwannee River Fulvic Acid II (SRFA). Each humic substance standards and each CP sample was analyzed by FTIR and ESI-FTICR-MS. A portion of each humic substance standard was dissolved in NH₄OH/water for the ESI-FTICR-MS analysis. Three samples of CP (CP#60, CP#75, and CP#99) were prepared for analysis with cation exchange resin (AG MP-50, Bio-Rad Laboratories, Hercules, Calif.). Three samples of the composition of matter (CP#1,CP #2, and CP#3) were prepared for analysis with cation exchange resin (AG MP-50, Bio-Rad Laboratories, Hercules, Calif.). Comparison of the Humic Substance standards and each sample of the composition of matter is presented in Table D.

TABLE D

Comparison of humic substance standards and each CP sample.

| Sample | O/C | H/C | DBE | Avg. MW |
|---|---|---|---|---|
| Suwannee River Fulvic Acid (SRFA) | 0.39 | 1.01 | 12.7 | 445.7 |
| Pahokee Peat Humic Acid (PPHA) | 0.34 | 0.75 | 16.29 | 429.8 |
| Leonardite Humic Acid (LHA) | 0.3 | 0.79 | 15.8 | 423.6 |
| CP#60 | 0.54 | 0.87 | 13.7 | 472.9 |
| CP#75 | 0.54 | 0.89 | 13.23 | 456.9 |
| CP#99 | 0.5 | 0.91 | 13.23 | 455.7 |

Table D indicates that there are major differences between the Humic Substances standards and the CP samples. For example, the O/C ratio is less than 0.4 in all of the Humic Substances but is over 0.5 for the CP samples. The DBE for the CP samples is also significantly lower than for the Humic Acid Standards and the average MW is greater.

Based on mass spectral analysis, there are a number of compounds present in the CP samples that are substantially absent or greatly reduced in the Humic Substance standards. In particular, at least one component of CP may correspond with one or more tannin compounds. By comparison, in the Humic Substance standards, % tannin compounds are present in a small amount. For example, in the Fulvic Acid standard and in the Humic Acid standards, both standards are at least 3×-4× less than the % tannins found in the CP samples, as shown in Table E.

TABLE E

Number and % tannins in Humic Substance Standards verses CP.

| Sample | # tannins | % of tannin compounds |
|---|---|---|
| Suwannee River Fulvic Acid (SRFA) | 192 | 8.8 |
| Pahokee Peat Humic Acid (PPHA) | 9 | 1.2 |
| Leonardite Humic Acid (LHA) | 22 | 1.2 |
| CP#60 | 441 | 35.2 |
| CP#75 | 357 | 34.6 |
| CP#99 | 432 | 28.3 |

Comparing the Fourier Transform Infrared (FTIR) spectra for the IHSS standards and CP samples, there are similarities, primarily in the region from 1600 to 1800 cm$^{-1}$. In both sets of samples we see a very strong peak at around 1700 cm$^{-1}$ due to the C=O stretch from a carboxyl functional group and a peak in the 1590 to 1630 region which is consistent with a C=C bond from alkenes or aromatics. However, significant differences in the region from 700 to 1450 cm$^{-1}$ are observed. Peaks at 1160 to 1210 are present in all the spectra and are from the C—O bond of alcohols, ethers, esters and acids. The biggest difference is the peak at 870 cm$^{-1}$ in the CP samples, which is absent in the IHSS standards. This peak may be due to the C—H bond of alkenes and aromatics.

Based on the above chemical, elemental and structural characterization, CP is chemically and biologically unique from Humic and Fulvic acids or combinations thereof Further, as a result of the nature and extent of gene regulation and over all effect of CP with respect to improved plant health, drought and salinity stress resistance, CP is unique to that of known humic and/or fulvic acid compositions and treatments, for which such stress resistant activity and gene regulation properties are generally lacking in quality and quantity. Other beneficial plant function attributes of CP may be present or result from the methods of treatment and/or the gene regulation obtained from CP.

Based on the characterization data, the CP may contain relatively small molecules or supramolecular aggregates with a molecular weight distribution of about 300 to about 18,000 daltons. Included in the organic matter from which the mixture of organic molecules are fractionated are various humic substances, organic acids and microbial exudates. The mixture is shown to have both aliphatic and aromatic characteristics. Illustratively, the carbon distribution shows about 35% in carbonyl and carboxyl groups; about 30% in aromatic groups; about 18% in aliphatic groups, about 7% in acetal groups; and about 12% in other heteroaliphatic groups.

In some embodiments, the mixture of compounds in the CP comprises organic molecules or supramolecular aggregates with a molecular weight distribution of about 300 to about 30,000 daltons, for example, about 300 to about 25,000 daltons, about 300 to about 20,000 daltons, or about 300 to about 18,000 daltons.

Characterizing carbon distribution among different functional groups, suitable techniques can be used include without limitation 13C-NMR, elemental analysis, Fourier transform ion cyclotron resonance mass spectroscopy (FTICR-MS) and Fourier transform infrared spectroscopy (FTIR).

In one aspect, carboxy and carbonyl groups together account for about 25% to about 40%, for example about 30% to about 37%, illustratively about 35%, of carbon atoms in the mixture of organic compounds of the CP.

In another aspect, aromatic groups account for about 20% to about 45%, for example about 25% to about 40% or about 27% to about 35%, illustratively about 30%, of carbon atoms in the mixture of organic compounds of the CP.

In another aspect, aliphatic groups account for about 10% to about 30%, for example about 13% to about 26% or about 15% to about 22%, illustratively about 18%, of carbon atoms in the mixture of organic compounds of the CP.

In another aspect, acetal and other heteroaliphatic groups account for about 10% to about 30%, for example about 13% to about 26% or about 15% to about 22%, illustratively about 19%, of carbon atoms in the mixture of organic compounds of the CP.

In another aspect, the ratio of aromatic to aliphatic carbon is about 2:3 to about 4:1, for example about 1:1 to about 3:1 or about 3:2 to about 2:1 in the CP.

In a particular illustrative aspect, carbon distribution in the mixture of organic compounds of the CP is as follows: carboxy and carbonyl groups, about 35%; aromatic groups, about 30%; aliphatic groups, about 18%, acetal groups, about 7%; and other heteroaliphatic groups, about 12%.

Elemental composition of the organic compounds of the CP is independently in one series of embodiments as follows, by weight: C, about 28% to about 55%, illustratively about 38%; H, about 3% to about 5%, illustratively about 4%; 0, about 30% to about 50%, illustratively about 40%; N, about 0.2% to about 3%, illustratively about 1.5%; S, about 0.2% to about 4%, illustratively about 2%. Elemental composition of the organic compounds of the CP is independently in another series of embodiments as follows, by weight: C, about 45% to about 55%, illustratively about 50%; H, about 3% to about 5%, illustratively about 4%; O, about 40% to about 50%, illustratively about 45%; N, about 0.2% to about 1%, illustratively about 0.5%; S, about 0.2% to about 0.7%, illustratively about 0.4%.

In a particular illustrative aspect, elemental distribution is, by weight: C, about 38%; H, about 4%; O, about 40%; N, about 1.5%; and S, about 2%. The balance consists mainly of inorganic ions, principally potassium and iron in the CP. In another particular illustrative aspect, elemental distribution is, by weight: C, about 50%; H, about 4%; O, about 45%; N, about 0.5%; and S, about 0.4% in the CP.

Among classes of organic compounds that can be present in the CP are, in various aspects, amino acids, carbohydrates (monosaccharides, disaccharides and polysaccharides), sugar alcohols, carbonyl compounds, polyamines, lipids, and mixtures thereof These specific compounds typically are present in minor amounts, for example, less than 5% of the total % of compounds. Examples of amino acids that can be present include without limitation arginine, aspartic acid, glutamic acid, glycine, histidine, isoleucine, serine, threonine, tyrosine and valine. Examples of monosaccharide and disaccharide sugars that can be present include without limitation glucose, galactose, mannose, fructose, arabinose, ribose and xylose.

Based on the above chemical, elemental and structural characterization, the CP is chemically and biologically unique from Humic and Fulvic acids or combinations thereof Further, as a result of the nature and extent of gene regulation and over all effect of the CP with respect to improved plant health, drought and salinity stress resistance, it is generally believed that the CP is unique to that of known humic and/or fulvic acid compositions and treatments, for which such activity and properties are generally lacking in quality and quantity. Other beneficial plant function attributes of the CP may be present or result from the methods of treatment and/or the gene regulation obtained from the CP.

A suitable mixture of organic compounds can be found, for example, as one of many components in products marketed as CARBON BOOST™-S soil solution and KAFE™-F foliar solution of Floratine Biosciences, Inc. (FBS). Thus, exemplary compositions of aspects disclosed and described herein can be prepared by adding to CARBON BOOST™-S or KAFE™-F foliar solution as the CP, at least one pesticide as the second component, to a suitable volume of water. In one aspect, the active ingredient is CAS Reg. No. 1175006-56-0, and corresponds, by way of example, to CP.

The amount of the CP that should be present in the composition for providing stress resistance and/or gene regulation depends on the particular organic mixture used. The amount should not be so great as to result in a physically unstable composition, for example by exceeding the limit of solubility of the mixture in the composition, or by causing other essential components to fall out of solution. On the other hand, the amount should not be so little as to fail to provide enhanced stress resistance, or gene regulation when applied to a target plant species. For any particular organic mixture, one of skill in the art can, by routine formulation stability and bioefficacy testing, optimize the amount of organic mixture in the composition for any particular use.

Particularly where a mixture of organic compounds, as found, for example, in the commercially available formulations sold under the tradenames CARBON BOOST™-S and KAFE™-F, is used, the amount of the CP needed in a nutrition composition will often be found to be remarkably small. For example, as little as one part by weight (excluding water) of such a mixture can, in some circumstances, assist in foliar delivery of up to about 1000 or more parts by weight of the second component to a site of deposition in a plant. In other circumstances, it may be found beneficial to add a greater amount of the organic mixture, based on routine testing. Typically, a suitable ratio of the CP to the second component is about 1:2000 to about 1:5, for example about 1:1000 to about 1:10 or about 1:500 to about 1:20, illustratively about 1:100. If using CARBON BOOST™-S or KAFE™-F, solution as the source of organic compounds, a suitable amount of such solution to be included in a concentrate composition of second component herein is about 1 part by weight CARBON BOOST™-S or KAFE™-F, solution in about 5 to about 25, for example about 8 to about 18, illustratively about 12, parts by weight of the concentrate composition.

Optionally, additional components can be present in the composition of matter of the present invention. For example, the composition can further comprise as a second component. The second component can be of at least one agriculturally acceptable source of a plant nutrient other than CP. The second component can also be a pesticide, where the term "pesticide" herein refers to at least one herbicide, insecticide, fungicide, bactericide, anti-viral, nematocide, or a combination thereof Methods of use of the composition as described herein for plant and/or seed treating for reducing susceptibility to environmental stress of a plant are further disclosed. The composition can be applied to a single plant (e.g., a houseplant or garden ornamental) or to an assemblage of plants occupying an area. In some embodiments, the composition is applied to an agricultural or horticultural crop, more especially a food crop. A "food crop" herein means a crop grown primarily for human consumption. Methods of the present invention are appropriate both for field use and in protected cultivation, for example, greenhouse use.

While the present methods can be beneficial for gramineous (belonging to the grass family) crops such as cereal crops, including corn, wheat, barley, oats and rice, they are also highly appropriate for non-gramineous crops, including vegetable crops, fruit crops, broad-leaved field crops such as soybeans, seed crops or a crop of any species grown specially to produce seed. The terms "fruit" and "vegetable" herein are used in their agricultural or culinary sense, not in a strict botanical sense; for example, tomatoes, cucumbers and zucchini are considered vegetables for present purposes, although botanically speaking it is the fruit of these crops that is consumed.

Vegetable crops for which the present methods can be found useful include without limitation:

leafy and salad vegetables such as amaranth, beet greens, bitterleaf, bok choy, Brussels sprout, cabbage, catsear, celtuce, choukwee, Ceylon spinach, chicory, Chinese mallow, chrysanthemum leaf, corn salad, cress, dandelion, endive, epazote, fat hen, fiddlehead, fluted pumpkin, golden samphire, Good King Henry, ice plant, jambu, kai-lan, kale, komatsuna, kuka, Lagos bologi, land cress, lettuce, lizard's tail, melokhia, mizuna greens, mustard, Chinese cabbage, New Zealand spinach, orache, pea leaf, polk, radicchio, rocket (arugula), samphire, sea beet, seakale, Sierra Leone bologi, soko, sorrel, spinach, summer purslane, Swiss chard, tatsoi, turnip greens, watercress, water spinach, winter purslane and you choy;

flowering and fruiting vegetables such as acorn squash, Armenian cucumber, avocado, bell pepper, bitter melon, butternut squash, caigua, Cape gooseberry, cayenne pepper, chayote, chili pepper, cucumber, eggplant (aubergine), globe artichoke, luffa, Malabar gourd, parwal, pattypan squash, perennial cucumber, pumpkin, snake gourd, squash (marrow), sweetcorn, sweet pepper, tinda, tomato, tomatillo, winter melon, West Indian gherkin and zucchini (courgette);

podded vegetables (legumes) such as American groundnut, azuki bean, black bean, black-eyed pea, chickpea (garbanzo bean), drumstick, dolichos bean, fava bean (broad bean), French bean, guar, haricot bean, horse gram, Indian pea, kidney bean, lentil, lima bean, moth bean, mung bean, navy bean, okra, pea, peanut (groundnut), pigeon pea, pinto bean, rice bean, runner bean, soybean, tarwi, tepary bean, urad bean, velvet bean, winged bean and yardlong bean;

bulb and stem vegetables such as asparagus, cardoon, celeriac, celery, elephant garlic, fennel, garlic, kohlrabi, kurrat, leek, lotus root, nopal, onion, Prussian asparagus, shallot, Welsh onion and wild leek;

root and tuber vegetables, such as ahipa, arracacha, bamboo shoot, beetroot, black cumin, burdock, broadleaf arrowhead, camas, canna, carrot, cassava, Chinese artichoke, daikon, earthnut pea, elephant-foot yam, ensete, ginger, gobo, Hamburg parsley, horseradish, Jerusalem artichoke, jicama, parsnip, pignut, plectranthus, potato, prairie turnip, radish, rutabaga (swede), salsify, scorzonera, skirret, sweet potato, taro, ti, tigernut, turnip, ulluco, wasabi, water chestnut, yacon and yam; and herbs, such as angelica, anise, basil, bergamot, caraway, cardamom, chamomile, chives, cilantro, coriander, dill, fennel, ginseng, jasmine, lavender, lemon balm, lemon basil, lemongrass, marjoram, mint, oregano, parsley, poppy, saffron, sage, star anise, tarragon, thyme, turmeric and vanilla.

Fruit crops for which the present methods can be found useful include without limitation: apple, apricot, banana, blackberry, blackcurrant, blueberry, boysenberry, cantaloupe, cherry, citron, clementine, cranberry, damson, dragonfruit, fig, grape, grapefruit, greengage, gooseberry, guava, honeydew, jackfruit, key lime, kiwifruit, kumquat, lemon, lime, loganberry, longan, loquat, mandarin, mango, mangosteen, melon, muskmelon, orange, papaya, peach, pear, persimmon, pineapple, plantain, plum, pomelo, prickly pear, quince, raspberry, redcurrant, starfruit, strawberry, tangelo, tangerine, tayberry, ugli fruit and watermelon.

Seed crops for which the present methods can be found useful include without limitation: specialized crops used to produce seed of any plant species, for which the present methods can be found useful include, in addition to cereals (e.g., barley, corn (maize), millet, oats, rice, rye, sorghum (milo) and wheat), non-gramineous seed crops such as buckwheat, cotton, flaxseed (linseed), mustard, poppy, rapeseed (including canola), safflower, sesame and sunflower.

Other crops, not fitting any of the above categories, for which the present methods can be found useful include without limitation sugar beet, sugar cane, hops and tobacco.

Each of the crops listed above has its own particular stress protection needs. Further optimization of compositions described herein for particular crops can readily be undertaken by those of skill in the art, based on the present disclosure, without undue experimentation.

Methods of using the compositions disclosed and described herein comprise applying a composition as described herein to a seed, to a foliar surface of a plant, or to a locus of the plant or seed.

The term "agriculturally acceptable" applied to a material or composition herein means not unacceptably damaging or toxic to a plant or its environment, and not unsafe to the user or others that may be exposed to the material when used as described herein.

A "foliar surface" herein is typically a leaf surface, but other green parts of plants have surfaces that may permit absorption of active ingredient, including petioles, stipules, stems, bracts, flowerbuds, etc., and for present purposes "foliar surfaces" will be understood to include surfaces of such green parts.

A "locus" as used herein is inclusive of a foliar surface and also includes an area in proximity to a plant or the area in which a plurality of seed is or can be sown.

"Seed treatment" as used herein refers generally to contacting a seed with a compound or composition of matter containing or comprising at least one active ingredient (a.i. or AI). The compound or composition of matter may be in any form suitable to the seed, for example, liquid, gel, emulsion, suspension, dispersion, spray, or powder. Seed treatment is inclusive of seed coating and seed dressing. In a preferred embodiment, the A.I. is CP.

"Seed coating" or "seed dressing" as used herein refers generally to a coating or matrix formed on at least part of the seed, the coating or matrix containing or comprising the at least one AI. Optional compounds or agents may be included in the seed coating to facilitate the seed coating process or the disintegration/releasing of the at least one AI from the coating, or to prevent excessive dust-off or to add color to the treated seed.

The term "seed" as used herein, is not limited to any particular type of seed and can refer to seed from a single plant species, a mixture of seed from multiple plant species, or a seed blend from various strains within a plant species. The disclosed and described compositions can be utilized to treat gymnosperm seed, dicotyledonous angiosperm seed and monocotyledonous angiosperm seed.

The term "agronomical recovery" as used herein, is related to the relative resumption of biological response of the plant after the stress has been reduced or discontinued. Agronomical recovery is not limited to any particular type of biologically-related plant recovery and can include for example, recovery of some or all of weight, fruit production, yield, survival, color, appearance, fragrance, etc. In one example, agronomical recovery includes one or more of improved plant weight, number of leaves, and stalk weight after discontinuation of drought as compared to a similar plant not treated with the composition of matter disclosed herein.

Compositions disclosed and described herein can be applied using any conventional system for applying liquid or solid to a seed or foliar surface or locus. Most commonly, application by spraying will be found most convenient, but other techniques, including application by tumbling, brush or by rope-wick can be used if desired. For spraying, any conventional atomization method can be used to generate spray droplets, including hydraulic nozzles and rotating disk atomizers. Introduction of the composition into an irrigation system can be used.

For foliage surface or locus applications, the application rate of the composition can be between about 0.01 gram/hectare to about 10.0 gram/hectare dry weight, between about 0.2 gram/hectare to about 2.0 gram/hectare dry weight, between 0.3 gram/hectare to about 1.5 gram/hectare dry weight, or between about 0.4 gram/hectare to about 1.0 gram/hectare dry weight applied in the soil or as a foliar application to the foliage or the locus of the plant.

Compositions disclosed and described herein can be provided in concentrate form, (e.g., liquid, gel, or reconstitutable powder form), suitable for further dilution and/or mixing in water prior to application to the seed, plant, or locus. Alternatively, they can be provided as a ready-to-use solution for direct application. Because compositions disclosed and described herein can be combined with other fertilizer solutions and/or with pesticide solutions, they can be diluted and/or reconstituted by mixing with such other solutions.

The above concentrate compositions are suitable for further dilution. For application to plant foliage, a concentrate composition can be diluted up to about 600-fold or more with water, more typically up to about 100-fold or up to about 40-fold. Illustratively, a concentrate product can be applied at about 0.1 to about 30 l/ha, for example about 5 to about 25 l/ha, in a total application volume after dilution of about 60 to about 600 l/ha, for example about 80 to about 400 l/ha or about 100 to about 200 l/ha.

For seed treatment applications, a concentrate composition can be diluted up to about 600-fold or more with water, more typically up to about 100-fold or up to about 40-fold. Illustratively, a concentrate product can be applied at about 0.1 mg/Kg seed to about 100 mg/Kg seed, for example about 0.1 mg/Kg seed, 0.5 mg/Kg seed, 0.75 mg/Kg seed, 1.0 mg/Kg seed, 1.25 mg/Kg seed, 1.5 mg/Kg seed, 1.75 mg/Kg seed, 2.0 mg/Kg seed, 2.5 mg/Kg seed, 3.0 mg/Kg seed, 3.5 mg/Kg seed, 4.0 mg/Kg seed, 4.5 mg/Kg seed, 5.0 mg/Kg seed, 5.5 mg/Kg seed, 6.0 mg/Kg seed, 6.5 mg/Kg seed, 7.0 mg/Kg seed, 7.5 mg/Kg seed, 8.0 mg/Kg seed, 8.5 mg/Kg seed, 9.0 mg/Kg seed, 9.5 mg/Kg seed, and 10.0 mg/Kg seed. A concentrate product can also be applied at about 15 mg/Kg, 20 mg/Kg, 25 mg/Kg, and 30 mg/Kg.

Application solutions prepared by diluting concentrate compositions as described above represent further aspects of the compositions and methods disclosed and described herein.

Experimental

CP can affect plant gene expression and those genes that are up-regulated or down-regulated where identified, using the gene microarray technologies and the model plant *Arabidopisis*. In preliminary experiments on *Arabidopsis* conducted by Applicant, application of CP demonstrated an increased *Arabidopsis* leaf number by 24.9%, leaf area by 47.0%, leaf fresh weight by 46.9%, and leaf dry weight by 25% when the treated plants were exposed to salinity stress (NaCl). Similar application of CP delayed the appearance of wilting symptoms on *Arabidopsis* plants under drought stress. DNA analysis of *Arabidopsis thaliana* exposed to CP was performed to identify gene expression and regulation with correlation to aspects of various environmental stresses such as drought, oxidative stress, as well as correlation of gene expression and regulation to aspects of ion transport, and other functional mechanisms.

Plant material and growing conditions. *Arabidopsis thaliana*, accession Colombia (Col-0), was used. This accession was obtained from Dr. Z. Mou at the University of Florida's Department of Cell Sciences and Microbiology (Gainesville, Fla. 32611). Seeds were sown in autoclaved Metro-Mix 200 potting mix (SunGro Horticulture), watered with sterile distilled water, and vernalized in a cold room (dark at ~7° C.) for 3 days. Seeds were germinated and seedlings were grown in a growth room with room temperature set at 24° C. and relative humidity ranging from 45% to 70%. Initially the photoperiod in the growth room was 16 hours light and 8 hours dark, and later it was changed to 10 hours light and 14 hours dark.

CP vs Control Experiments. For foliar application, CP and comparative example CE, were diluted with deionized water, and sprayed onto *Arabidopsis* rosette leaves until run-off. To incorporate CP into tissue culture medium, CP stock solution was filter-sterilized under an aseptic hood and added to the medium that was autoclaved and cooled to about 45° C.

Salinity (salt) stress. This was induced by applying sodium chloride solution (50 mM to 200 mM) to the growing or culture medium.

Drought stress. Growing medium was allowed to dry out gradually in the growth room without watering.

Plant growth assay. This was done by counting rosette leaves. At the end of the experiment, leaves were harvested, and their leaf areas were determined using a large flat-bed scanner (Epson Expression 10000XL) and the Winfolia software (Regenet Instrument Inc.). Leaf fresh weights were taken right after harvesting, and dry weights were taken after 24 to 48 hours of drying at 175° C.

Gene Regulation Study

Microarray analysis indicated that CP compositions are quite potent in regulating the expression of a large and diverse group of *Arabidopsis* genes. Six hours after foliar application of CP (hereinafter also referred to as "T1") and a second CP formulation, designated CP1000 (hereafter also referred to as "T2"), the expression level of 456 genes changed greater than 50% (1.5 fold). Among them, 60 genes increased expression by 1.5 to 3.2 fold, and 396 genes decreased expression level by 1.5 to 38.4 fold. Six hours after foliar application of comparative example CE, the expression level of 423 genes changed by greater than 50% (1.5 fold), among which, 160 genes increased their expression by 1.5 to 4.0 fold and 263 genes decreased expression by 1.5 to 20.3 fold. The chemical compositions of CP and CP1000 (T1 and T2) share the characteristics of the partially humified material described herein.

Some of the genes regulated by CP may be involved in the responses to or metabolism of, plant hormones, such as auxins, gibberellic acid, abscisic acid, etc., and potentially other chemical stimuli. Some other genes are likely involved in ion binding or mobility, plant defense, etc. Most remarkably, many of the genes regulated by CP are transcription factors.

The above results indicate that CP is able to exert significant effects on numerous plant biochemical and physiological processes important for plant growth, development, and stress tolerance. In some sense, CP acts like a nontraditional plant growth regulator.

Although this study was the first attempt to understand the modulating roles of CP on plant gene expression, the results demonstrate some very intriguing phenomenon regarding the mode of action of CP. Nevertheless, further investigations are ongoing to validate the findings from this study and to better understand the effects of CP on global gene expression and particularly, on key genes involved in critical plant physiological or biochemical processes.

Microarray Preparation

Total RNA was isolated from rosette leaves using the RNease Plant Mini Kit reagent (Qiagen Sciences, Mass.) and dissolved in RNase-free water (Fisher Scientific). Microarray preparation and scanning services were provided by the University of Florida's Interdisciplinary Center for Biotechnology Center (UF-ICBR, Gainesville, Fla.). RNA concentration was initially determined using the Nandrop 8000, and then examined by Agilent 2100 Bioanalyzer. Fluorescently labeled cRNAs were generated from 175 ng of total RNA in each reaction using the Agilent Technologies Quick Amp Labeling Kit/Two Color (Agilent p/n 5190-0444). Cy5-labeled cRNA from a specific treatment was mixed with the same amount of Cy3-labeled cRNA from the control, or vice versa in dye-swap. Hybridization was performed according to Agilent Technologies's hybridization user's manual and Gene Expression Hybridization Kit (Agilent p/n 5 188-5242). A total of 100 ul of reaction mix was applied to the each Agilent Technologies 44K *Arabidopsis* 4 microarray (43803 features) and hybridized in a hybridization rotation oven at 65° C. for 17 hours. The slides were washed first with Gene Expression Wash Buffer 1 (Agilent p/n 5 188-5325)/0.005% Triton X-102 for 1 minute at room temperature and then with Gene Expression Wash Buffer 2 (Agilent p/n 5188-5326)/0.005% Triton X-102 for 1 minute at room temperature, and dried by immerging the slides into Agilent Stabilization and Drying Solution (Agilent p/n 5185-5979) for 30 seconds. The arrays were scanned by using a dual-laser DNA microarray scanner (model G2505C, Agilent Technologies). The data were extracted from images and normalized within the arrays using Feature Extraction 10.1.1.1 software (Agilent Technologies). The within array normalization was based on Lowess method.

Microarray Data Analysis

The GeneSpring GX 10.0.2 package (Agilent Technologies) was used to analyze the microarray data. The two color data (red and green) were imported into GeneSpring as single color data (red or green) using split-channel During this process, between-array normalization was performed using percentile shift and shift to median of all samples.

Lists of differentially expressed genes were identified first according to t-test p values ($\leq 0.01$), then the fold change ($\geq 1.5$). Additionally, the R2.3 software and the LIMMA package were used to normalize the microarray data and generate lists of differentially expressed genes.

Results

1. Effect of CP on *Arabidopsis* growth under normal growing conditions: Tests were conducted to determine the effect of CP on normal growing conditions of *Arabidopsis* plants. These tests indicated that treated *Arabidopsis* plants appeared to have denser roots on root balls than non-treated plants (FIG. 1), but no significant differences were observed between treated and non-treated plants in leaf number, leaf area, and fresh or dry leaf weight (Table 1).

Figure 2:
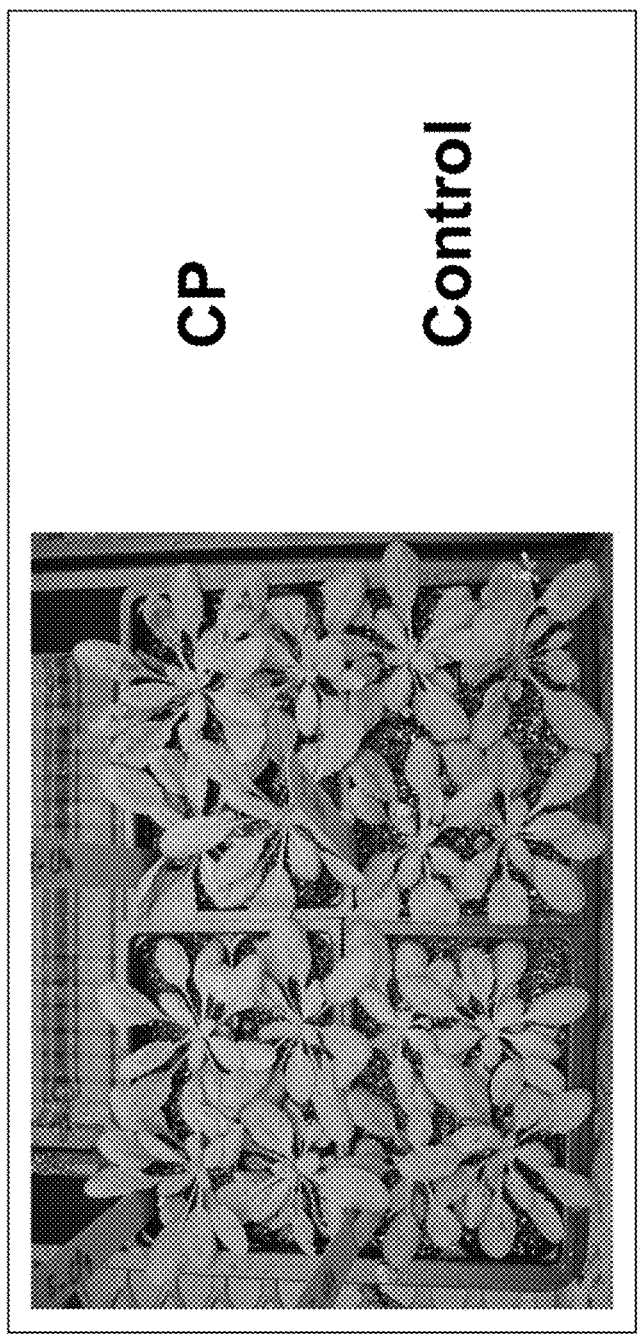
FIG. 2. Photograph representing the effect of a CP composition application on *Arabidopsis* growth vs. control under normal conditions.
Figure 14:
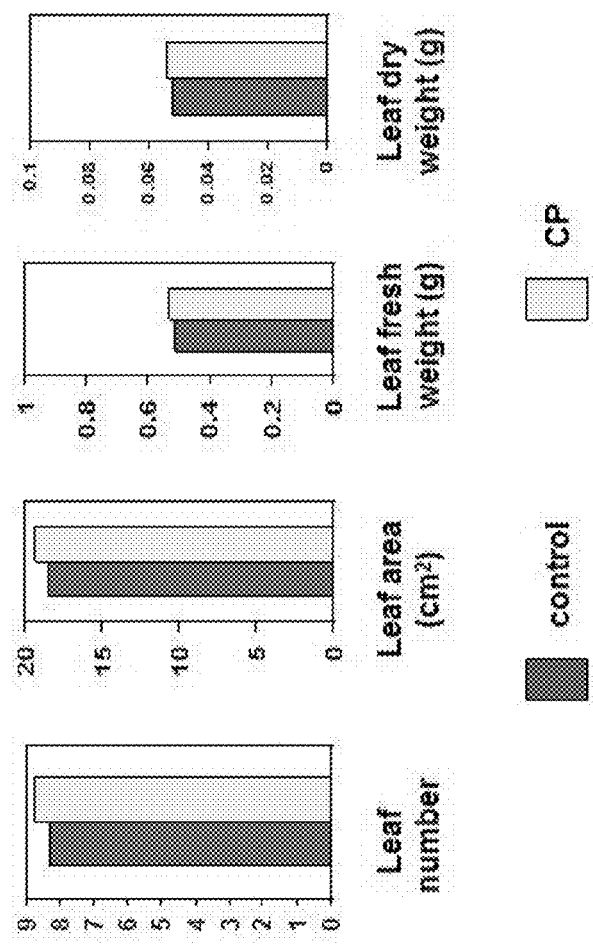
FIG. 14. Graph of the effect of a CP composition application on *Arabidopsis* drought tolerance vs. control.

The test was repeated under a different photoperiod (10/14 hours day/night). No significant differences were observed between control CP, (and comparative example CE) treated plants in leaf number (7, 14, and 21 days post treatment), leaf area, and fresh or dry leaf weight (Table 2; FIG. 2; FIG. 14).

TABLE 1

Effect of CP application on *Arabidopsis* growth

| Treatment | Replicates | Plants in replicate (subsamples) | Leaf number | Leaf fresh weight (g) | Leaf area (cm$^2$) | Leaf dry weight (g) |
|---|---|---|---|---|---|---|
| Control | 1 | 8 | 8.5 | 0.540 | 18.766 | 0.053 |
|  | 2 | 8 | 8.1 | 0.470 | 18.113 | 0.050 |
|  | 3 | 8 | 8.0 | 0.523 | 18.134 | 0.053 |
|  | 4 | 8 | 8.5 | 0.493 | 19.075 | 0.055 |
|  | Average |  | 8.3 | 0.506 | 18.522 | 0.052 |
| CP | 1 | 8 | 8.8 | 0.439 | 17.726 | 0.052 |
|  | 2 | 8 | 8.6 | 0.515 | 19.076 | 0.050 |
|  | 3 | 8 | 9.4 | 0.575 | 21.693 | 0.061 |
|  | 4 | 8 | 8.6 | 0.577 | 18.830 | 0.054 |
| CP | Average |  | 8.8 | 0.526 | 19.331 | 0.054 |

TABLE 2

Effect of CP application on *Arabidopsis* growth (10/14 hours day/night)

| Treatment | Replicate | No. plants | Leaves per plant (average over 8plants) 7 days | 14 days | 21 days | Leaf area (cm$^2$) | Fresh weight (g) | Dry weight (g) |
|---|---|---|---|---|---|---|---|---|
| Control | 1 | 8 | 5.9 | 11.7 | 14.6 | 31.52 | 0.65 | 0.05 |
|  | 2 | 8 | 6.3 | 11.4 | 16.1 | 28.70 | 0.59 | 0.05 |
|  | 3 | 8 | 5.8 | 11.8 | 16.4 | 29.82 | 0.63 | 0.05 |
|  | 4 | 8 | 5.8 | 10.8 | 15.6 | 26.16 | 0.48 | 0.04 |
|  | Average |  | 5.9 | 11.4 | 15.7 | 29.05 | 0.59 | 0.05 |
| CP | 1 | 8 | 5.4 | 11.0 | 15.3 | 28.14 | 0.58 | 0.05 |
|  | 2 | 8 | 5.6 | 10.8 | 15.3 | 25.03 | 0.48 | 0.04 |
|  | 3 | 8 | 5.8 | 11.2 | 15.6 | 28.35 | 0.57 | 0.05 |
|  | 4 | 8 | 6.0 | 11.4 | 15.8 | 33.53 | 0.57 | 0.05 |
|  | Average |  | 5.7 | 11.1 | 15.5 | 28.76 | 0.55 | 0.05 |

Figure 3:
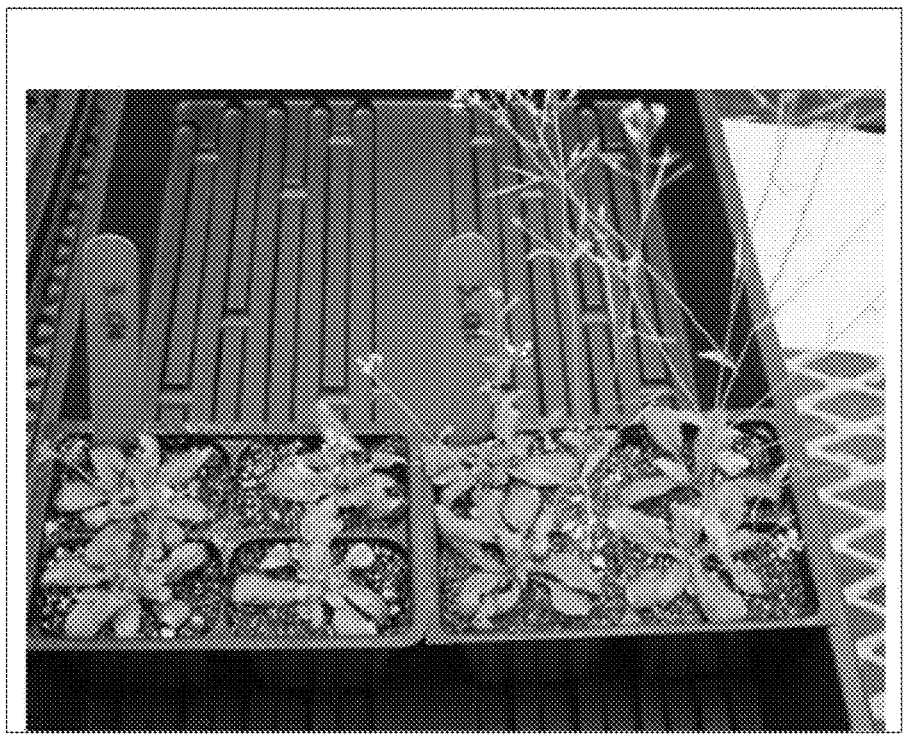
FIG. 3. Photograph representing the effect of a CP composition application after salinity stress on *Arabidopsis* growth and development vs. control.

2. Effect of CP on salt stress tolerance: Two tests were conducted on *Arabidopsis* plants to determine the effectiveness of CP on reducing salt stress. In the first one, plants were stressed by irrigating with 100 mM NaCl 4 days before CP application. Each pot (cell) with one plant received 25 mL of 100 mM NaCl on 3 and 5 Feb. 2009. One day later plants were treated with CP or water (control). Seventy-four percent of the treated plants developed multiple shoots (FIG. 3), whereas only 29% of the non-treated plants developed multiple shoots (Table 3).

TABLE 3

Effect of Post-CP Application on NaCl-stressed Arabidopsis.

| Treatment | Replicate | Total no. plants treated | No. plants with multiple shoots | % plants with multiple shoots |
|---|---|---|---|---|
| Control | 1 | 7 | 1 | 14 |
| | 2 | 8 | 2 | 25 |
| | 3 | 8 | 3 | 38 |
| | 4 | 8 | 3 | 38 |
| | Average | | | 29 |
| CP | 1 | 8 | 5 | 63 |
| | 2 | 7 | 4 | 57 |
| | 3 | 8 | 6 | 75 |
| | 4 | 8 | 8 | 100 |
| | Average | | | 74 |

Figure 4:
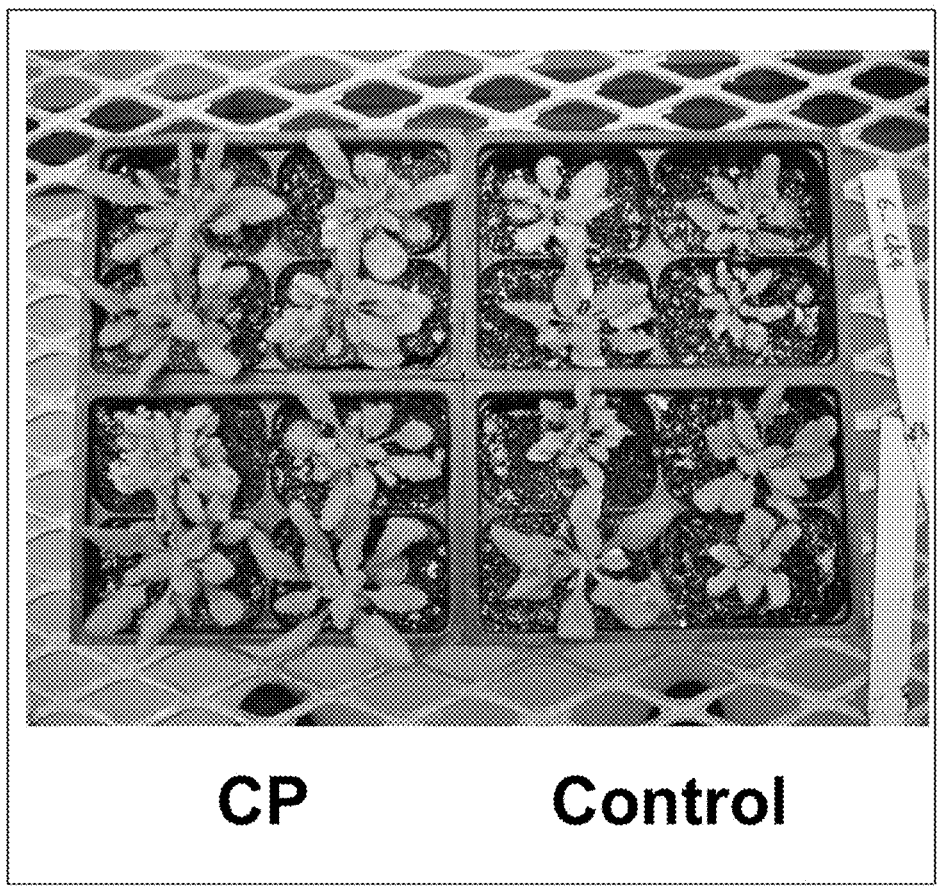
FIG. 4. Photograph representing the effect of a CP composition application before salinity stress on *Arabidopsis* growth vs. control.
Figure 15:
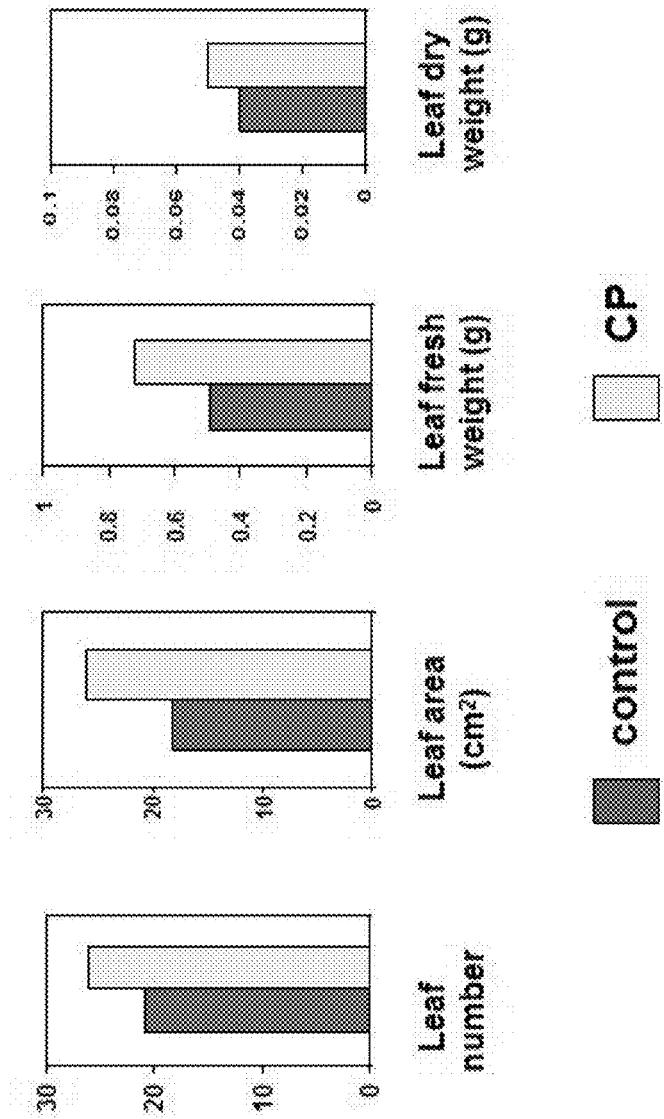
FIG. 15. Graph of the effect of a CP composition application on *Arabidopsis* salinity tolerance vs. control.

In the second test, *Arabidopsis* plants were treated with CP before they were subjected to salt stress. Different results were obtained. Plants were foliar-sprayed with CP or water on 16 Feb. 2009, and irrigated with 50 mM NaCl 4 days and then 100 mM NaCl 7 days post CP application. In this test, the CP treatment significantly increased leaf number (24.9%), area (47.0%), and fresh weight (46.9%) and dry weight (25.0%) (Table 4; FIG. 4; FIG. 15).

TABLE 4

Effects of Pre-CP application on Arabidopsis growth and development under salt stress.

| | Leaves (no.) | Leaf area (cm2) | Fresh weight (g) | Dry weight (g) |
|---|---|---|---|---|
| Control | 20.9 | 18.1 | 0.49 | 0.04 |
| CP | 26.1 | 26.6 | 0.72 | 0.05 |
| Change | Up 24.9% | Up 47.0% | 46.9% | 25.0% |
| P-value | 0.014 | 0.0013 | 0.0060 | <0.01 |

Additional salt stress experiment were conducted, the purpose of which was to determine the effect of CP in mitigating the impact of induced salt stress on tomato plants (*Lycopersicon* es.) grown in a greenhouse. The tomatoes were produced from seed and transplanted into 3 inch by 3 inch pots for this experiment. There were five treatments in total with 8 replicates per treatment arranged in a Randomized Complete Block design. All pots received an application of CP as a 25 ml soil drench on the day they were transplanted and a second application 14 days later. The untreated check was treated with only water, and the pots treated with CP had rates that ranged from 0.3 ppm CP to 2.4 ppm CP. Seven days after the second application, half of the pots in each treatment received a 25 ml soil drench of 200 mM NaCl salt solution. Eleven days later, the plants were measured for vigor, plant height, number of leaves, and plant, root, and shoot weights. Data are shown in Tables 4A and 4B.

TABLE 4A

Plant weights eleven days after salt stress. Means followed by the same letter do not significantly differ (P = .010, Duncan's New MRT).

| | Root Weight (g) | | Shoot Weight (g) | | Plant Weight (g) | |
|---|---|---|---|---|---|---|
| Treatment | Salt | No Salt | Salt | No Salt | Salt | No Salt |
| UTC | 11.3c | 14.4a | 17.5a | 19.4a | 28.8cd | 33.8b |
| 2.4 ppm CP | 7.5d | 7.5c | 16.9a | 20.0a | 24.4d | 27.5c |
| 1.2 ppm CP | 11.3c | 8.8 | 18.1a | 20.0a | 29.4c | 28.8c |
| 0.6 ppm CP | 21.3b | 26.9a | 18.1a | 21.9a | 39.4b | 48.8a |
| 0.3 ppm CP | 32.5a | 25.0a | 21.3a | 21.9a | 53.8a | 46.9a |

TABLE 4B

Plant vigor after salt stress. Vigor Ratings: 5 = best, 0 = dead.
Means followed by the same letter do not significantly differ (P = .010, Duncan's New MRT).

| | Plant Vigor | | Plant Height (inches) | | Number of Leaves per Plant | |
|---|---|---|---|---|---|---|
| Treatment | Salt | No Salt | Salt | No Salt | Salt | No Salt |
| UTC | 3.0a | 2.9a | 9.1a | 9.1a | 5.8a | 6.4a |
| 2.4 ppm CP | 3.1a | 2.9a | 8.9a | 9.1a | 5.3a | 5.8a |
| 1.2 ppm CP | 2.9a | 3.0a | 9.2a | 8.9a | 5.6a | 6.3a |
| 0.6 ppm CP | 3.0a | 3.0a | 8.6a | 9.3a | 5.6a | 6.6a |
| 0.3 ppm CP | 3.1a | 3.1a | 9.0a | 8.8a | 6.3a | 6.3a |

This experiment was designed, at least in part, to evaluate the optimum rate of CP for mitigating stress. As is clearly shown above, the salt drench had a negligible effect on plant shoots as shown by the vigor, height, leaf number and shoot weight. However, the salt had a statistically significant negative impact on root weight and overall plant weight for plants in the UTC when compared to the plants in the UTC without salt stress. The addition of high rates of CP (1.2 and 2.4 ppm of CP) caused significant root pruning for both the salt stressed plants and the unstressed plants, but low rates significantly improved root and overall plant size for both the stressed and unstressed plants. For plants treated with the lowest rate of CP, there was no statistical difference in the root weights between the unstressed and stressed plants. The results shown in Tables 4A and 4B were not predicted.

An additional experiment was performed, the purpose of this experiment was to determine the effect of CP in mitigating the impact of induced salt stress on tomato plants (*Lycopersicon* es.) grown in a greenhouse. The tomatoes were produced from seed and transplanted into 3 inch by 3 inch pots for this experiment. There were five treatments in total with 8 replicates per treatment arranged in a Randomized Complete Block design. All pots received an application of CP as a 25 ml soil drench on the day they were transplanted and a second application 14 days later. The untreated check was treated with only water, and the pots treated with CP had rates of 0.075 and 0.0375 ppm CP. Seven days after the second application, half of the pots in each treatment received a 25 ml soil drench of 200 mM NaCl salt solution. Thirteen days later, the plants were measured for number of leaves and shoot weights. Data are shown in Tables 4C and 4D.

TABLE 4C

Plant shoot weight 13 days after salt stress. Means
followed by the same letter do not significantly differ
(P = .010, Duncan's New MRT).

| Treatment | Shoot weight |
|---|---|
| UTC | 29.6d |
| 0.3 ppm CP | 34.3bcd |
| 1.5 ppm CP | 35.6c |
| 0.075 ppm CP + 200 mM NaCl | 41.5a |
| 0.0375 ppm CP + 200 mM NaCl | 35.3bc |

TABLE 4D

Plant leaf count 13 days after salt stress. Means
followed by the same letter do not significantly differ
(P = .010, Duncan's New MRT).

| Treatment | # of Leaves |
|---|---|
| UTC | 6.6c |
| 0.3 ppm CP | 7.6ab |
| 1.5 ppm CP | 7.3bc |
| 0.075 ppm CP + 200 mM NaCl | 8ab |
| 0.0375 ppm CP + 200 mM NaCl | 8.4a |

This experiment was designed, at least in part, to evaluate two different application rates of CP on plant development and for mitigating stress. As is shown above, plants treated with CP at both rates showed a statistically significant difference in both the shoot weights and the number of leaves, regardless of whether they were exposed to salt induced stress. Further, it is shown that the plants receiving applications of CP and salt were as large or larger than those treated with CP without salt stress, and these plants also had more leaves. Normally, salt applied at these levels would be expected to reduce both size and the number of leaves on a plant. Therefore, the results shown in Tables 4C and 4D were not predicted.

Figure 5:
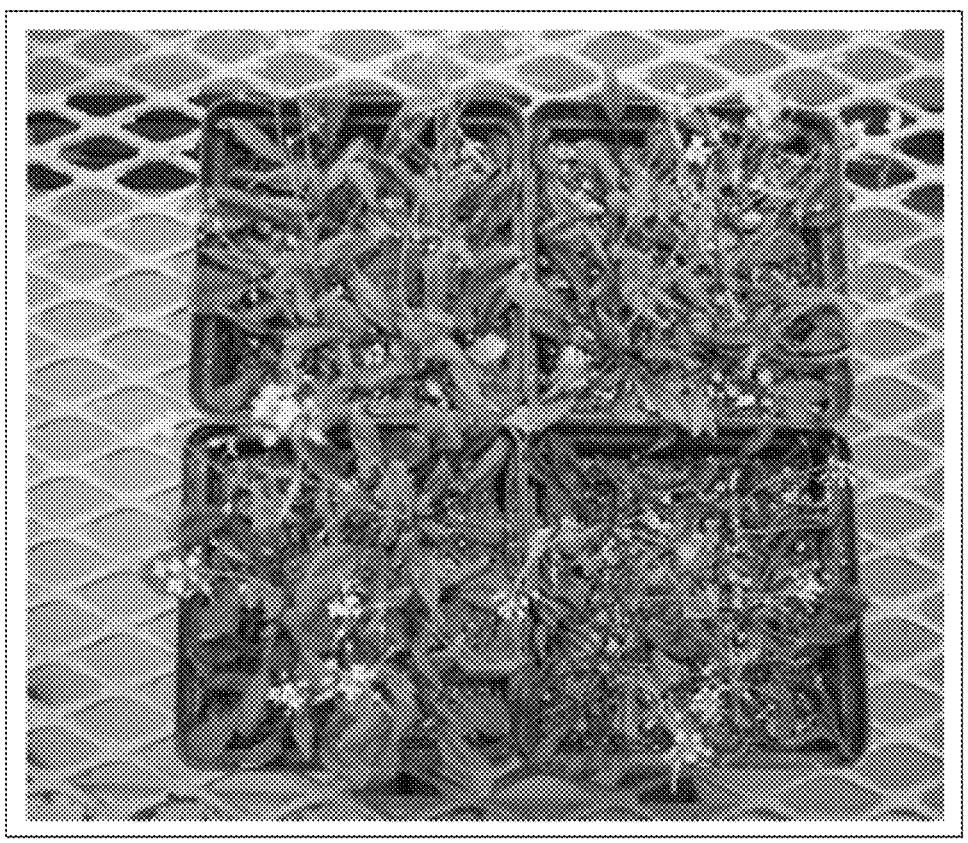
FIG. 5. Photograph representing the effect of a CP composition application on *Arabidopsis* drought tolerance vs. control.
Figure 16:
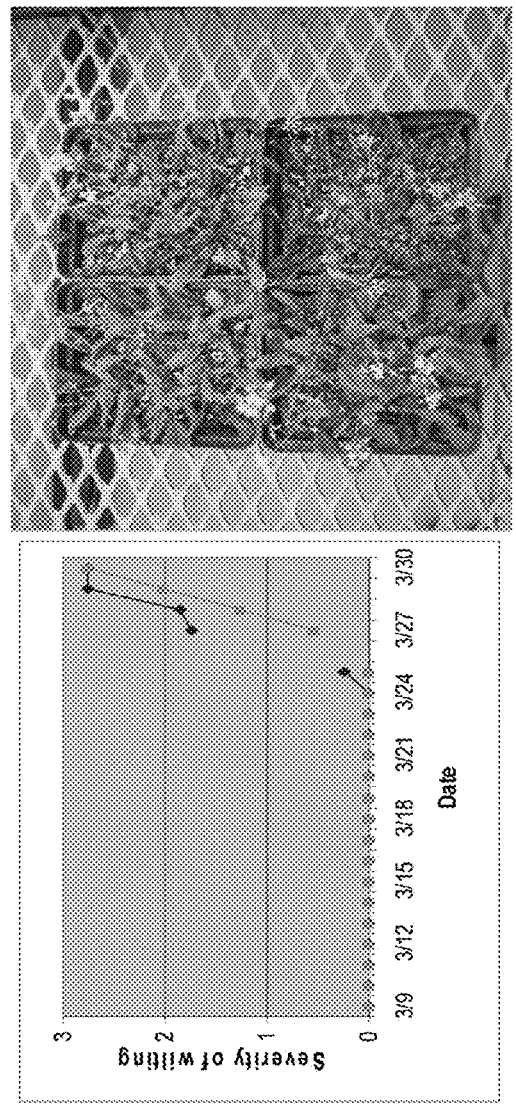
FIG. 16. Graph and photo of the effect of a CP composition application on *Arabidopsis* wilting drought tolerance vs. control.

3. Effect of CP on drought tolerance: *Arabidopsis* plants were treated with or without CP on 23 Feb. 2009, and then subjected to the drought condition by discontinuing watering from 9 Mar. 2009 on. These plants were observed from 9 March to 30 March for wilting symptom or plant death. This CP treatment seemed to delay wilting symptoms 1 to 2 days (FIG. 5; FIG. 16). FIGS. 5 and 16 show the effect of CP application on *Arabidopsis* tolerance to drought. As see in FIG. 5, Left column: CP treated; right column: control. Photo taken 17 days after watering was stopped.

Additional experiments were conducted, the purpose of which was to determine the effect of CP in mitigating the impact of induced drought stress on tomato plants (*Lycopersicon* es.) grown in a greenhouse. The tomatoes were produced from seed and transplanted into 3 inch by 3 inch pots for this experiment. There were three treatments in total with 8 replicates per treatment arranged in a Randomized Complete Block design. All pots in Treatment 2 received an application of CP as a 25 ml soil drench on the day they were transplanted and a second application 21 days later. The untreated check and Treatment 3 were treated with water only. Seven days after the second application, daily watering was discontinued for all plants in Treatments 2 and 3 to simulate extreme drought conditions. At sixteen days after watering was halted, half of the plants in each treatment were harvested to measure root weight, shoot weight, and total weight. Watering was then resumed and the recovery from the drought stress was determined nine days later. The results are shown in Table 4E. As shown, all plants that were not watered for a period of time were eventually impacted whether they were treated with CP or not. The CP appears to have a slight effect in minimizing the impact of no water, but the data may not be statistically significant. However, after watering was resumed, the plants treated with CP had a much improved response/recovery with regard to root and shoot weights as shown Table 4D. This response data was determined to be statistically significant. Thus, the composition of matter disclosed herein provides for an improvement in stress reduction that also includes improved "agronomical recovery" of the plant after the stress is reduced and/or discontinued compared to similar plants not treated with the composition of matter. The autorecovery results shown in Table 4E were not predicted.

TABLE 4E

Tomato plant weights sixteen days after watering halted and nine days after resuming watering. Means followed by same letter for root weight, or shoot weight, or total plant weight do not significantly differ (P = 0.10, Duncan's New MRT)

| | Dry Plant Weight (g) | | Dry Root Weight (g) | | Dry Shoot Weight (g) | |
|---|---|---|---|---|---|---|
| Treatment | 16 days w/o water | 9 days after Watering Resumed | 16 days w/o water | 9 days after Watering Resumed | 16 days w/o water | 9 days after Watering Resumed |
| UTC | 3.6a | 22.7a | 0.9a | 6.2a | 2.6a | 16.5a |
| 2.4 ppm CP | 1.7b | 11.6b | 0.3b | 3.2b | 1.5b | 8.5b |
| No CP | 1.5b | 8.9c | 0.2b | 2.5c | 1.2b | 6.4c |

4. Effect of CP on seed germination in vitro Two tests were conducted to determine the effect of seed germination of *Arabidopsis* seeds contacted with CP. The first test consisted of the following treatments:
Y2 MS (Sigma Murashige and Skoog Basal Salt Mixture)
Y2 MS+CP5000×
Y2 MS+125mM NaCl
Y2 MS+125 mM NaCl+CP5000×
One Petri dish for each treatment, with 200-300 seeds in each plate. The second test consisted of similar treatments:
Y2 MS
Y2 MS+CP1000×
Y2 MS+125 mM NaCl
Y2 MS+125 mM NaCl+CP1000×
Four plates for each treatment four plates, and 49 seeds were sown in each plate. No significant differences were observed among the treatments.

5. Effect of CP on root growth in vitro: Three tests were conducted to determine the effect of CP on *Arabidopsis* root growth in vitro. In the first test, seeds were germinated in V2 MS+125 mM NaCl medium, and then 4-day-old seedlings were subjected to the following conditions:

V2 MS+125 mM NaCl
V2 MS+125 mM NaCl+CP1000×
V2 MS+125 mM NaCl+CP5000×

In the 2$^{nd}$ test, 4-day-old seedlings germinated in V2 MS medium were transferred to the following Petri dishes containing
V2 MS
V2 MS+CP1000×V2 MS+CP5000×

Each treatment four plates, 4-6 seedlings in each plate

In the 3$^{rd}$ test, seedlings were grown in V2 MS, and then subjected to even higher concentrations of NaCl:
V2 MS
V2 MS+225 mM NaCl
V2 MS+225 mM NaCl+CP1000×
V2 MS+225 mM NaCl+CP5000×

Each treatment consisted of four plates, and 4-6 seedlings were placed in each plate. No significant differences were observed in these 3 tests.

Figure 6:
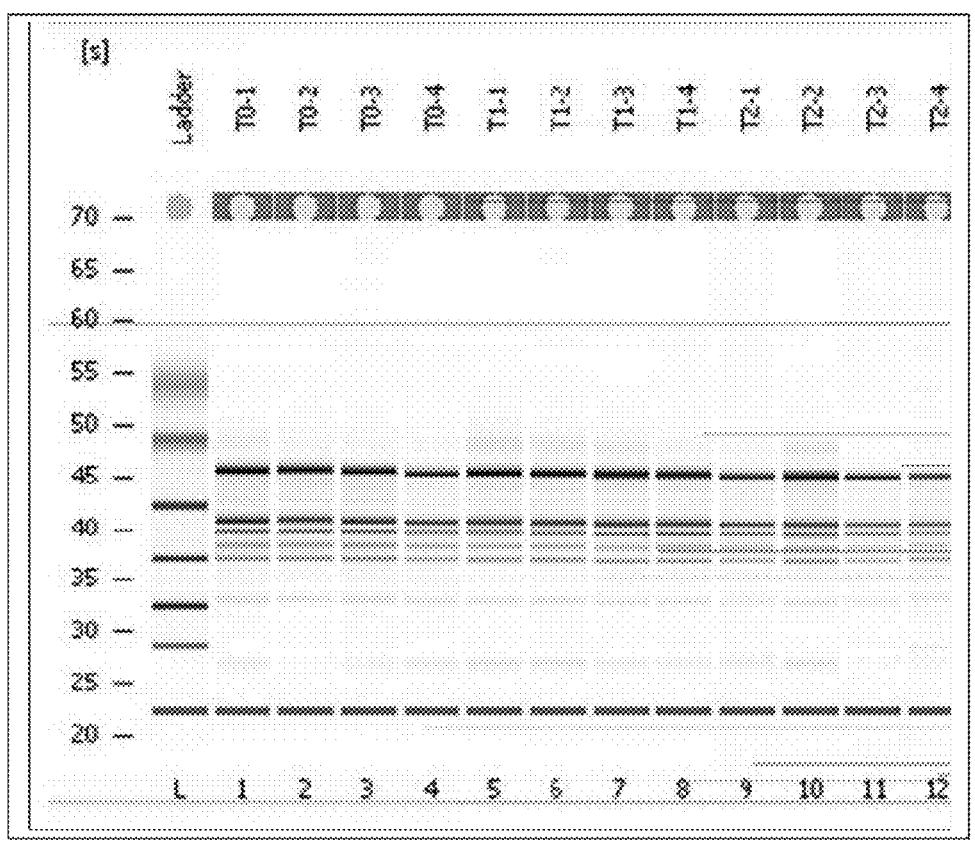
FIG. 6. RNA preparation quality as determined by BioAnalyzer.
Figure 12:
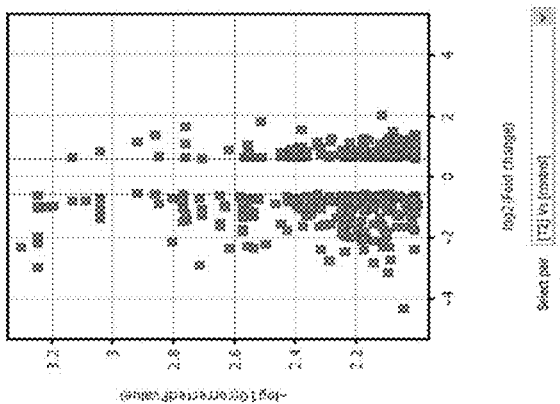
FIG. 12. Volcano Plot of *Arabidopsis* genes with expression levels changed ≥1.5 fold at p-value ≤0.01 after CP 1000 application vs. control.
Figure 13:
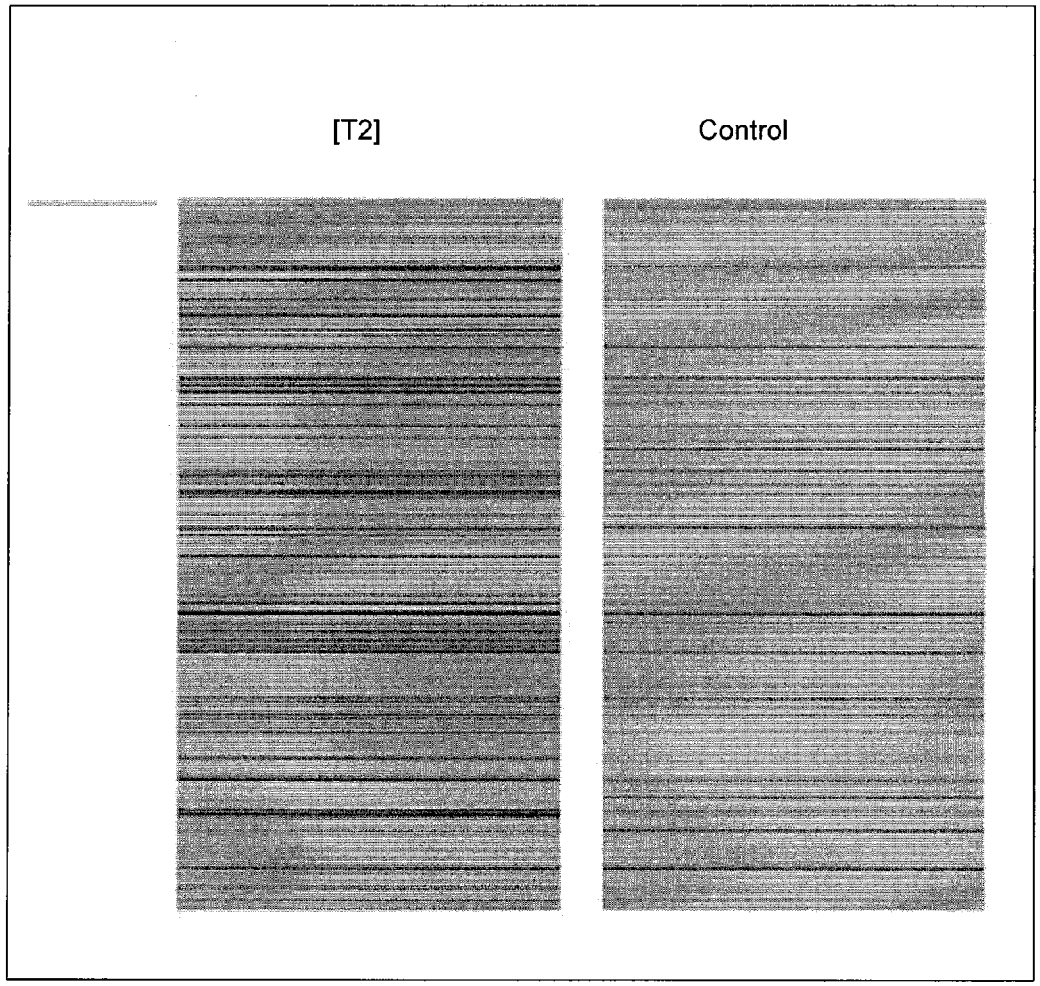
FIG. 13. Heatmap of CP 1000-regulated *Arabidopsis* genes compared to control.

6. CP-initiated gene expression: High quality RNAs were isolated from *Arabidopsis* rosette leaves, as shown in FIG. 6. (Y-axis: gene expression level fold change; X-axis: T2 on the left and control on the right). FIG. 12 is a Volcano plot of *Arabidopsis* genes whose expression levels changed ≥1.5 fold at p-value ≤0.01 in T2 versus control (Y-axis: -log base 10 of p-value (2=p-value 0.01); X-axis: gene expression level fold change). FIG. 13 is a Heatmap of CE-regulated genes compared to the control on the right, where each line represents a separate gene. For CE, the number of up-regulated genes was 60 and 160 for T1 and T2, respectively. Their expression level change ranged from 1.5 (the cut-off) to 4.0 fold, with an average fold change of 1.8 to 1.9.

Figure 18:
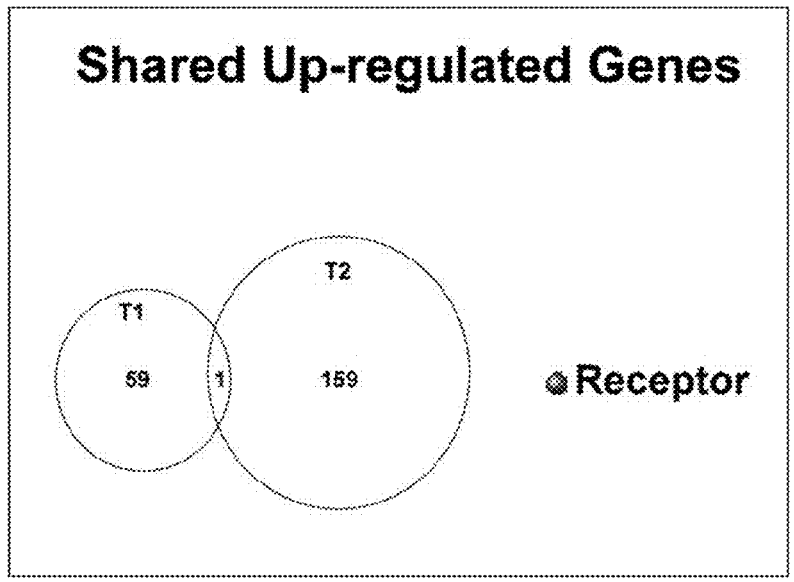
FIG. 18. Schematic of the shared up regulated *Arabidopsis* gene by a CP composition compositions.
Figure 19:
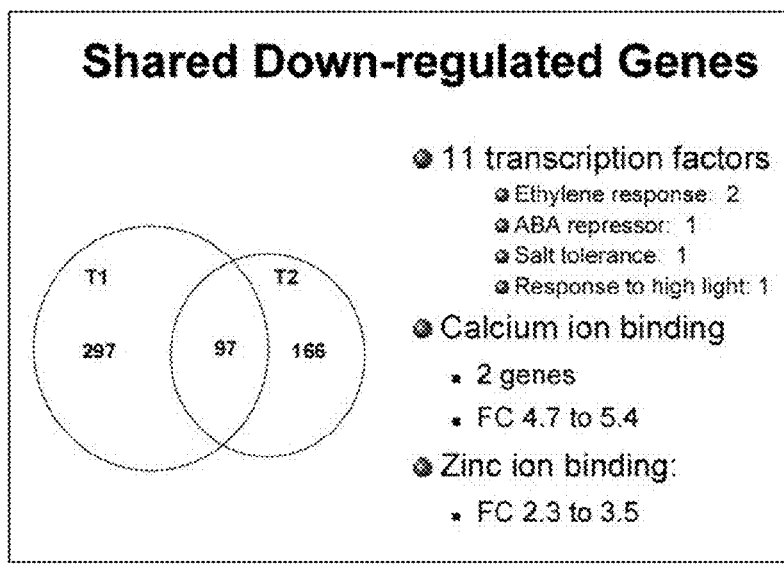
FIG. 19. Schematic of the shared down regulated *Arabidopsis* gene by a CP composition compositions.

A much greater number of genes were down-regulated at 6 hours after CP (T1) or CP1000 (T2) application as shown in FIGS. 18 and 19. For example, the expression of 394 genes was suppressed by T1, and their expression level was decreased by as much 38.4 fold. Similarly, for T2, 263 genes were suppressed, and their expression level was decreased by as much as 20.3 fold.

TABLE 5

Effect of CP and CE on *Arabidopsis* Gene Expression. (Note: Each array contained 43603 features. FC = fold change. FC 1.5 = 50% change. GeneSpring GX 10.0.2 was used, within array normalization done by Lowess method, between array normalization done by percentile shift, and baseline was shifted to median of all samples.)

| Treatment | Genes/transcripts regulated (no., % of total genes or transcripts) | | Up-regulated genes or transcripts | | | Down-regulated genes or transcripts | | |
|---|---|---|---|---|---|---|---|---|
| | P ≤ 0.01 | P ≤ 0.01 & FC ≥ 1.5 | Genes/ transcripts (no.) | Range of FC | Average FC | Genes/ transcripts (no.) | Range of FC | Average FC |
| T1 (CP) | 1382 (3.17%) | 456 (1.05%) | 60 | 1.5-3.2 | 1.9 | 396 | 1.5-38.4 | 2.8 |
| T2 (CE) | 1115 (2.56% | 423 (0.97% | 160 | 1.5-4.0 | 1.8 | 263 | 1.5-20.3 | 2.5 |

Figure 7:
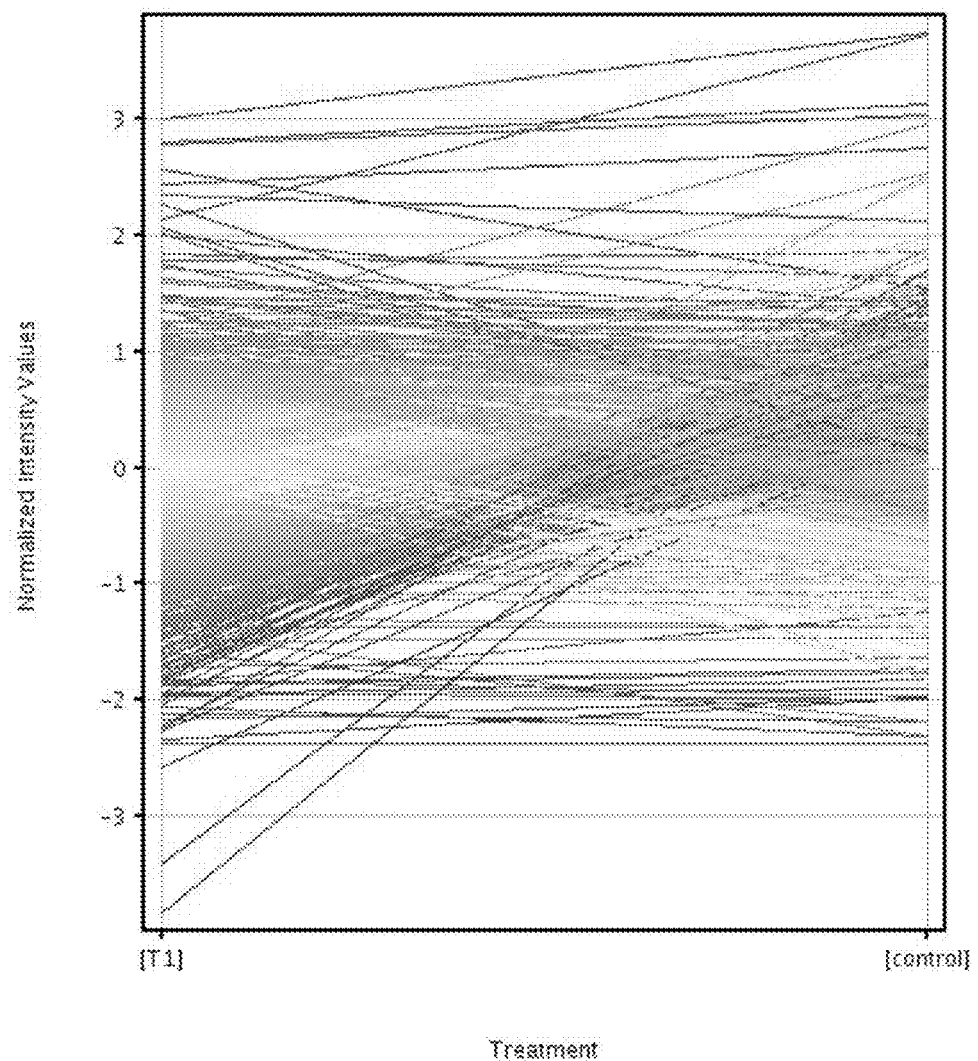
FIG. 7. Genome-wide expression profile of *Arabidopsis* after CP application vs. control.
Figure 17:
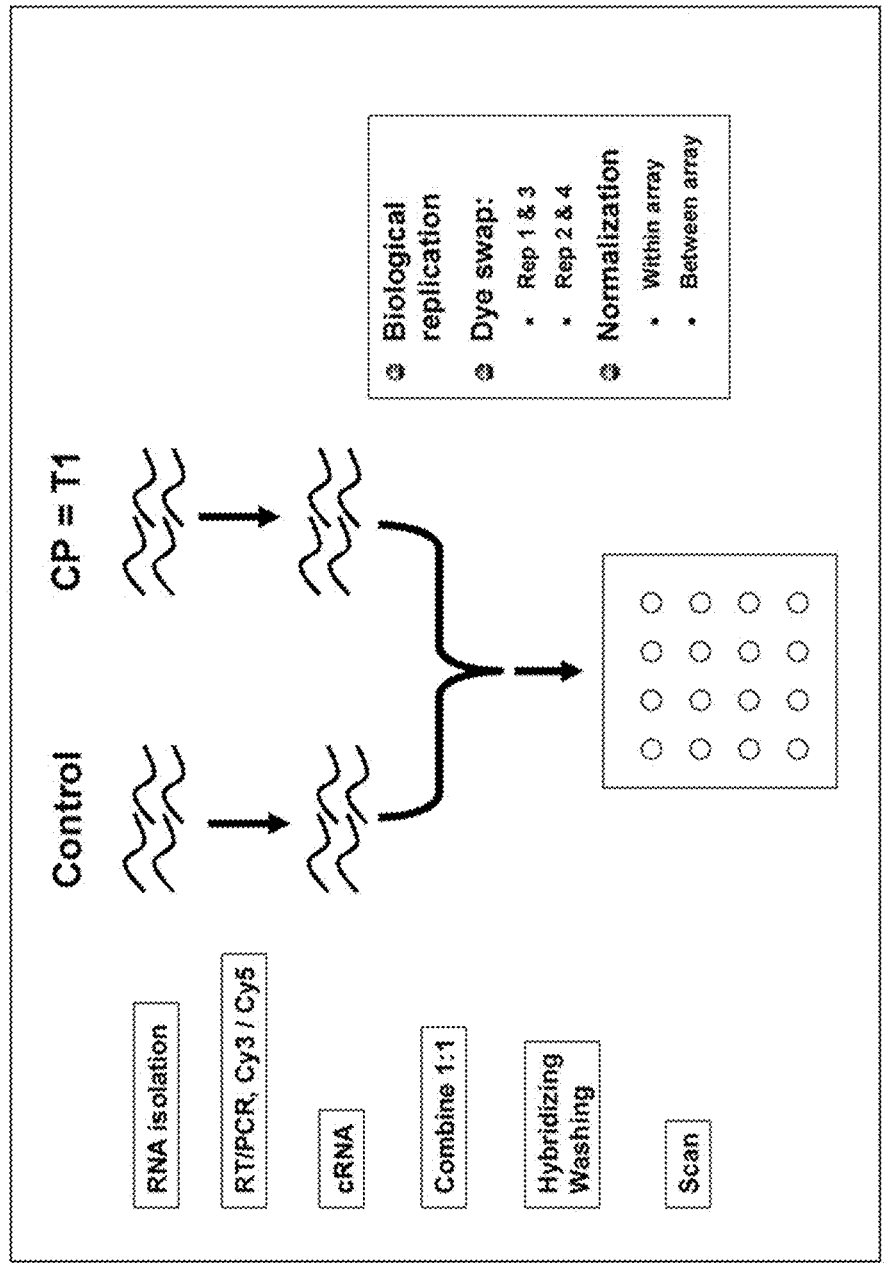
FIG. 17. Schematic of the *Arabidopsis* gene analysis after a CP composition treatment vs. control.

The expression technique is schematically depicted in FIG. 17. The Agilent Technologies's *Arabidopsis* Oligo Microarray V4 contains 43603 genes or transcripts that cover the plant's whole genome. Out of the 43,603 genes or transcripts (to be referred as genes for brevity below) that were hybridized, 1,382 genes or 1,115 genes showed significant fold changes at p-value ≤0.01 for T1 (CP), or comparative example CE, respectively, as summarized in Table 5. FIG. 7 depicts the genome-wide expression profile of *Arabidopsis* genes (43603 features) in T1 treatment versus control (Y-axis: gene expression level fold change; X-axis: T1 on the left and control on the right).

Figure 8:
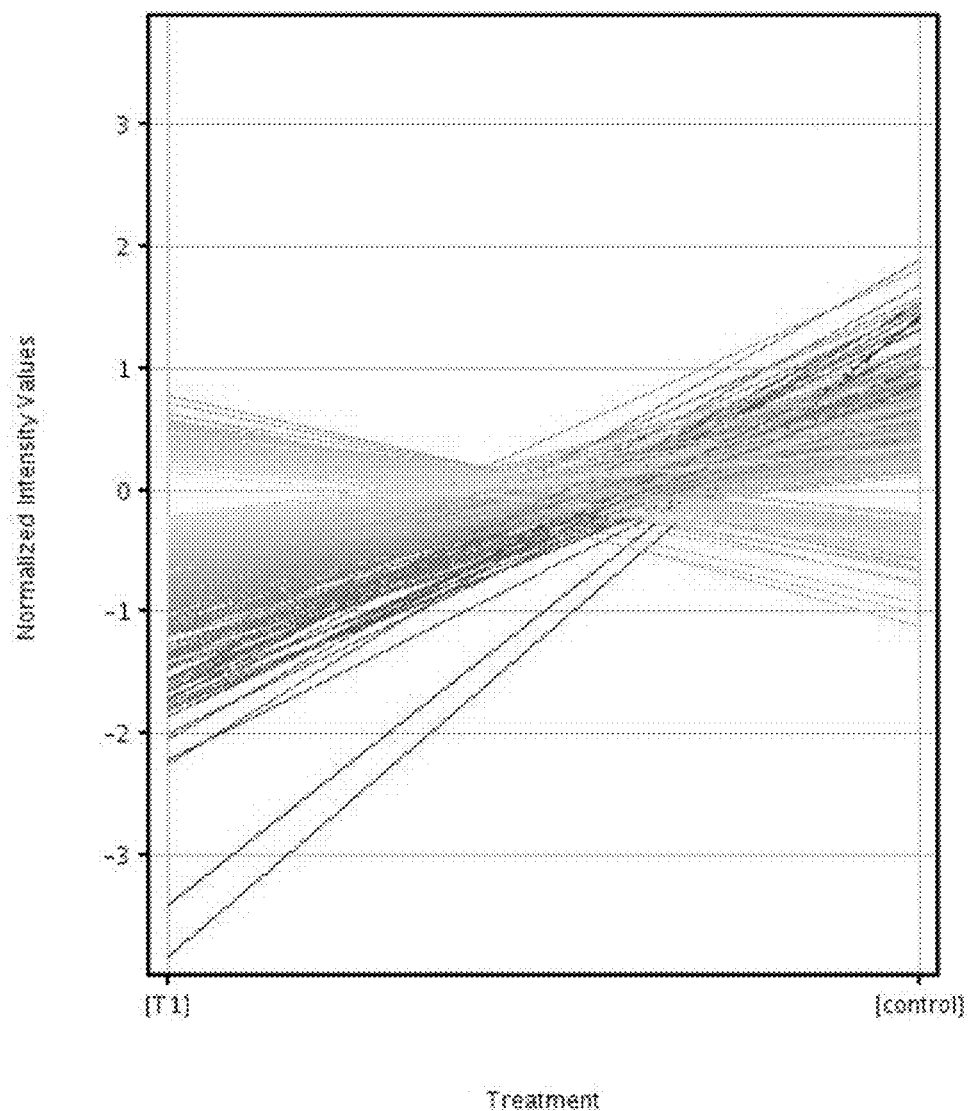
FIG. 8. Gene Expression Profile of *Arabidopsis* genes with expression levels changed ≥1.5 fold at p-value ≤0.01 after CP application vs. control.
Figure 9:
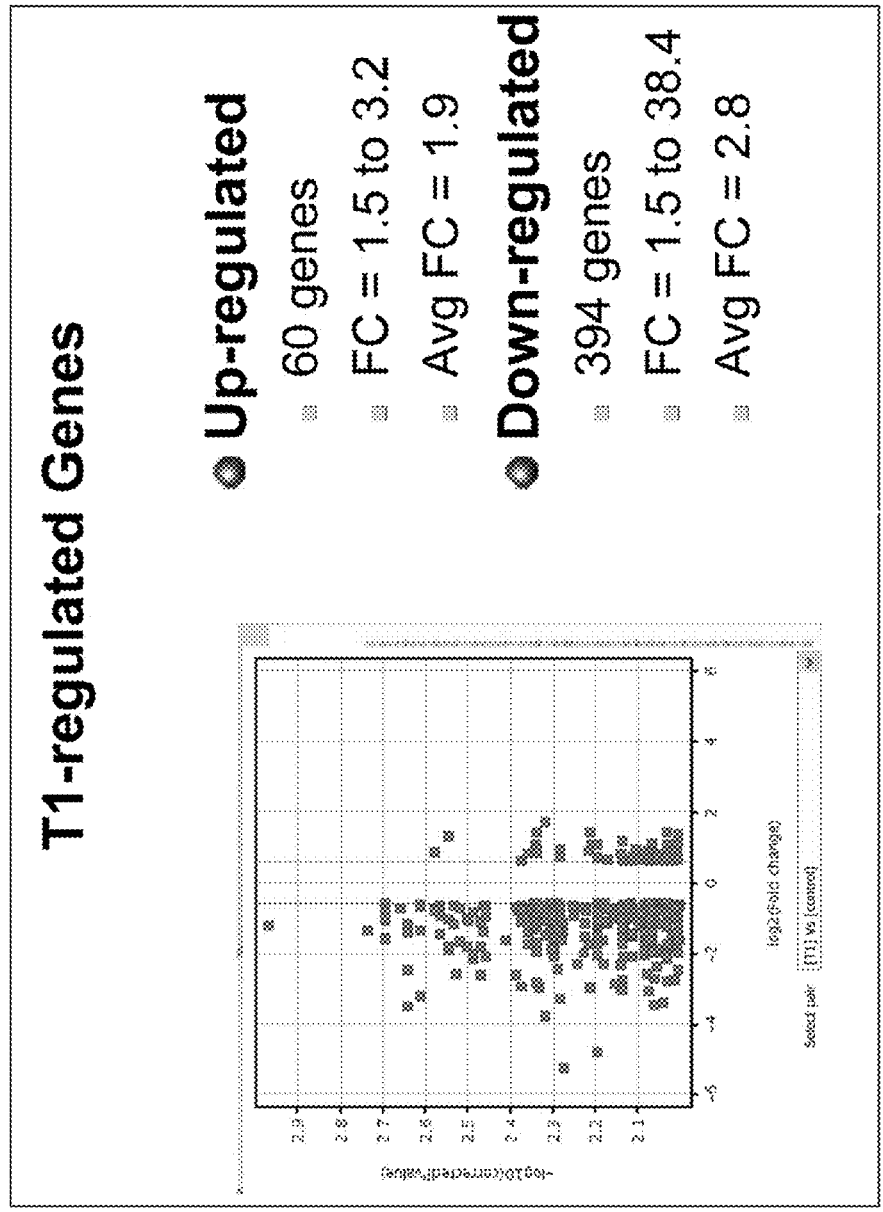
FIG. 9. Volcano Plot of *Arabidopsis* genes with expression levels changed ≥1.5 fold at p-value ≤0.01 after CP application vs. control.
Figure 10:
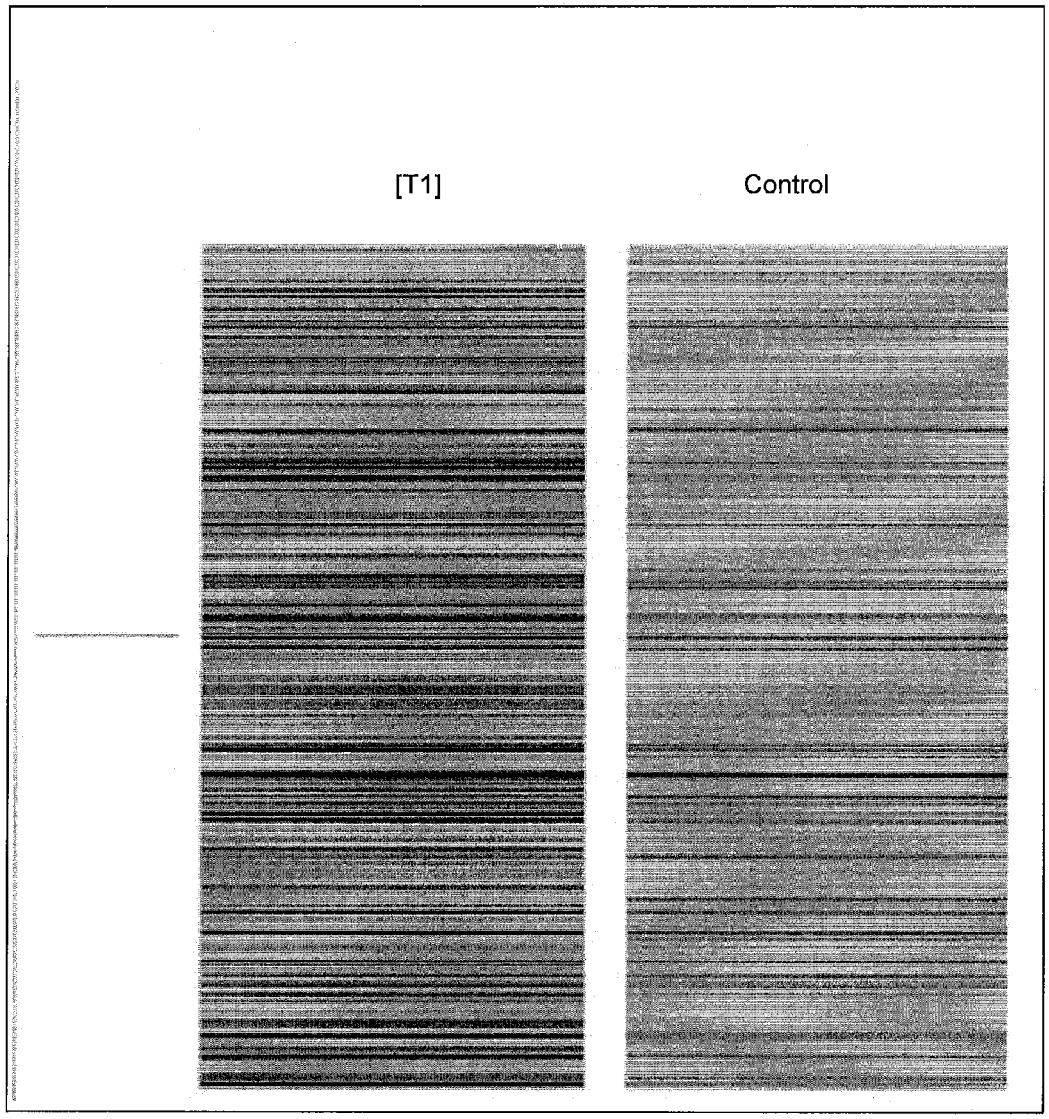
FIG. 10. Heatmap of CP-regulated *Arabidopsis* genes compared to control.
Figure 11:
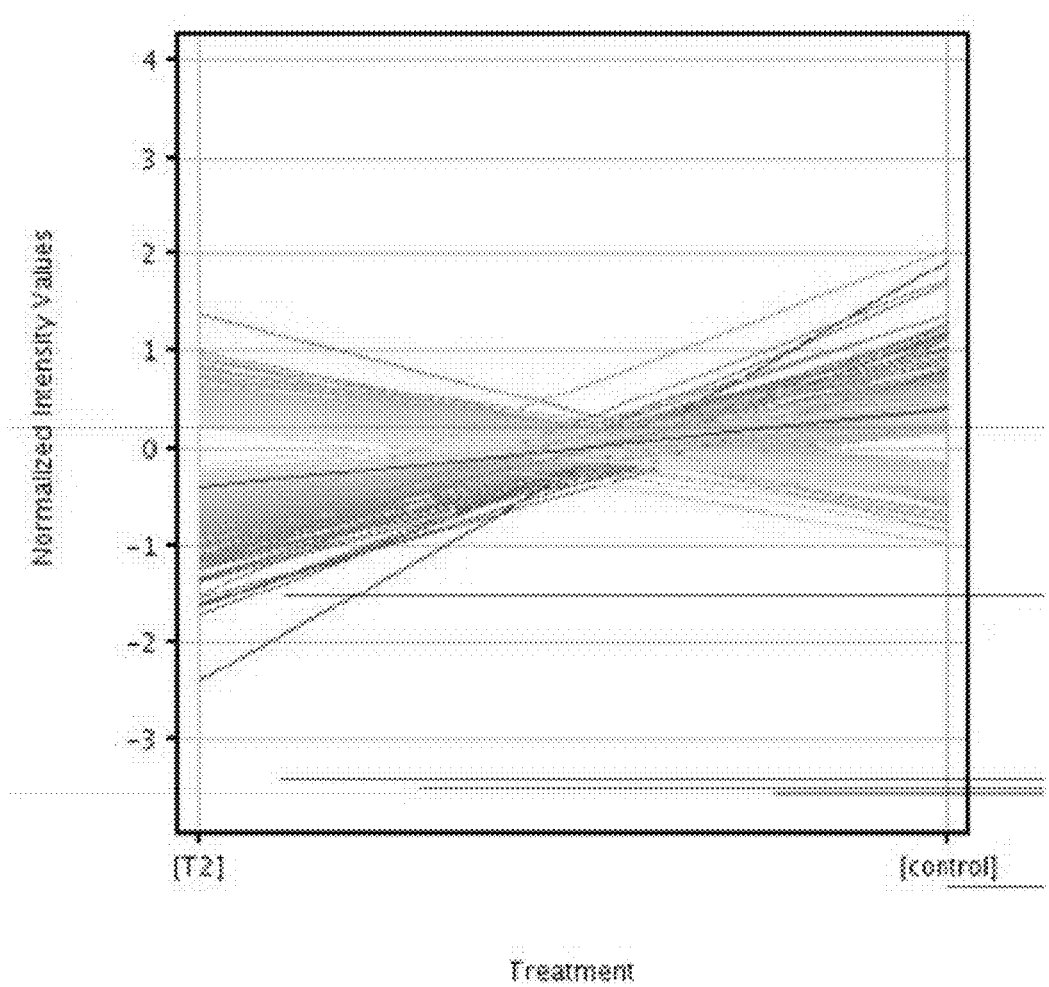
FIG. 11. Gene Expression Profile of *Arabidopsis* genes with expression levels changed ≥1.5 fold at p-value ≤0.01 after CP 1000 application vs. control.

Among them, the expression level of 456 and 423 genes was changed by at least 1.5 fold, or 50%, for T1. Thus, FIG. 8 depicts the expression profile plot of *Arabidopsis* genes whose expression levels changed ≥1.5 fold at p-value ≤0.01 (Y-axis: gene expression level fold change; X-axis: T1 on the left and control on the right). FIG. 9 is a Volcano plot of *Arabidopsis* genes whose expression levels changed ≥1.5 fold at p-value ≤0.01 (Y-axis: -log base 10 of p-value (2=p-value 0.01); X-axis: gene expression level fold change). FIG. 10 is a Heatmap of CP-regulated genes compared to the control on the right, where each line represents a separate gene. Thicker, darker lines represent up/down regulated genes. FIG. 11 depicts the expression profile plot of *Arabidopsis* genes whose expression levels changed ≥1.5 fold at p-value ≤0.01

Tables 6 and 7 provide details, including gene name, GeneBank accession number, and description (and potential functions), for those genes whose expression level changed ≥to 1.5 fold and had p≤0.01, responsive to T1 and responsive to T2, respectively. Table 6 lists 456 genes found to be responsive to T1 (CP contacted) treatment. Table 7 lists 423 genes responsive to T2 treatment. The following provides a short overview of some of these significantly differentially expressed genes. The large number of genes regulated by contact with CP was not predicted.

Among the 60 genes up-regulated by T1 are:
  5 genes encoding plant regulator production or responses: fold change 1.5 to 1.8 3 for auxin-responsive family proteins;
  2 for gibberellin 20 oxidase genes;
  3 genes encoding transporters (amino acid, carbohydrate, and purine): fold change 1.5 to 1.8;
  8 genes encoding enzymes: fold change 1.5 to 3.2;
  3 defense-related genes: fold change 1.6 to 2.6; and
  2 genes encoding transcription factor or transcription regulators: fold change 1.8 to 2.2 1 gene encoding ATPase/ ion movement: fold change 1.5

Among the 396 genes down-regulated by T1 are 34 genes encoding transcription factors, transcription regulators, initiators.

Among the 160 genes up-regulated by T2 are:
  10 genes encoding transcription factors: fold change 1.5 to 3.5;

39 genes encoding various kinds of enzymes, such as 12 for various protein kinases and 6 for hydrolases, and others, very diverse.

Among the 99 genes regulated by both T1 and T2 are:
1 gene (AT5G2063 receptor): up-regulated by T1 and T2;
11 genes encoding transcription factors, down 1.5 to 6.2 folds, including:
  i) Three containing WRKY element
  ii) One containing an ethylene-responsive element,
  iii) One containing ABA repressor,
  iv) One containing salt tolerance zinc finger motif,
  v) One containing high light responsive element;
4 putative disease resistance genes, down 1.5 to 2.4;
1 gene encoding putative chitinase protein, down 1.6 to 2.1;
2 genes encoding calcium ion binding proteins, down 4.7 to 5.5;
3 genes encoding zinc ion binding proteins, down 2.2 to 3.5;
1 encoding phosphate induced protein, down 3.2 to 5.0;
1 gene encoding ABC transporter family protein, down 3.2 to 3.5;
1 gene encoding cation/hydrogen exchanger (proton antiporter);
1 glycolipid transporter gene, down 3.3 to 3.7;
1 calmodulin-related protein, down 3.2 to 3.6; 1 protein kinase/sugar binding;
2 protease inhibitor genes, 1.8 to 3.4;
1 pectinesterase family protein, down 2.9 to 8.1;
1 oxidoreductase, down 2.6 to 4.0;
2 transmembrane receptor genes, down 1.9 to 3.4;
1 heat-shock protein gene, down 2.7 to 2.8; and
1 senescence associated protein, down 2.1 to 2.6.

Table 8 and Table 9 summarize the list of genes responsive to T1 and T2 (CP-induced) verses control, and transcription factor genes up regulated by T1 and genes up regulated by both T1 and T2, respectively. CP has demonstrated potency in regulating the expression of a large and diverse group of plant genes as represented by the *Arabidopsis* genome study. Some of the genes regulated by CP are involved in responses to or metabolism of plant hormones, such as auxins, gibberellic acid, abscisic acid, etc., and potentially other chemical stimuli. Some of the genes regulated by CP are involved in ion binding or mobility, plant defense, etc. Most remarkably, many of the genes regulated by CP are transcription factors. This indicates CP exerts effects on numerous plant biochemical and physiological processes. These benefits would be applicable to other plants. In some sense, CP acts like a nontraditional plant growth regulator. The aforementioned experimental further results show that CP can regulated gene expression in plants. This regulation can, for example, improve the growth of plants under stress, such as drought and salinity stress. Moreover, CP can provide improvement of a plant's drought recovery and can delay the appearance of wilting symptoms on plants under drought stress.

TABLE 6

List of Genes Responsive to T1 Treatment

| ProbeName | Fold change | Regulation | Gene Symbol | Description | Genbank Accession |
|---|---|---|---|---|---|
| A_84_P107652 | 1.55 | up | AUX1 | AUX1 (AUXIN RESISTANT 1); amino acid transmembrane transporter/transporter [AT2G38120.1] | NM_129368 |
| A_84_P867721 | 2.66 | up | AT4G16260 | glycosyl hydrolase family 17 protein [AT4G16260.1] | NM_117722 |
| A_84_P701013 | 1.89 | up | | | |
| A_84_P12387 | 2.25 | up | AT1G22600 | similar to late embryogenesis abundant domain-containing protein/LEA domain-containing protein [*Arabidopsis thaliana*] (TAIR: AT1G72100.1); similar to seed maturation protein PM27 [*Glycine max*] (GB: AAD30426.1); contains domain PTHR23241: SF1 (PTHR23241: SF1); contains domain PTHR23241 (PTHR23241) [AT1G22600.1] | NM_102107 |
| A_84_P811451 | 2.13 | up | | | |
| A_84_P10728 | 2.07 | up | ATGLR2.8 | ATGLR2.8 (*Arabidopsis thaliana* glutamate receptor 2.8) [AT2G29110.1] | NM_128468 |
| A_84_P116282 | 1.52 | up | ENDO4 | ENDO4 (ENDONUCLEASE 4); T/G mismatch-specific endonuclease/endonuclease/nucleic acid binding/single-stranded DNA specific endodeoxyribonuclease [AT4G21585.1] | NM_148368 |
| A_84_P20503 | 1.53 | up | AT4G34760 | auxin-responsive family protein [AT4G34760.1] | NM_119642 |
| A_84_P799324 | 1.73 | up | AT4G22390 | *Arabidopsis thaliana* Full-length cDNA Complete sequence from clone GSLTSIL79ZE03 of Silique of strain col-0 of *Arabidopsis thaliana* (thale cress) [BX829184] | |
| A_84_P850014 | 2.06 | up | | NM_120785 pepsin A {*Arabidopsis thaliana*} (exp = −1; wgp = 0; cg = 0), partial (39%) [TC304219] | |
| A_84_P822469 | 1.71 | up | AT3G63220 | kelch repeat-containing F-box family protein [AT3G63220.2] | NM_202752 |
| A_84_P22179 | 2.45 | up | AT3G30280 | transferase family protein [AT3G30280.1] | NM_113927 |
| A_84_P820625 | 1.71 | up | | | |
| A_84_P711161 | 1.55 | up | | Q29Q29_ARATH (Q29Q29) At1g17140, complete [TC290188] | |
| A_84_P10198 | 1.50 | up | AT5G22920 | zinc finger (C3HC4-type RING finger) family protein [AT5G22920.1] | NM_122198 |
| A_84_P15205 | 1.75 | up | ATOCT3 | ATOCT3 (*ARABIDOPSIS THALIANA* ORGANIC CATION/CARNITINE TRANSPORTER2); carbohydrate transmembrane transporter/sugar: hydrogen ion symporter [AT1G16390.1] | NM_101505 |
| A_84_P20053 | 1.84 | up | AT1G49910 | WD-40 repeat family protein/mitotic checkpoint protein, putative [AT1G49910.1] | NM_103878 |

TABLE 6-continued

List of Genes Responsive to T1 Treatment

| ProbeName | Fold change | Regulation | Gene Symbol | Description | Genbank Accession |
|---|---|---|---|---|---|
| A_84_P739523 | 1.52 | up | AT2G31150 | ATP binding/ATPase, coupled to transmembrane movement of ions, phosphorylative mechanism [AT2G31150.1] | NM_179829 |
| A_84_P794288 | 1.64 | up | AT1G08115 | snRNA [AT1G08115.1] | NR_022056 |
| A_84_P295294 | 1.55 | up | ATOFP15/OFP15 | ATOFP15/OFP15 (*Arabidopsis thaliana* ovate family protein 15) [AT2G36050.1] | NM_129164 |
| A_84_P862418 | 1.52 | up | | NM_103556 ATPUP11; purine transporter {*Arabidopsis thaliana*} (exp = −1; wgp = 0; cg = 0), partial (5%) [TC313905] | |
| A_84_P768252 | 2.62 | up | AT5G43525 | Encodes a defensin-like (DEFL) family protein. [AT5G43525.1] | NM_001036928 |
| A_84_P571538 | 2.09 | up | AT4G10420 | similar to F-box family protein [*Arabidopsis thaliana*] (TAIR: AT4G10400.2); similar to F-box family protein [*Arabidopsis thaliana*] (TAIR: AT4G10400.1); similar to hypothetical protein [*Vitis vinifera*] (GB: CAN74740.1); contains InterPro domain Leucine-rich repeat 2 (InterPro: IPR013101) [AT4G10420.1] | NM_117110 |
| A_84_P12995 | 2.60 | up | AT5G06940 | leucine-rich repeat family protein [AT5G06940.1] | NM_120776 |
| A_84_P766972 | 2.10 | up | ATGDU5 | ATGDU5 (*ARABIDOPSIS THALIANA* GLUTAMINE DUMPER 5) [AT5G24920.1] | NM_122401 |
| A_84_P753753 | 1.56 | up | AT1G52618 | unknown protein [AT1G52618.1] | NM_001084236 |
| A_84_P832994 | 1.61 | up | AT2G47860 | phototropic-responsive NPH3 family protein [AT2G47860.2] | NM_201982 |
| A_84_P814302 | 1.6823 | up | AT5G11420 | similar to unknown protein [*Arabidopsis thaliana*] (TAIR: AT5G25460.1); similar to unknown [*Ricinus communis*] (GB: CAB02653.1); contains InterPro domain Protein of unknown function DUF642 (InterPro: IPR006946); contains InterPro domain Galactose-binding like (InterPro: IPR008979) [AT5G11420.1] | NM_121180 |
| A_84_P793397 | 1.77 | up | AT1G23200 | AV563397 *Arabidopsis thaliana* green siliques Columbia *Arabidopsis thaliana* cDNA clone SQ186f07F 3', mRNA sequence [AV563397] | |
| A_84_P554830 | 1.80 | up | AT5G20635 | receptor [AT5G20635.1] | NM_147870 |
| A_84_P816758 | 1.79 | up | | | |
| A_84_P589074 | 1.68 | up | AT2G25050 | formin homology 2 domain-containing protein/FH2 domain-containing protein [AT2G25050.1] | NM_128062 |
| A_84_P526317 | 1.55 | up | AT4G15960 | epoxide hydrolase, putative [AT4G15960.1] | NM_117688 |
| A_84_P814618 | 1.54 | up | AT5G22920 | zinc finger (C3HC4-type RING finger) family protein [AT5G22920.1] | NM_122198 |
| A_84_P576925 | 1.75 | up | AT4G22390 | F-box family protein-related [AT4G22390.1] | NM_118365 |
| A_84_P194534 | 1.65 | up | AT4G02482 | chloroplast outer envelope GTP-binding protein, putative [AT4G02482.1] | NM_148197 |
| A_84_P20189 | 1.50 | up | AT3G03830 | auxin-responsive protein, putative [AT3G03830.1] | NM_111254 |
| A_84_P16678 | 1.55 | up | GA5 | GA5 (GA REQUIRING 5); gibberellin 20-oxidase/ gibberellin 3-beta-dioxygenase [AT4G25420.1] | NM_118674 |
| A_84_P814311 | 2.66 | up | AT4G16260 | glycosyl hydrolase family 17 protein [AT4G16260.1] | NM_117722 |
| A_84_P850601 | 1.64 | up | AT2G24350 | RNA recognition motif (RRM)-containing protein [AT2G24350.1] | NM_127997 |
| A_84_P544696 | 2.09 | up | AT2G36110 | 3'-5' exonuclease domain-containing protein [AT2G36110.1] | NM_129170 |
| A_84_P19299 | 3.21 | up | AT3G19300 | protein kinase family protein [AT3G19300.1] | NM_112817 |
| A_84_P861444 | 1.75 | up | | Q9LQV5_ARATH (Q9LQV5) F10B6.16, complete [TC313407] | |
| A_84_P828086 | 2.22 | up | MNP | MNP (MONOPOLE); transcription factor [AT3G50870.1] | NM_114947 |
| A_84_P19616 | 1.88 | up | YAP169 | YAP169 (GIBBERELLIN 20 OXIDASE 3); gibberellin 20-oxidase [AT5G07200.1] | NM_120802 |
| A_84_P713168 | 1.92 | up | AT1G15405 | other RNA [AT1G15405.1] | NR_022088 |
| A_84_P861555 | 1.74 | up | | ATCAPZA alpha subunit of F-actin capping protein {*Arabidopsis thaliana*} (exp = −1; wgp = 0; cg = 0), partial (18%) [TC313448] | |
| A_84_P727466 | 1.79 | up | | Q9FJ43_ARATH (Q9FJ43) Magnesium chelatase subunit of protochlorophyllide reductase, complete [TC299558] | |
| A_84_P21135 | 1.77 | up | AT3G03820 | auxin-responsive protein, putative [AT3G03820.1] | NM_111253 |
| A_84_P18515 | 1.55 | up | AT4G07820 | pathogenesis-related protein, putative [AT4G07820.1] | NM_116854 |
| A_84_P820592 | 1.63 | up | AT5G50180 | protein kinase, putative [AT5G50180.1] | NM_124397 |
| A_84_P22812 | 1.85 | up | ARR15 | ARR15 (RESPONSE REGULATOR 15); transcription regulator [AT1G74890.1] | NM_106147 |
| A_84_P21426 | 1.63 | up | AT4G29360 | glycosyl hydrolase family 17 protein [AT4G29360.2] | NM_179225 |
| A_84_P803498 | 1.54 | up | | *Arabidopsis thaliana* clone 231825 mRNA sequence [DQ108778] | |
| A_84_P818485 | 1.63 | up | | Q9C5U7_ARATH (Q9C5U7) Long-chain acyl-CoA synthetase, partial (36%) [TC302121] | |

TABLE 6-continued

List of Genes Responsive to T1 Treatment

| ProbeName | Fold change | Regulation | Gene Symbol | Description | Genbank Accession |
|---|---|---|---|---|---|
| A_84_P16764 | 1.51 | up | AT5G02750 | zinc finger (C3HC4-type RING finger) family protein [AT5G02750.1] | NM_120353 |
| A_84_P568436 | 1.62 | up | ATBRXL3/BRX-LIKE3 | ATBRXL3/BRX-LIKE3 (BREVIS RADIX-LIKE 3) [AT1G54180.1] | NM_104296 |
| A_84_P830132 | 1.6715 | up | AT4G14290 | similar to unknown protein [*Arabidopsis thaliana*] (TAIR: AT3G23540.1); similar to unnamed protein product [*Vitis vinifera*] (GB: CAO71078.1); contains InterPro domain Alpha/beta hydrolase fold-1 (InterPro: IPR000073) [AT4G14290.1] | NM_117506 |
| A_84_P855153 | 1.6357 | up | AT2G33793 | similar to unknown protein [*Arabidopsis thaliana*] (TAIR: AT2G46980.2); similar to unnamed protein product [*Vitis vinifera*] (GB: CAO63047.1) [AT2G33793.1] | NM_201864 |
| A_84_P842922 | 1.8206 | up | AT3G13980 | similar to unknown protein [*Arabidopsis thaliana*] (TAIR: AT1G54200.1); similar to hypothetical protein [*Vitis vinifera*] (GB: CAN69469.1) [AT3G13980.1] | NM_112252 |
| A_84_P787273 | 1.7856 | down | AT5G24600 | similar to unknown protein [*Arabidopsis thaliana*] (TAIR: AT3G18215.1); similar to unnamed protein product [*Vitis vinifera*] (GB: CAO65983.1); contains InterPro domain Protein of unknown function DUF599 (InterPro: IPR006747) [AT5G24600.1] | NM_122368 |
| A_84_P520558 | 1.9051 | down | AT1G52855 | similar to unknown protein [*Arabidopsis thaliana*] (TAIR: AT3G15534.1); similar to unnamed protein product [*Vitis vinifera*] (GB: CAO39221.1) [AT1G52855.1] | NM_202282 |
| A_84_P12030 | 1.6498 | down | AT5G01100 | similar to unknown protein [*Arabidopsis thaliana*] (TAIR: AT2G37980.1); similar to unknown protein [*Arabidopsis thaliana*] (TAIR: AT3G54100.1); similar to unnamed protein product [*Vitis vinifera*] (GB: CAO15763.1); contains InterPro domain Protein of unknown function DUF246, plant (InterPro: IPR004348) [AT5G01100.1] | NM_120188 |
| A_84_P858544 | 2.0297 | down | AT2G40000 | similar to unknown protein [*Arabidopsis thaliana*] (TAIR: AT3G55840.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] | NM_129558 |
| A_84_P306860 | 1.6315 | down | AT5G10695 | similar to unknown protein [*Arabidopsis thaliana*] (TAIR: AT5G57123.1); similar to unknown [*Picea sitchensis*] (GB: ABK22689.1) [AT5G10695.1] | NM_121107 |
| A_84_P555790 | 1.52 | down | AT5G48657 | defense protein-related [AT5G48657.2] | NM_203180 |
| A_84_P823733 | 1.73 | down | GATL10 | GATL10 (Galacturonosyltransferase-like 10); polygalacturonate 4-alpha-galacturonosyltransferase/ transferase, transferring hexosyl groups [AT3G28340.1] | NM_113753 |
| A_84_P586644 | 2.37 | down | DVL20/RTFL1 | DVL20/RTFL1 (*ROTUNDIFOLIA* 1) [AT3G53232.1] | NM_202692 |
| A_84_P13200 | 2.41 | down | AT1G51820 | leucine-rich repeat protein kinase, putative [AT1G51820.1] | NM_104062 |
| A_84_P20984 | 1.53 | down | AT1G02850 | glycosyl hydrolase family 1 protein [AT1G02850.1] | NM_202017 |
| A_84_P610533 | 2.03 | down | AT3G02030 | hydrolase, alpha/beta fold family protein [AT3G02030.1] | NM_111069 |
| A_84_P830975 | 1.603 | down | AT1G30755 | similar to unknown protein [*Arabidopsis thaliana*] (TAIR: AT1G34320.1); similar to unnamed protein product [*Vitis vinifera*] (GB: CAO60978.1); contains InterPro domain Protein of unknown function DUF668 (InterPro: IPR007700) [AT1G30755.1] | NM_102812 |
| A_84_P147008 | 1.92 | down | AT1G72070 | DNAJ heat shock N-terminal domain-containing protein [AT1G72070.1] | NM_105865 |
| A_84_P826147 | 1.70 | down | AT2G42760 | similar to unnamed protein product [*Vitis vinifera*] (GB: CAO69913.1) [AT2G42760.1] | NM_129837 |
| A_84_P89769 | 1.90 | down | AT2G35930 | U-box domain-containing protein [AT2G35930.1] | NM_129152 |
| A_84_P801414 | 1.57 | down | AT3G48460 | GDSL-motif lipase/hydrolase family protein [AT3G48460.1] | NM_114705 |
| A_84_P856515 | 1.59 | down | TMP-C | TMP-C (PLASMA MEMBRANE INTRINSIC PROTEIN 1; 4) [AT4G00430.2] | NM_202760 |
| A_84_P793001 | 2.87 | down | LOX3 | LOX3 (Lipoxygenase 3); iron ion binding/ lipoxygenase/metal ion binding/oxidoreductase, acting on single donors with incorporation of molecular oxygen, incorporation of two atoms of oxygen [AT1G17420.1] | NM_101603 |
| A_84_P13494 | 3.99 | down | AT2G36690 | oxidoreductase, 2OG-Fe(II) oxygenase family protein [AT2G36690.1] | NM_129224 |
| A_84_P13750 | 1.68 | down | AT3G60270 | uclacyanin, putative [AT3G60270.1] | NM_115891 |

TABLE 6-continued

List of Genes Responsive to T1 Treatment

| ProbeName | Fold change | Regulation | Gene Symbol | Description | Genbank Accession |
|---|---|---|---|---|---|
| A_84_P756195 | 1.64 | down | AT2G04070 | transporter [AT2G04070.1] | NM_126448 |
| A_84_P538274 | 1.6041 | down | AT1G30755 | similar to unknown protein [*Arabidopsis thaliana*] (TAIR: AT1G34320.1); similar to unnamed protein product [*Vitis vinifera*] (GB: CAO60978.1); contains InterPro domain Protein of unknown function DUF668 (InterPro: IPR007700) [AT1G30755.1] | NM_102812 |
| A_84_P574794 | 2.48 | down | AT2G20142 | *Arabidopsis thaliana* At2g20141 mRNA, complete cds [AF361584] | |
| A_84_P810559 | 1.9037 | down | AT2G40000 | similar to unknown protein [*Arabidopsis thaliana*] (TAIR: AT3G55840.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] | NM_129558 |
| A_84_P164303 | 1.66 | down | AT5G58680 | armadillo/beta-catenin repeat family protein [AT5G58680.1] | NM_125255 |
| A_84_P23149 | 6.85 | down | AT3G46660 | UDP-glucoronosyl/UDP-glucosyl transferase family protein [AT3G46660.1] | NM_114533 |
| A_84_P820492 | 2.81 | down | AT3G29575 | similar to TMAC2 (TWO OR MORE ABRES-CONTAINING GENE 2) [*Arabidopsis thaliana*] (TAIR: AT3G02140.1); similar to unnamed protein product [*Vitis vinifera*] (GB: CAO49169.1); contains InterPro domain Protein of unknown function DUF1675 (InterPro: IPR012463) [AT3G29575.4] | NM_001084753 |
| A_84_P232439 | 1.59 | down | WRKY18 | WRKY18 (WRKY DNA-binding protein 18); transcription factor [AT4G31800.1] | NM_119329 |
| A_84_P13013 | 1.6377 | down | AT1G18380 | Identical to Uncharacterized protein At1g18380 precursor [*Arabidopsis Thaliana*] (GB: Q5BQ05; GB: Q5Q0G6; GB: Q8RX30; GB: Q9LPQ6); similar to unknown protein [*Arabidopsis thaliana*] (TAIR: AT1G67025.1); similar to unnamed protein product [*Vitis vinifera*] (GB: CAO68096.1) [AT1G18380.1] | NM_101696 |
| A_84_P18649 | 1.65 | down | SQD2 | SQD2 (SULFOQUINOVOSYLDIACYLGLYCEROL 2); UDP-sulfoquinovose: DAG sulfoquinovosyltransferase/ transferase, transferring glycosyl groups [AT5G01220.1] | NM_120200 |
| A_84_P584025 | 2.33 | down | AT4G08555 | unknown protein [AT4G08555.1] | NM_179014 |
| A_84_P13104 | 2.79 | down | WRKY48 | WRKY48 (WRKY DNA-binding protein 48); transcription factor [AT5G49520.1] | NM_124329 |
| A_84_P22140 | 4.31 | down | AtMYB15/AtY19/MYB15 | AtMYB15/AtY19/MYB15 (myb domain protein 15); DNA binding/transcription factor [AT3G23250.1] | NM_001035670 |
| A_84_P823526 | 1.53 | down | AT5G04250 | OTU-like cysteine protease family protein [AT5G04250.2] | NM_001125696 |
| A_84_P869312 | 4.42 | down | AT1G73010 | phosphoric monoester hydrolase [AT1G73010.1] | NM_105959 |
| A_84_P12859 | 1.75 | down | AT4G12410 | auxin-responsive family protein [AT4G12410.1] | NM_117311 |
| A_84_P54840 | 2.61 | down | CYP707A4 | CYP707A4 (cytochrome P450, family 707, subfamily A, polypeptide 4); oxygen binding [AT3G19270.1] | NM_112814 |
| A_84_P764402 | 28.36 | down | ATTPS03 | ATTPS03 (*Arabidopsis thaliana* terpene synthase 03) [AT4G16740.1] | NM_001036574 |
| A_84_P15688 | 1.91 | down | AT1G06260 | cysteine proteinase, putative [AT1G06260.1] | NM_100508 |
| A_84_P13733 | 1.70 | down | AT3G55980 | zinc finger (CCCH-type) family protein [AT3G55980.1] | NM_115456 |
| A_84_P289964 | 1.6128 | down | AT1G19020 | similar to unknown protein [*Arabidopsis thaliana*] (TAIR: AT3G48180.1); similar to unnamed protein product [*Vitis vinifera*] (GB: CAO40966.1) [AT1G19020.1] | NM_101759 |
| A_84_P831396 | 1.6949 | down | AT1G20310 | similar to unknown protein [*Arabidopsis thaliana*] (TAIR: AT1G76070.1); similar to hypothetical protein [*Vitis vinifera*] (GB: CAN83887.1) [AT1G20310.1] | NM_101882 |
| A_84_P798445 | 1.69 | down | | AYBLJ42TR pooled cDNA populations *Arabidopsis thaliana* cDNA, mRNA sequence [EG497635] | |
| A_84_P21026 | 3.43 | down | RD20 | RD20 (RESPONSIVE TO DESSICATION 20); calcium ion binding [AT2G33380.1] | NM_128898 |
| A_84_P228659 | 3.049 | down | AT2G32190 | similar to unknown protein [*Arabidopsis thaliana*] (TAIR: AT2G32210.1); similar to unknown [*Populus trichocarpa*] (GB: ABK92801.1); contains domain PD188784 (PD188784) [AT2G32190.1] | NM_001084521 |
| A_84_P537220 | 2.73 | down | AT5G57510 | unknown protein [AT5G57510.1] | NM_125132 |
| A_84_P14985 | 1.70 | down | ATERF-2/ATERF2/ERF2 | ATERF-2/ATERF2/ERF2 (ETHYLENE RESPONSE FACTOR 2); DNA binding/transcription activator/ transcription factor [AT5G47220.1] | NM_124093 |
| A_84_P16247 | 2.56 | down | DDF1 | DDF1 (DWARF AND DELAYED FLOWERING 1); DNA binding/transcription factor [AT1G12610.1] | NM_101131 |

TABLE 6-continued

List of Genes Responsive to T1 Treatment

| ProbeName | Fold change | Regulation | Gene Symbol | Description | Genbank Accession |
|---|---|---|---|---|---|
| A_84_P82909 | 2.0051 | down | AT1G17830 | similar to unknown protein [Arabidopsis thaliana] (TAIR: AT1G73210.1); similar to unnamed protein product [Vitis vinifera] (GB: CAO45300.1); contains InterPro domain Protein of unknown function DUF789 (InterPro: IPR008507) [AT1G17830.1] | NM_101646 |
| A_84_P578899 | 2.6442 | down | AT5G49600 | similar to unknown protein [Arabidopsis thaliana] (TAIR: AT1G09310.1); similar to unknown [Populus trichocarpa] (GB: ABK94967.1); contains InterPro domain Protein of unknown function DUF538 (InterPro: IPR007493) [AT5G49600.1] | NM_124338 |
| A_84_P790714 | 2.73 | down | AT3G44510 | similar to esterase/lipase/thioesterase family protein [Arabidopsis thaliana] (TAIR: AT1G08310.1); similar to esterase/lipase/thioesterase family protein [Arabidopsis thaliana] (TAIR: AT1G08310.2); similar to hypothetical protein [Vitis vinifera] (GB: CAN60741.1); contains domain SSF53474 (SSF53474) [AT3G44510.1] | NM_114319 |
| A_84_P12212 | 2.8987 | down | AT1G56060 | similar to unknown protein [Arabidopsis thaliana] (TAIR: AT2G32190.1); similar to unnamed protein product [Vitis vinifera] (GB: CAO68639.1); contains domain PD188784 (PD188784) [AT1G56060.1] | NM_104484 |
| A_84_P13988 | 1.66 | down | AT5G25450 | ubiquinol-cytochrome C reductase complex 14 kDa protein, putative [AT5G25450.1] | NM_122455 |
| A_84_P23507 | 1.59 | down | ATCP1 | ATCP1 (CA2+-BINDING PROTEIN 1); calcium ion binding [AT5G49480.1] | NM_124325 |
| A_84_P21145 | 1.74 | down | CHAT | CHAT (ACETYL COA: (Z)-3-HEXEN-1-OL ACETYLTRANSFERASE); acetyl CoA: (Z)-3-hexen-1-ol acetyltransferase [AT3G03480.1] | NM_111219 |
| A_84_P172941 | 1.5946 | down | AT2G18690 | similar to unknown protein [Arabidopsis thaliana] (TAIR: AT2G18680.1); similar to hypothetical protein OsI_029427 [Oryza sativa (indica cultivar-group)] (GB: EAZ08195.1) [AT2G18690.1] | NM_127425 |
| A_84_P597276 | 8.0472 | down | AT3G25240 | similar to unknown protein [Arabidopsis thaliana] (TAIR: AT3G07350.1); similar to unnamed protein product [Vitis vinifera] (GB: CAO39951.1); contains InterPro domain Protein of unknown function DUF506, plant (InterPro: IPR006502) [AT3G25240.1] | NM_113430 |
| A_84_P21496 | 1.56 | down | AT5G03700 | PAN domain-containing protein [AT5G03700.1] | NM_120451 |
| A_84_P102986 | 2.29 | down | AT2G27080 | harpin-induced protein-related/HIN1-related/harpin-responsive protein-related [AT2G27080.1] | NM_128266 |
| A_84_P13077 | 5.54 | down | CML37/CML39 | CML37/CML39; calcium ion binding [AT5G42380.1] | NM_123603 |
| A_84_P16568 | 2.5821 | down | AT3G55840 | similar to unknown protein [Arabidopsis thaliana] (TAIR: AT2G40000.1); similar to unnamed protein product [Vitis vinifera] (GB: CAO41329.1); contains InterPro domain Hs1pro-1, C-terminal (InterPro: IPR009743); contains InterPro domain Hs1pro-1, N-terminal (InterPro: IPR009869) [AT3G55840.1] | NM_115442 |
| A_84_P791120 | 6.239 | down | AT3G25240 | similar to unknown protein [Arabidopsis thaliana] (TAIR: AT3G07350.1); similar to unnamed protein product [Vitis vinifera] (GB: CAO39951.1); contains InterPro domain Protein of unknown function DUF506, plant (InterPro: IPR006502) [AT3G25240.1] | NM_113430 |
| A_84_P113182 | 3.67 | down | AT4G39670 | glycolipid binding/glycolipid transporter [AT4G39670.1] | NM_120127 |
| A_84_P10528 | 2.52 | down | AT1G51800 | leucine-rich repeat protein kinase, putative [AT1G51800.1] | NM_104059 |
| A_84_P12218 | 1.7164 | down | AT5G64870 | similar to unknown protein [Arabidopsis thaliana] (TAIR: AT5G25250.1); similar to unknown protein [Arabidopsis thaliana] (TAIR: AT5G25260.1); similar to 80C09_16 [Brassica rapa subsp. pekinensis] (GB: AAZ41827.1); contains domain PTHR13806: SF3 (PTHR13806: SF3); contains domain PTHR13806 (PTHR13806) [AT5G64870.1] | NM_125885 |
| A_84_P12877 | 2.21 | down | AT4G20860 | FAD-binding domain-containing protein [AT4G20860.1] | NM_118204 |
| A_84_P15573 | 1.52 | down | ADT4 | ADT4 (AROGENATE DEHYDRATASE 4); arogenate dehydratase/prephenate dehydratase [AT3G44720.1] | NM_114340 |
| A_84_P19193 | 1.5653 | down | AT2G37980 | similar to unknown protein [Arabidopsis thaliana] (TAIR: AT5G01100.1); similar to unknown protein [Arabidopsis thaliana] (TAIR: AT3G54100.1); similar to unnamed protein product [Vitis vinifera] | NM_129355 |

TABLE 6-continued

List of Genes Responsive to T1 Treatment

| ProbeName | Fold change | Regulation | Gene Symbol | Description | Genbank Accession |
|---|---|---|---|---|---|
| | | | | (GB: CAO15763.1); similar to hypothetical protein [*Vitis vinifera*] (GB: CAN72579.1); contains InterPro domain Protein of unknown function DUF246, plant (InterPro: IPR004348) [AT2G37980.1] | |
| A_84_P786490 | 2.35 | down | WRKY46 | WRKY46 (WRKY DNA-binding protein 46); transcription factor [AT2G46400.1] | NM_130204 |
| A_84_P21970 | 2.55 | down | AT2G22200 | AP2 domain-containing transcription factor [AT2G22200.1] | NM_127788 |
| A_84_P20728 | 1.67 | down | ABR1 | ABR1 (ABA REPRESSOR1); DNA binding/transcription factor [AT5G64750.1] | NM_125871 |
| A_84_P809469 | 1.61 | down | | | |
| A_84_P594936 | 2.77 | down | CYP707A3 | CYP707A3 (cytochrome P450, family 707, subfamily A, polypeptide 3); oxygen binding [AT5G45340.2] | NM_123902 |
| A_84_P18908 | 3.30 | down | AT1G33760 | AP2 domain-containing transcription factor, putative [AT1G33760.1] | NM_103095 |
| A_84_P838689 | 1.76 | down | ATGSTU17/ERD9/GST30/GST30B | ATGSTU17/ERD9/GST30/GST30B (EARLY-RESPONSIVE TO DEHYDRATION 9); glutathione transferase [AT1G10370.1] | NM_100911 |
| A_84_P709533 | 4.33 | down | DVL10/RTFL12 | DVL10/RTFL12 (*ROTUNDIFOLIA* LIKE 12) [AT4G13395.1] | NM_001084915 |
| A_84_P17328 | 3.38 | down | AT2G39350 | ABC transporter family protein [AT2G39350.1] | NM_129492 |
| A_84_P752539 | 1.54 | down | AT1G08920 | sugar transporter, putative [AT1G08920.2] | NM_001035928 |
| A_84_P592444 | 2.07 | down | AT1G19200 | senescence-associated protein-related [AT1G19200.1] | NM_101778 |
| A_84_P12056 | 2.95 | down | AT5G08030 | glycerophosphoryl diester phosphodiesterase family protein [AT5G08030.1] | NM_120885 |
| A_84_P853187 | 1.51 | down | AT4G34150 | C2 domain-containing protein [AT4G34150.1] | NM_119578 |
| A_84_P519070 | 1.5971 | down | AT3G15750 | similar to unknown protein [*Arabidopsis thaliana*] (TAIR: AT1G34570.1); similar to hypothetical protein [*Lotus japonicus*] (GB: CAE45590.1); contains domain YJ37_YEAST_P47118; (PD086192) [AT3G15750.1] | NM_112445 |
| A_84_P18072 | 2.52 | down | AT1G72520 | lipoxygenase, putative [AT1G72520.1] | NM_105911 |
| A_84_P22489 | 1.64 | down | AT5G22250 | CCR4-NOT transcription complex protein, putative [AT5G22250.1] | NM_122130 |
| A_84_P786098 | 2.38 | down | AT1G32920 | 07-E012992-019-004-M01-SP6r MPIZ-ADIS-019 *Arabidopsis thaliana* cDNA clone MPIZp768M014Q 3-PRIME, mRNA sequence [CB253198] | |
| A_84_P808596 | 2.16 | down | AT4G20860 | FAD-binding domain-containing protein [AT4G20860.1] | NM_118204 |
| A_84_P587419 | 9.99 | down | IPS1 | IPS1 (INDUCED BY PHOSPHATE STARVATION1) [AT3G09922.1] | NM_180219 |
| A_84_P12638 | 2.95 | down | AT3G08860 | alanine--glyoxylate aminotransferase, putative/beta-alanine-pyruvate aminotransferase, putative/AGT, putative [AT3G08860.1] | NM_111720 |
| A_84_P805550 | 2.23 | down | AT1G17620 | AV799745 RAFL9 *Arabidopsis thaliana* cDNA clone RAFL09-21-E24 3', mRNA sequence [AV799745] | |
| A_84_P242895 | 1.74 | down | AT1G66160 | U-box domain-containing protein [AT1G66160.1] | NM_105287 |
| A_84_P11431 | 1.73 | down | ATGSTU24 | ATGSTU24 (*ARABIDOPSIS THALIANA* GLUTATHIONE S-TRANSFERASE (CLASS TAU) 24); glutathione transferase [AT1G17170.1] | NM_101578 |
| A_84_P23396 | 1.59 | down | NHL3 | NHL3 (NDR1/HIN1-like 3) [AT5G06320.1] | NM_120715 |
| A_84_P835781 | 2.13 | down | AT2G17660 | nitrate-responsive NOI protein, putative [AT2G17660.1] | NM_127320 |
| A_84_P844786 | 1.84 | down | AT2G16890 | UDP-glucoronosyl/UDP-glucosyl transferase family protein [AT2G16890.2] | NM_127242 |
| A_84_P137739 | 1.88 | down | EDL3 | EDL3 (EID1-LIKE 3) [AT3G63060.1] | NM_116171 |
| A_84_P801239 | 1.64 | down | ATGSTF7 | AV441238 *Arabidopsis thaliana* above-ground organ two to six-week old *Arabidopsis thaliana* cDNA clone APZ36c02_f 3', mRNA sequence [AV441238] | |
| A_84_P820040 | 1.57 | down | PLP2 | PLP2 (PHOSPHOLIPASE A 2A); nutrient reservoir [AT2G26560.1] | NM_128213 |
| A_84_P18989 | 3.12 | down | ATMC8 | ATMC8 (METACASPASE 8); caspase [AT1G16420.1] | NM_101508 |
| A_84_P136725 | 1.9322 | down | AT5G36920 | similar to unknown protein [*Arabidopsis thaliana*] (TAIR: AT5G36925.1) [AT5G36920.1] | NM_123050 |
| A_84_P787625 | 2.58 | down | AT4G13900 | pseudogene, similar to NL0D, contains leucine rich-repeat domains Pfam: PF00560, INTERPRO: IPR001611; similar to Cf-4A protein (*Lycopersicon esculentum*) gi [AT4G13900.1] | |
| A_84_P729644 | 6.93 | down | | *Arabidopsis thaliana* At4-2 mRNA, complete sequence [AY334555] | |
| A_84_P22924 | 2.94 | down | AT2G47550 | pectinesterase family protein [AT2G47550.1] | NM_130323 |
| A_84_P293214 | 1.67 | down | YSL8 | YSL8 (YELLOW STRIPE LIKE 8); oligopeptide transporter [AT1G48370.1] | NM_103733 |
| A_84_P12844 | 1.8195 | down | AT4G08630 | similar to unknown protein [*Arabidopsis thaliana*] (TAIR: AT3G48860.2); similar to unnamed protein | NM_116932 |

TABLE 6-continued

List of Genes Responsive to T1 Treatment

| ProbeName | Fold change | Regulation | Gene Symbol | Description | Genbank Accession |
|---|---|---|---|---|---|
| | | | | product [*Vitis vinifera*] (GB: CAO68373.1); similar to Os01g0928100 [*Oryza sativa* (*japonica* cultivar-group)] (GB: NP_001045273.1) [AT4G08630.1] | |
| A_84_P18566 | 2.20 | down | AT4G24570 | mitochondrial substrate carrier family protein [AT4G24570.1] | NM_118590 |
| A_84_P793960 | 2.55 | down | AT1G08920 | AV806945 RAFL9 *Arabidopsis thaliana* cDNA clone RAFL09-48-110 3', mRNA sequence [AV806945] | |
| A_84_P286390 | 3.42 | down | AOC3 | AOC3 (ALLENE OXIDE CYCLASE 3) [AT3G25780.1] | NM_113477 |
| A_84_P756338 | 1.92 | down | AT2G07692 | Identical to Uncharacterized mitochondrial protein AtMg01300 [*Arabidopsis Thaliana*] (GB: P92561; GB: Q1ZXV7; GB: Q8S893) [AT2G07692.1] | NM_126743 |
| A_84_P228049 | 1.52 | down | BT1 | BT1 (BTB and TAZ domain protein 1); protein binding/ transcription regulator [AT5G63160.1] | NM_125711 |
| A_84_P21219 | 1.62 | down | AZF2 | AZF2 (*ARABIDOPSIS* ZINC-FINGER PROTEIN 2); nucleic acid binding/transcription factor/zinc ion binding [AT3G19580.1] | NM_112848 |
| A_84_P611898 | 6.03 | down | AT5G59580 | UDP-glucoronosyl/UDP-glucosyl transferase family protein [AT5G59580.1] | NM_125350 |
| A_84_P68014 | 1.56 | down | AT4G34150 | C2 domain-containing protein [AT4G34150.1] | NM_119578 |
| A_84_P833745 | 2.24 | down | | | |
| A_84_P20482 | 2.61 | down | CKX4 | CKX4 (CYTOKININ OXIDASE 4); cytokinin dehydrogenase [AT4G29740.1] | NM_179139 |
| A_84_P21159 | 1.68 | down | AT3G04010 | glycosyl hydrolase family 17 protein [AT3G04010.1] | NM_111272 |
| A_84_P755281 | 1.59 | down | AT2G05050 | pseudogene, protein phosphatase 2C, blastp match of 65% identity and 8.1e−74 P-value to GP [AT2G05050.1] | NM_113628 |
| A_84_P752862 | 2.18 | down | AT1G51802 | Encodes a defensin-like (DEFL) family protein. [AT1G51802.1] | |
| A_84_P609053 | 1.86 | down | ATGPAT7/GPAT7 | ATGPAT7/GPAT7 (GLYCEROL-3-PHOSPHATE ACYLTRANSFERASE 7); 1-acylglycerol-3-phosphate O-acyltransferase/acyltransferase [AT5G06090.1] | NM_120691 |
| A_84_P92299 | 4.57 | down | AT1G73010 | phosphoric monoester hydrolase [AT1G73010.1] | NM_105959 |
| A_84_P15531 | 1.52 | down | AT3G26500 | leucine-rich repeat family protein [AT3G26500.1] | NM_113557 |
| A_84_P23919 | 3.56 | down | YLS9 | YLS9 (YELLOW-LEAF-SPECIFIC GENE 9) [AT2G35980.1] | NM_129157 |
| A_84_P823530 | 1.72 | down | JMT | JMT (JASMONIC ACID CARBOXYL METHYLTRANSFERASE); jasmonate O-methyltransferase [AT1G19640.1] | NM_101820 |
| A_84_P797066 | 2.40 | down | | AYAFD87TR pooled cDNA populations *Arabidopsis thaliana* cDNA, mRNA sequence [EG438208] | |
| A_84_P602531 | 13.91 | down | ATPAP14/PAP14 | ATPAP14/PAP14; acid phosphatase/protein serine/threonine phosphatase [AT2G46880.1] | NM_201975 |
| A_84_P13913 | 1.5707 | down | AT1G19380 | similar to unknown protein [*Arabidopsis thaliana*] (TAIR: AT5G65650.1); similar to unknown [*Vitis pseudoreticulata*] (GB: ABC69762.1); similar to unnamed protein product [*Vitis vinifera*] (GB: CAO61173.1); contains InterPro domain Protein of unknown function DUF1195 (InterPro: IPR010608) [AT1G19380.1] | NM_101795 |
| A_84_P814230 | 1.60 | down | AT2G22500 | mitochondrial substrate carrier family protein [AT2G22500.1] | NM_127816 |
| A_84_P262200 | 2.14 | down | AT5G43420 | zinc finger (C3HC4-type RING finger) family protein [AT5G43420.1] | NM_123708 |
| A_84_P13151 | 1.65 | down | AT5G61820 | similar to MtN19-like protein [*Pisum sativum*] (GB: AAU14999.2); contains InterPro domain Stress up-regulated Nod 19 (InterPro: IPR011692) [AT5G61820.1] | NM_125576 |
| A_84_P259470 | 2.71 | down | AT1G61890 | MATE efflux family protein [AT1G61890.1] | NM_104870 |
| A_84_P14928 | 3.23 | down | SQP2 | SQP2 (Squalene monooxygenase 2); oxidoreductase [AT5G24140.1] | NM_122319 |
| A_84_P23526 | 2.07 | down | MAPKKK15 | MAPKKK15 (Mitogen-activated protein kinase kinase kinase 15); kinase [AT5G55090.1] | NM_124891 |
| A_84_P10209 | 1.73 | down | AT5G25930 | leucine-rich repeat family protein/protein kinase family protein [AT5G25930.1] | NM_122494 |
| A_84_P832842 | 1.60 | down | AT4G13800 | permease-related [AT4G13800.1] | NM_117454 |
| A_84_P15863 | 1.57 | down | ANAC087 | ANAC087; transcription factor [AT5G18270.1] | NM_121832 |
| A_84_P20128 | 1.55 | down | ST | ST (steroid sulfotransferase); sulfotransferase [AT2G03760.1] | NM_126423 |
| A_84_P181994 | 2.10 | down | SRG3 | SRG3 (SENESCENCE-RELATED GENE 3); glycerophosphodiester phosphodiesterase [AT3G02040.1] | NM_111070 |
| A_84_P16606 | 1.73 | down | WRKY22 | WRKY22 (WRKY DNA-binding protein 22); transcription factor [AT4G01250.1] | NM_116355 |
| A_84_P288954 | 2.67 | down | AT2G03020 | heat shock protein-related [AT2G03020.1] | NM_201679 |

TABLE 6-continued

List of Genes Responsive to T1 Treatment

| ProbeName | Fold change | Regulation | Gene Symbol | Description | Genbank Accession |
|---|---|---|---|---|---|
| A_84_P528434 | 1.83 | down | AT5G56960 | basic helix-loop-helix (bHLH) family protein [AT5G56960.1] | NM_125078 |
| A_84_P229729 | 1.91 | down | AT2G20142 | transmembrane receptor [AT2G20142.1] | NM_201758 |
| A_84_P820417 | 1.61 | down | ATERF6 | ATERF6 (ETHYLENE RESPONSIVE ELEMENT BINDING FACTOR 6); DNA binding/transcription factor [AT4G17490.1] | NM_117854 |
| A_84_P11771 | 1.88 | down | AT3G22930 | calmodulin, putative [AT3G22930.1] | NM_113193 |
| A_84_P15329 | 1.9615 | down | AT2G40000 | similar to unknown protein [Arabidopsis thaliana] (TAIR: AT3G55840.1); similar to unnamed protein product [Vitis vinifera] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] | NM_129558 |
| A_84_P538729 | 38.4 | down | AT4G10290 | similar to unknown protein [Arabidopsis thaliana] (TAIR: AT4G10280.1); similar to unnamed protein product [Vitis vinifera] (GB: CAO44489.1); contains InterPro domain RmlC-like jelly roll fold (InterPro: IPR014710); contains InterPro domain Protein of unknown function DUF861, cupin-3 (InterPro: IPR008579); contains InterPro domain Cupin, RmlC-type (InterPro: IPR011051) [AT4G10290.1] | NM_117097 |
| A_84_P16097 | 1.60 | down | AT1G24140 | matrixin family protein [AT1G24140.1] | NM_102260 |
| A_84_P261020 | 1.55 | down | ATPAP16/PAP16 | ATPAP16/PAP16 (purple acid phosphatase 16); acid phosphatase/protein serine/threonine phosphatase [AT3G10150.1] | NM_111850 |
| A_84_P842252 | 1.61 | down | JMT | JMT (JASMONIC ACID CARBOXYL METHYLTRANSFERASE); jasmonate O-methyltransferase [AT1G19640.1] | NM_101820 |
| A_84_P598642 | 1.83 | down | AT1G07135 | glycine-rich protein [AT1G07135.1] | NM_100587 |
| A_84_P15123 | 3.18 | down | AT1G02310 | glycosyl hydrolase family protein 5/cellulase family protein/(1-4)-beta-mannan endohydrolase, putative [AT1G02310.1] | NM_100112 |
| A_84_P15741 | 3.11 | down | AT4G27280 | calcium-binding EF hand family protein [AT4G27280.1] | NM_118862 |
| A_84_P11802 | 1.77 | down | AT3G46690 | UDP-glucoronosyl/UDP-glucosyl transferase family protein [AT3G46690.1] | NM_114536 |
| A_84_P19581 | 8.04 | down | AT4G15200 | formin homology 2 domain-containing protein/FH2 domain-containing protein [AT4G15200.1] | NM_117608 |
| A_84_P833808 | 2.71 | down | LOX3 | LOX3 (Lipoxygenase 3); iron ion binding/lipoxygenase/metal ion binding/oxidoreductase, acting on single donors with incorporation of molecular oxygen, incorporation of two atoms of oxygen [AT1G17420.1] | NM_101603 |
| A_84_P18158 | 2.03 | down | AT1G57850 | Toll-Interleukin-Resistance (TIR) domain-containing protein [AT1G57850.1] | NM_104578 |
| A_84_P828148 | 3.59 | down | | NM_128773 transmembrane receptor {Arabidopsis thaliana} (exp = −1; wgp = 0; cg = 0), partial (42%) [TC299475] | |
| A_84_P762569 | 7.01 | down | AT3G27809 | unknown protein [AT3G27809.1] | NM_001125249 |
| A_84_P554567 | 1.90 | down | GATL10 | GATL10 (Galacturonosyltransferase-like 10); polygalacturonate 4-alpha-galacturonosyltransferase/transferase, transferring hexosyl groups [AT3G28340.1] | NM_113753 |
| A_84_P802987 | 1.8842 | down | AT2G40000 | similar to unknown protein [Arabidopsis thaliana] (TAIR: AT3G55840.1); similar to unnamed protein product [Vitis vinifera] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] | NM_129558 |
| A_84_P750962 | 1.52 | down | AtRABA6b | AtRABA6b (Arabidopsis Rab GTPase homolog A6b); GTP binding [AT1G18200.1] | NM_101680 |
| A_84_P21529 | 1.75 | down | TBP1 | TBP1 (TELOMERIC DNA BINDING PROTEIN 1); DNA binding [AT5G13820.1] | NM_121385 |
| A_84_P813646 | 1.76 | down | AR781 | AR781 [AT2G26530.1] | NM_128210 |
| A_84_P726784 | 1.56 | down | AT4G36648 | other RNA [AT4G36648.1] | NR_023054 |
| A_84_P769350 | 2.45 | down | AT5G54165 | unknown protein [AT5G54165.1] | NM_001125962 |
| A_84_P54170 | 1.78 | down | AT3G57450 | similar to unnamed protein product [Vitis vinifera] (GB: CAO40798.1) [AT3G57450.1] | NM_115605 |
| A_84_P17313 | 4.05 | down | AT2G37770 | aldo/keto reductase family protein [AT2G37770.1] | NM_001036428 |
| A_84_P846967 | 1.61 | down | AT5G53050 | hydrolase, alpha/beta fold family protein [AT5G53050.1] | NM_124684 |

TABLE 6-continued

List of Genes Responsive to T1 Treatment

| ProbeName | Fold change | Regulation | Gene Symbol | Description | Genbank Accession |
|---|---|---|---|---|---|
| A_84_P305850 | 2.09 | down | GAD4 | GAD4 (GLUTAMATE DECARBOXYLASE 4); calmodulin binding [AT2G02010.1] | NM_126262 |
| A_84_P784788 | 1.50 | down | AT5G17000 | NADP-dependent oxidoreductase, putative [AT5G17000.1] | NM_121706 |
| A_84_P16108 | 1.57 | down | HEMA2 | HEMA2; glutamyl-tRNA reductase [AT1G09940.1] | NM_100868 |
| A_84_P13172 | 3.58 | down | MAPKKK19 | MAPKKK19 (Mitogen-activated protein kinase kinase kinase 19); kinase [AT5G67080.1] | NM_126108 |
| A_84_P163133 | 2.0176 | down | AT1G67600 | similar to catalytic [*Arabidopsis thaliana*] (TAIR: AT1G24350.1); similar to unknown [*Picea sitchensis*] (GB: ABK26930.1); contains InterPro domain Acid phosphatase/vanadium-dependent haloperoxidase related (InterPro: IPR003832) [AT1G67600.1] | NM_105427 |
| A_84_P14274 | 4.95 | down | AT1G52690 | late embryogenesis abundant protein, putative/LEA protein, putative [AT1G52690.1] | NM_202280 |
| A_84_P14505 | 3.42 | down | AT2G32140 | transmembrane receptor [AT2G32140.1] | NM_128773 |
| A_84_P818437 | 4.95 | down | CML37/CML39 | CML37/CML39; calcium ion binding [AT5G42380.1] | NM_123603 |
| A_84_P18557 | 3.14 | down | AT4G22470 | protease inhibitor/seed storage/lipid transfer protein NM_118373 (LTP) family protein [AT4G22470.1] | |
| A_84_P12934 | 1.64 | down | AT4G33920 | protein phosphatase 2C family protein/PP2C family protein [AT4G33920.1] | NM_119551 |
| A_84_P97916 | 3.8377 | down | AT4G29780 | similar to unknown protein [*Arabidopsis thaliana*] (TAIR: AT5G12010.1); similar to unnamed protein product [*Vitis vinifera*] (GB: CAO43835.1); contains domain PTHR22930 (PTHR22930) [AT4G29780.1] | NM_119124 |
| A_84_P178234 | 1.66 | down | AT4G13800 | permease-related [AT4G13800.1] | NM_117454 |
| A_84_P21400 | 3.77 | down | ATCHX17 | ATCHX17 (CATION/H+ EXCHANGER 17); monovalent cation: proton antiporter [AT4G23700.1] | NM_118501 |
| A_84_P787776 | 1.80 | down | AT3G56260 | unknown protein [AT3G56260.1] | NM_115484 |
| A_84_P22597 | 1.59 | down | AT5G59550 | zinc finger (C3HC4-type RING finger) family protein [AT5G59550.1] | NM_125347 |
| A_84_P851247 | 10.71 | down | AT5G28237 | tryptophan synthase, beta subunit, putative [AT5G28237.1] | NM_203115 |
| A_84_P801093 | 1.62 | down | TCH2 | TCH2 (TOUCH 2); calcium ion binding [AT5G37770.1] | NM_123136 |
| A_84_P21595 | 2.43 | down | AT5G44360 | FAD-binding domain-containing protein [AT5G44360.1] | NM_123803 |
| A_84_P23347 | 1.87 | down | AT4G36010 | pathogenesis-related thaumatin family protein [AT4G36010.1] | NM_001036715 |
| A_84_P18640 | 7.37 | down | ATCSLA01 | ATCSLA01 (Cellulose synthase-like A1); glucosyltransferase/transferase, transferring glycosyl groups [AT4G16590.1] | NM_117760 |
| A_84_P606233 | 1.88 | down | AT3G56260 | unknown protein [AT3G56260.1] | NM_115484 |
| A_84_P830329 | 1.97 | down | AT5G43420 | zinc finger (C3HC4-type RING finger) family protein [AT5G43420.1] | NM_123708 |
| A_84_P790863 | 2.22 | down | AT5G64700 | nodulin MtN21 family protein [AT5G64700.1] | NM_125866 |
| A_84_P11388 | 1.7051 | down | AT1G05340 | similar to unknown protein [*Arabidopsis thaliana*] (TAIR: AT2G32210.1) [AT1G05340.1] | NM_100413 |
| A_84_P10433 | 1.79 | down | ATFH8 | ATFH8 (FORMIN 8); actin binding/actin filament binding/profilin binding [AT1G70140.1] | NM_105682 |
| A_84_P787949 | 1.9077 | down | AT2G46150 | similar to unknown protein [*Arabidopsis thaliana*] (TAIR: AT3G54200.1); similar to plant cell wall protein SITFR88 [*Lycopersicon esculentum*] (GB: ABF39005.1); contains InterPro domain Harpin-induced 1 (InterPro: IPR010847) [AT2G46150.1] | NM_130177 |
| A_84_P141659 | 2.2467 | down | AT4G01360 | similar to BPS1 (BYPASS 1) [*Arabidopsis thaliana*] (TAIR: AT1G01550.2); similar to BPS1 (BYPASS 1) [*Arabidopsis thaliana*] (TAIR: AT1G01550.1); similar to unknown [*Populus trichocarpa*] (GB: ABK94247.1) [AT4G01360.1] | NM_116366 |
| A_84_P18836 | 2.82 | down | AT5G64700 | nodulin MtN21 family protein [AT5G64700.1] | NM_125866 |
| A_84_P17388 | 1.70 | down | AT3G06500 | beta-fructofuranosidase, putative/invertase, putative/ saccharase, putative/beta-fructosidase, putative [AT3G06500.1] | NM_111526 |
| A_84_P19838 | 2.08 | down | AT1G15415 | The protein encoded by this gene was identified as a part of pollen proteome by mass spec analysis. It has weak homology to LEA (late embryo abundant) proteins. [AT1G15415.1] | NM_101411 |
| A_84_P16214 | 1.58 | down | AT1G70800 | C2 domain-containing protein [AT1G70800.1] | NM_105748 |
| A_84_P10932 | 1.62 | down | TMP-C | TMP-C (PLASMA MEMBRANE INTRINSIC PROTEIN 1; 4); water channel [AT4G00430.1] | NM_202760 |
| A_84_P17111 | 1.54 | down | AT1G02820 | late embryogenesis abundant 3 family protein/LEA3 family protein [AT1G02820.1] | NM_100163 |
| A_84_P582920 | 2.88 | down | BAP2 | BAP2 (BON ASSOCIATION PROTEIN 2) [AT2G45760.1] | NM_130139 |

TABLE 6-continued

List of Genes Responsive to T1 Treatment

| ProbeName | Fold change | Regulation | Gene Symbol | Description | Genbank Accession |
|---|---|---|---|---|---|
| A_84_P528136 | 1.68 | down | CRK11 | CRK11 (CYSTEINE-RICH RLK11); kinase [AT4G23190.1] | NM_118448 |
| A_84_P715787 | 1.5534 | down | AT1G32928 | similar to unknown protein [*Arabidopsis thaliana*] (TAIR: AT1G32920.1) [AT1G32928.1] | NM_001036055 |
| A_84_P17614 | 3.03 | down | CRK13/HIG1 | CRK13/HIG1; kinase [AT4G23210.1] | NM_001084966 |
| A_84_P13726 | 1.85 | down | ATEP3 | ATEP3 (*Arabidopsis thaliana* chitinase class IV); chitinase [AT3G54420.1] | NM_115302 |
| A_84_P763881 | 1.58 | down | AT4G20830 | FAD-binding domain-containing protein [AT4G20830.1] | NM_202851 |
| A_84_P264050 | 3.84 | down | AT1G08310 | esterase/lipase/thioesterase family protein [AT1G08310.1] | NM_001084019 |
| A_84_P22532 | 1.57 | down | AT5G41740 | disease resistance protein (TIR-NBS-LRR class), putative [AT5G41740.1] | NM_123539 |
| A_84_P10613 | 2.29 | down | COR15B | COR15B [AT2G42530.1] | NM_129814 |
| A_84_P752940 | 2.19 | down | AT1G13608 | Encodes a defensin-like (DEFL) family protein. [AT1G13608.1] | NM_001035963 |
| A_84_P603414 | 1.5285 | down | AT2G46940 | similar to unknown protein [*Arabidopsis thaliana*] (TAIR: AT3G62070.1); similar to hypothetical protein [*Vitis vinifera*] (GB: CAN75643.1) [AT2G46940.1] | NM_130262 |
| A_84_P762652 | 1.6629 | down | AT3G27329 | similar to unknown protein [*Arabidopsis thaliana*] (TAIR: AT3G27331.1); contains InterPro domain Plant self-incompatibility S1 (InterPro: IPR010264) [AT3G27329.1] | NM_001125245 |
| A_84_P16077 | 2.83 | down | MAPKKK18 | MAPKKK18 (Mitogen-activated protein kinase kinase kinase 18); kinase [AT1G05100.1] | NM_100389 |
| A_84_P816512 | 1.6545 | down | AT2G18690 | similar to unknown protein [*Arabidopsis thaliana*] (TAIR: AT2G18680.1); similar to hypothetical protein OsI_029427 [*Oryza sativa* (indica cultivar-group)] (GB: EAZ08195.1) [AT2G18690.1] | NM_127425 |
| A_84_P76184 | 1.65 | down | WRKY30 | WRKY30 (WRKY DNA-binding protein 30); transcription factor [AT5G24110.1] | NM_122316 |
| A_84_P22854 | 1.65 | down | AT1G51790 | kinase [AT1G51790.1] | NM_104058 |
| A_84_P23014 | 4.04 | down | AT2G44581 | protein binding/zinc ion binding [AT2G44581.1] | NM_001125054 |
| A_84_P19389 | 1.58 | down | AT3G52450 | U-box domain-containing protein [AT3G52450.1] | NM_115105 |
| A_84_P786969 | 4.33 | down | ANAC019 | *Arabidopsis thaliana* Full-length cDNA Complete sequence from clone GSLTFB14ZF09 of Flowers and buds of strain col-0 of *Arabidopsis thaliana* (thale cress) [BX813389] | |
| A_84_P785537 | 1.5503 | down | AT5G40460 | similar to unknown protein [*Arabidopsis thaliana*] (TAIR: AT3G27630.1); similar to hypothetical protein [*Vitis vinifera*] (GB: CAN59885.1) [AT5G40460.1] | NM_123410 |
| A_84_P819307 | 1.84 | down | AT2G43590 | chitinase, putative [AT2G43590.1] | NM_129921 |
| A_84_P765683 | 2.25 | down | AT4G23215 | pseudogene of cysteine-rich receptor-like protein kinase family protein [AT4G23215.1] | |
| A_84_P148418 | 2.60 | down | MT1C | MT1C (metallothionein 1C) [AT1G07610.1] | NM_100634 |
| A_84_P762507 | 5.62 | down | AT3G25573 | unknown protein [AT3G25573.1] | NM_001125226 |
| A_84_P784916 | 2.00 | down | ATGSTU17/ERD9/GST30/GST30B | ATGSTU17/ERD9/GST30/GST30B (EARLY-RESPONSIVE TO DEHYDRATION 9); glutathione transferase [AT1G10370.1] | NM_100911 |
| A_84_P826766 | 1.67 | down | AT5G58680 | armadillo/beta-catenin repeat family protein [AT5G58680.1] | NM_125255 |
| A_84_P16137 | 2.5341 | down | AT1G10530 | similar to unknown protein [*Arabidopsis thaliana*] (TAIR: AT1G60010.1); similar to unnamed protein product [*Vitis vinifera*] (GB: CAO40951.1) [AT1G10530.1] | NM_100928 |
| A_84_P19923 | 1.68 | down | AT1G05680 | UDP-glucoronosyl/UDP-glucosyl transferase family protein [AT1G05680.1] | NM_100448 |
| A_84_P23380 | 1.72 | down | AT5G01540 | lectin protein kinase, putative [AT5G01540.1] | NM_120232 |
| A_84_P209868 | 3.01 | down | AT2G32130 | similar to UNE1 (unfertilized embryo sac 1) [*Arabidopsis thaliana*] (TAIR: AT1G29300.1); similar to unnamed protein product [*Vitis vinifera*] (GB: CAO48018.1); contains InterPro domain Protein of unknown function DUF641, plant (InterPro: IPR006943) [AT2G32130.1] | NM_128772 |
| A_84_P18553 | 1.89 | down | B120 | B120; protein kinase/sugar binding [AT4G21390.1] | NM_118259 |
| A_84_P168493 | 1.72 | down | AT3G46620 | zinc finger (C3HC4-type RING finger) family protein [AT3G46620.1] | NM_114529 |
| A_84_P862479 | 4.52 | down | | | |
| A_84_P787940 | 9.41 | down | ATPAP14/PAP14 | ATPAP14/PAP14; protein serine/threonine phosphatase [AT2G46880.2] | NM_201975 |
| A_84_P206968 | 1.61 | down | ATPUP18 | ATPUP18 (*Arabidopsis thaliana* purine permease 18); purine transmembrane transporter [AT1G57990.1] | NM_104584 |
| A_84_P21889 | 1.83 | down | AT1G74360 | leucine-rich repeat transmembrane protein kinase, putative [AT1G74360.1] | NM_106096 |
| A_84_P757973 | 3.44 | down | AT2G44578 | protein binding/zinc ion binding [AT2G44578.1] | NM_001084589 |

TABLE 6-continued

List of Genes Responsive to T1 Treatment

| ProbeName | Fold change | Regulation | Gene Symbol | Description | Genbank Accession |
|---|---|---|---|---|---|
| A_84_P18211 | 1.78 | down | AR781 | AR781 [AT2G26530.1] | NM_128210 |
| A_84_P11369 | 3.7375 | down | AT1G23110 | similar to unknown protein [*Arabidopsis thaliana*] (TAIR: AT1G70900.1); similar to hypothetical protein [*Vitis vinifera*] (GB: CAN77015.1) [AT1G23110.1] | NM_001123865 |
| A_84_P828117 | 1.70 | down | AT1G72120 | transporter [AT1G72120.1] | NM_105870 |
| A_84_P24102 | 1.57 | down | AT3G48460 | GDSL-motif lipase/hydrolase family protein [AT3G48460.1] | NM_114705 |
| A_84_P17343 | 4.33 | down | ATERF13/EREBP | ATERF13/EREBP (ETHYLENE-RESPONSIVE ELEMENT BINDING FACTOR 13); DNA binding/ transcription factor [AT2G44840.1] | NM_130048 |
| A_84_P761749 | 7.08 | down | AT3G22275 | similar to unnamed protein product [*Vitis vinifera*] (GB: CAO40332.1); contains domain PROKAR_LIPOPROTEIN (PS51257) [AT3G22275.1] | NM_001084731 |
| A_84_P847162 | 11.06 | down | ATTPS03 | ATTPS03 (*Arabidopsis thaliana* terpene synthase 03) [AT4G16740.2] | NM_001036574 |
| A_84_P11694 | 3.62 | down | AT3G01830 | calmodulin-related protein, putative [AT3G01830.1] | NM_111049 |
| A_84_P793106 | 3.19 | down | AT3G55980 | AV536167 *Arabidopsis thaliana* liquid-cultured seedlings Columbia *Arabidopsis thaliana* cDNA clone pAZNII0193F 3', mRNA sequence [AV536167] | |
| A_84_P217688 | 2.1498 | down | AT1G76600 | similar to unknown protein [*Arabidopsis thaliana*] (TAIR: AT1G21010.1); similar to hypothetical protein [*Vitis vinifera*] (GB: CAN67638.1) [AT1G76600.1] | NM_106310 |
| A_84_P23913 | 1.76 | down | AT2G38870 | protease inhibitor, putative [AT2G38870.1] | NM_129444 |
| A_84_P849049 | 2.30 | down | | NM_113740 PMZ {*Arabidopsis thaliana*} (exp = −1; wgp = 0; cg = 0), partial (76%) [TC302412] | |
| A_84_P557120 | 2.04 | down | AT2G43960 | SWAP (Suppressor-of-White-APricot)/surp domain-containing protein [AT2G43960.1] | NM_129958 |
| A_84_P558934 | 1.74 | down | AT3G12910 | transcription factor [AT3G12910.1] | NM_112127 |
| A_84_P22181 | 2.28 | down | PMZ | PMZ; zinc ion binding [AT3G28210.1] | NM_113740 |
| A_84_P762988 | 6.79 | down | MAPKKK21 | MAPKKK21; ATP binding/protein kinase [AT4G36950.1] | NM_001085035 |
| A_84_P769008 | 1.88 | down | AT5G37351 | unknown protein [AT5G37351.1] | NM_001125850 |
| A_84_P813986 | 1.68 | down | | | |
| A_84_P799503 | 2.06 | down | AT1G20740 | *Arabidopsis thaliana* Full-length cDNA Complete sequence from clone GSLTPGH93ZD01 of Hormone Treated Callus of strain col-0 of *Arabidopsis thaliana* (thale cress) [BX817216] | |
| A_84_P279580 | 2.291 | down | AT3G50800 | similar to unknown protein [*Arabidopsis thaliana*] (TAIR: AT5G66580.1); similar to unnamed protein product [*Vitis vinifera*] (GB: CAO41608.1); similar to unnamed protein product [*Vitis vinifera*] (GB: CAO45438.1); similar to hypothetical protein [*Vitis vinifera*] (GB: CAN61825.1) [AT3G50800.1] | NM_114940 |
| A_84_P600694 | 1.9143 | down | AT2G30900 | similar to unknown protein [*Arabidopsis thaliana*] (TAIR: AT2G42570.1); similar to unnamed protein product [*Vitis vinifera*] (GB: CAO69941.1); contains InterPro domain Protein of unknown function DUF231, plant (InterPro: IPR004253) [AT2G30900.1] | NM_128642 |
| A_84_P557122 | 3.91 | down | AT2G45130 | SPX (SYG1/Pho81/XPR1) domain-containing protein [AT2G45130.1] | NM_130076 |
| A_84_P828432 | 1.593 | down | AT1G58280 | similar to unknown protein [*Arabidopsis thaliana*] (TAIR: AT5G64460.6); similar to unknown protein [*Arabidopsis thaliana*] (TAIR: AT5G64460.4); similar to unknown protein [*Arabidopsis thaliana*] (TAIR: AT5G64460.3); similar to hypothetical protein [*Vitis vinifera*] (GB: CAN70041.1); contains InterPro domain Phosphoglycerate mutase (InterPro: IPR013078) [AT1G58280.2] | NM_179495 |
| A_84_P844006 | 3.39 | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] | NM_179772 |
| A_84_P840456 | 2.22 | down | | GB | |
| A_84_P19210 | 2.17 | down | WRKY46 | WRKY46 (WRKY DNA-binding protein 46); transcription factor [AT2G46400.1] | NM_130204 |
| A_84_P224809 | 2.06 | down | AT2G38790 | unknown protein [AT2G38790.1] | NM_129436 |
| A_84_P16803 | 1.78 | down | AT5G14700 | cinnamoyl-CoA reductase-related [AT5G14700.1] | NM_121474 |
| A_84_P17310 | 8.63 | down | AT2G30830 | 2-oxoglutarate-dependent dioxygenase, putative [AT2G30830.1] | NM_128636 |
| A_84_P602187 | 1.71 | down | AT1G05575 | unknown protein [AT1G05575.1] | NM_100437 |
| A_84_P851376 | 3.13 | down | | AB000875 RD22BP1 {*Arabidopsis thaliana*} (exp = −1; wgp = 0; cg = 0), partial (30%) [TC306284] | |
| A_84_P245475 | 2.9726 | down | AT2G25460 | similar to unknown protein [*Arabidopsis thaliana*] (TAIR: AT5G04860.1); similar to hypothetical protein [*Vitis vinifera*] (GB: CAN68625.1); contains InterPro | NM_128103 |

TABLE 6-continued

List of Genes Responsive to T1 Treatment

| ProbeName | Fold change | Regulation | Gene Symbol | Description | Genbank Accession |
|---|---|---|---|---|---|
| | | | | domain C2 calcium-dependent membrane targeting (InterPro: IPR000008) [AT2G25460.1] | |
| A_84_P19550 | 1.54 | down | SQD1 | SQD1 (sulfoquinovosyldiacylglycerol 1); UDPsulfoquinovose synthase [AT4G33030.1] | NM_119457 |
| A_84_P765048 | 5.68 | down | AT4G33467 | unknown protein [AT4G33467.1] | NM_001085016 |
| A_84_P817566 | 4.22 | down | AT1G73010 | phosphoric monoester hydrolase [AT1G73010.1] | NM_105959 |
| A_84_P16848 | 1.58 | down | AT5G39580 | peroxidase, putative [AT5G39580.1] | NM_123320 |
| A_84_P15224 | 1.54 | down | WAKL2 | WAKL2 (WALL ASSOCIATED KINASE-LIKE 2); kinase [AT1G16130.1] | NM_101480 |
| A_84_P16072 | 1.80 | down | AT1G65690 | harpin-induced protein-related/HIN1-related/harpin-responsive protein-related [AT1G65690.1] | NM_105243 |
| A_84_P855834 | 2.63 | down | | NM_001035537 acid phosphatase {Arabidopsis thaliana} (exp = −1; wgp = 0; cg = 0), partial (6%) [TC310073] | |
| A_84_P809465 | 1.64 | down | | BT002101 plasma membrane intrinsic protein 1C (transmembrane protein B) {Arabidopsis thaliana} (exp = −1; wgp = 0; cg = 0), partial (53%) [TC314205] | |
| A_84_P594418 | 2.36 | down | AT2G17660 | nitrate-responsive NOI protein, putative [AT2G17660.1] | NM_127320 |
| A_84_P839984 | 1.62 | down | AT1G63580 | protein kinase-related [AT1G63580.1] | NM_105036 |
| A_84_P156125 | 3.78 | down | BAP1 | BAP1 (BON ASSOCIATION PROTEIN 1) [AT3G61190.1] | NM_115983 |
| A_84_P819549 | 2.45 | down | AT5G41740 | disease resistance protein (TIR-NBS-LRR class), putative [AT5G41740.1] | NM_123539 |
| A_84_P550912 | 2.15 | down | AT2G45135 | protein binding/zinc ion binding [AT2G45135.1] | NM_180099 |
| A_84_P12896 | 1.92 | down | SHB1 | SHB1 (SHORT HYPOCOTYL UNDER BLUE1) [AT4G25350.1] | NM_118667 |
| A_84_P19028 | 6.17 | down | ORA47 | ORA47; DNA binding/transcription factor [AT1G74930.1] | NM_106151 |
| A_84_P17463 | 2.10 | down | AT3G44260 | CCR4-NOT transcription complex protein, putative [AT3G44260.1] | NM_114294 |
| A_84_P241489 | 1.7182 | down | AT4G24130 | similar to unknown protein [Arabidopsis thaliana] (TAIR: AT1G56580.1); similar to unnamed protein product [Vitis vinifera] (GB: CAO62919.1); contains InterPro domain Protein of unknown function DUF538 (InterPro: IPR007493) [AT4G24130.1] | NM_118545 |
| A_84_P829722 | 1.53 | down | CRK11 | CRK11 (CYSTEINE-RICH RLK11); kinase [AT4G23190.1] | NM_118448 |
| A_84_P158475 | 1.962 | down | AT2G41640 | similar to unknown protein [Arabidopsis thaliana] (TAIR: AT3G57380.1); similar to glycosyltransferase [Medicago truncatula] (GB: CAI30145.1); contains InterPro domain Protein of unknown function DUF563 (InterPro: IPR007657) [AT2G41640.1] | NM_129727 |
| A_84_P70804 | 1.96 | down | AT5G63130 | octicosapeptide/Phox/Bem1p (PB1) domain-containing protein [AT5G63130.1] | NM_125707 |
| A_84_P21415 | 1.75 | down | MAPKKK16 | MAPKKK16 (Mitogen-activated protein kinase kinase kinase 16); kinase [AT4G26890.1] | NM_118823 |
| A_84_P13393 | 2.02 | down | AT1G66090 | disease resistance protein (TIR-NBS class), putative [AT1G66090.1] | NM_105280 |
| A_84_P503658 | 1.73 | down | ZYP1b | ZYP1b [AT1G22275.1] | NM_102078 |
| A_84_P14480 | 2.90 | down | AT2G38250 | DNA-binding protein-related [AT2G38250.1] | NM_129382 |
| A_84_P542948 | 2.1672 | down | AT2G46150 | similar to unknown protein [Arabidopsis thaliana] (TAIR: AT3G54200.1); similar to plant cell wall protein SITFR88 [Lycopersicon esculentum] (GB: ABF39005.1); contains InterPro domain Harpin-induced 1 (InterPro: IPR010847) [AT2G46150.1] | NM_130177 |
| A_84_P763030 | 1.59 | down | HHP4 | HHP4 (heptahelical protein 4); receptor [AT4G37680.1] | NM_119991 |
| A_84_P21473 | 2.99 | down | ATBETA-AMY | ATBETA-AMY (BETA-AMYLASE); beta-amylase [AT4G15210.1] | NM_117609 |
| A_84_P18720 | 1.80 | down | MSS1 | MSS1 (SUGAR TRANSPORT PROTEIN 13); carbohydrate transmembrane transporter/hexose:hydrogen symporter/high-affinity hydrogen:glucose symporter/sugar:hydrogen ion symporter [AT5G26340.1] | NM_122535 |
| A_84_P20998 | 3.18 | down | PHI-1 | PHI-1 (PHOSPHATE-INDUCED 1) [AT1G35140.1] | NM_103210 |
| A_84_P750311 | 1.90 | down | AT1G72120 | transporter [AT1G72120.1] | NM_105870 |
| A_84_P11921 | 1.57 | down | IP5PII | IP5PII (INOSITOL POLYPHOSPHATE 5-PHOSPHATASE II); inositol-polyphosphate 5-phosphatase [AT4G18010.1] | NM_179071 |
| A_84_P13086 | 1.69 | down | AT5G44910 | Toll-Interleukin-Resistance (TIR) domain-containing protein [AT5G44910.1] | NM_123859 |
| A_84_P23967 | 3.00 | down | ATGLR2.9 | ATGLR2.9 (Arabidopsis thaliana glutamate receptor 2.9) [AT2G29100.1] | NM_128467 |

TABLE 6-continued

List of Genes Responsive to T1 Treatment

| ProbeName | Fold change | Regulation | Gene Symbol | Description | Genbank Accession |
|---|---|---|---|---|---|
| A_84_P16923 | 3.06 | down | RHL41 | RHL41 (RESPONSIVE TO HIGH LIGHT 41); nucleic acid binding/transcription factor/zinc ion binding [AT5G59820.1] | NM_125374 |
| A_84_P147748 | 1.55 | down | AT1G78210 | hydrolase, alpha/beta fold family protein [AT1G78210.1] | NM_106471 |
| A_84_P12646 | 2.22 | down | AT3G03260 | homeobox-leucine zipper family protein/lipid-binding START domain-containing protein [AT3G03260.1] | NM_111196 |
| A_84_P10284 | 1.96 | down | AT5G54170 | similar to CP5 [Arabidopsis thaliana] (TAIR: AT1G64720.1); similar to putative nodule membrane protein [Medicago sativa] (GB: AAL57201.1); contains InterPro domain Lipid-binding START (InterPro: IPR002913) [AT5G54170.1] | NM_124797 |
| A_84_P822327 | 2.01 | down | | | |
| A_84_P16138 | 3.22 | down | AT1G30700 | FAD-binding domain-containing protein [AT1G30700.1] | NM_102806 |
| A_84_P541993 | 1.71 | down | AT2G27310 | F-box family protein [AT2G27310.1] | NM_128290 |
| A_84_P17327 | 5.15 | down | AT2G34210 | transcription initiation factor [AT2G34210.1] | NM_128972 |
| A_84_P567134 | 1.7198 | down | AT4G27657 | similar to unknown protein [Arabidopsis thaliana] (TAIR: AT4G27652.1) [AT4G27657.1] | NM_118904 |
| A_84_P823170 | 7.90 | down | AT4G35160 | O-methyltransferase family 2 protein [AT4G35160.1] | NM_119682 |
| A_84_P15113 | 1.86 | down | AT1G71520 | AP2 domain-containing transcription factor, putative [AT1G71520.1] | NM_105820 |
| A_84_P752604 | 1.88 | down | AT1G09500 | cinnamyl-alcohol dehydrogenase family/CAD family [AT1G09500.2] | NM_001035935 |
| A_84_P21874 | 2.69 | down | STZ | STZ (SALT TOLERANCE ZINC FINGER); nucleic acid binding/transcription factor/zinc ion binding [AT1G27730.1] | NM_102538 |
| A_84_P19904 | 1.99 | down | ATGSTU17/ERD9/ GST30/GST30B | ATGSTU17/ERD9/GST30/GST30B (EARLY-RESPONSIVE TO DEHYDRATION 9); glutathione transferase [AT1G10370.1] | NM_100911 |
| A_84_P846303 | 2.25 | down | WRKY6 | WRKY6 (WRKY DNA-binding protein 6); transcription factor [AT1G62300.1] | NM_104910 |
| A_84_P10724 | 1.65 | down | AT2G30020 | protein phosphatase 2C, putative/PP2C, putative [AT2G30020.1] | NM_128557 |
| A_84_P10141 | 1.55 | down | AT5G01550 | lectin protein kinase, putative [AT5G01550.1] | NM_120233 |
| A_84_P216248 | 1.5285 | down | AT1G69890 | similar to unknown protein [Arabidopsis thaliana] (TAIR: AT1G27100.1); similar to unknown [Populus trichocarpa] (GB: ABK94560.1); contains InterPro domain Protein of unknown function DUF569 (InterPro: IPR007679); contains InterPro domain Actin-crosslinking proteins (InterPro: IPR008999) [AT1G69890.1] | NM_105657 |
| A_84_P23237 | 1.61 | down | AT4G03450 | ankyrin repeat family protein [AT4G03450.1] | NM_116583 |
| A_84_P11333 | 3.36 | down | AT1G71530 | protein kinase family protein [AT1G71530.1] | NM_202395 |
| A_84_P830413 | 1.77 | down | ATFH8 | ATFH8 (FORMIN 8); actin binding/actin filament binding/profilin binding [AT1G70140.1] | NM_105682 |
| A_84_P19943 | 2.28 | down | AT1G49450 | transducin family protein/WD-40 repeat family protein [AT1G49450.1] | NM_103834 |
| A_84_P11046 | 11.41 | down | AT4G34410 | AP2 domain-containing transcription factor, putative [AT4G34410.1] | NM_119606 |
| A_84_P785475 | 3.73 | down | LOX3 | LOX3 (Lipoxygenase 3); iron ion binding/lipoxygenase/metal ion binding/oxidoreductase, acting on single donors with incorporation of molecular oxygen, incorporation of two atoms of oxygen [AT1G17420.1] | NM_101603 |
| A_84_P23255 | 1.53 | down | AT4G10650 | GTP-binding family protein [AT4G10650.1] | NM_117133 |
| A_84_P17613 | 1.58 | down | AGL19 | AGL19 (AGAMOUS-LIKE 19); transcription factor [AT4G22950.1] | NM_118424 |
| A_84_P21931 | 2.58 | down | ATERF11/ERF11 | ATERF11/ERF11 (ERF domain protein 11); DNA binding/transcription factor/transcription repressor [AT1G28370.1] | NM_102603 |
| A_84_P20535 | 2.47 | down | ATERF-1 | ATERF-1 (ETHYLENE RESPONSIVE ELEMENT BINDING FACTOR 1); DNA binding/transcription activator/transcription factor [AT4G17500.1] | NM_117855 |
| A_84_P840707 | 1.98 | down | AT1G07500 | unknown protein [AT1G07500.1] | NM_100624 |
| A_84_P869292 | 2.35 | down | ATERF-1 | ATERF-1 (ETHYLENE RESPONSIVE ELEMENT BINDING FACTOR 1); DNA binding/transcription activator/transcription factor [AT4G17500.1] | NM_117855 |
| A_84_P293284 | 2.02 | down | AT2G36780 | UDP-glucoronosyl/UDP-glucosyl transferase family protein [AT2G36780.1] | NM_129233 |
| A_84_P14144 | 2.37 | down | AT1G28170 | sulfotransferase family protein [AT1G28170.1] | NM_102583 |
| A_84_P15331 | 1.69 | down | AT2G43620 | chitinase, putative [AT2G43620.1] | NM_129924 |

TABLE 6-continued

List of Genes Responsive to T1 Treatment

| ProbeName | Fold change | Regulation | Gene Symbol | Description | Genbank Accession |
|---|---|---|---|---|---|
| A_84_P269630 | 7.23 | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] | NM_179772 |
| A_84_P800343 | 1.92 | down | | AYBJY37TR pooled cDNA populations *Arabidopsis thaliana* cDNA, mRNA sequence [EG508437] | |
| A_84_P849144 | 2.80 | down | AT5G41750 | disease resistance protein (TIR-NBS-LRR class), putative [AT5G41750.2] | NM_123540 |
| A_84_P197444 | 1.75 | down | AT3G22160 | VQ motif-containing protein [AT3G22160.1] | NM_113113 |
| A_84_P17802 | 1.84 | down | ATCHX18 | ATCHX18 (cation/hydrogen exchanger 18); monovalent cation:proton antiporter [AT5G41610.1] | NM_123525 |
| A_84_P218298 | 1.76 | down | AT2G42760 | similar to unnamed protein product [*Vitis vinifera*] (GB: CAO69913.1) [AT2G42760.1] | NM_129837 |
| A_84_P843641 | 1.98 | down | AT2G34210 | transcription initiation factor [AT2G34210.1] | NM_128972 |
| A_84_P575222 | 1.68 | down | AT5G09800 | U-box domain-containing protein [AT5G09800.1] | NM_121017 |
| A_84_P14748 | 4.20 | down | LOX3 | LOX3 (Lipoxygenase 3); iron ion binding/ lipoxygenase/metal ion binding/oxidoreductase, acting on single donors with incorporation of molecular oxygen, incorporation of two atoms of oxygen [AT1G17420.1] | NM_101603 |
| A_84_P573393 | 4.07 | down | AT4G27654 | unknown protein [AT4G27654.1] | NM_118903 |
| A_84_P124252 | 1.51 | down | ATCAMBP25 | ATCAMBP25 (*ARABIDOPSIS THALIANA* CALMODULIN (CAM)-BINDING PROTEIN OF 25 KDA); calmodulin binding [AT2G41010.1] | NM_129666 |
| A_84_P18823 | 1.58 | down | AT5G61560 | protein kinase family protein [AT5G61560.1] | NM_125549 |
| A_84_P866261 | 2.12 | down | AT4G20860 | FAD-binding domain-containing protein [AT4G20860.1] | NM_118204 |
| A_84_P15269 | 4.02 | down | ANAC019 | ANAC019 (*Arabidopsis* NAC domain containing protein 19); transcription factor [AT1G52890.1] | NM_104167 |
| A_84_P789523 | 2.73 | down | AT5G03545 | unknown protein [AT5G03545.1] | NM_180427 |
| A_84_P10496 | 1.59 | down | ATUGT85A1/UGT85A1 | ATUGT85A1/UGT85A1 (UDP-GLUCOSYL TRANSFERASE 85A1); UDP-glycosyltransferase/ glucuronosyltransferase/transferase, transferring glycosyl groups/transferase, transferring hexosyl groups [AT1G22400.1] | NM_102089 |
| A_84_P275700 | 6.03 | down | AT3G44510 | similar to esterase/lipase/thioesterase family protein [*Arabidopsis thaliana*] (TAIR: AT1G08310.1); similar to esterase/lipase/thioesterase family protein [*Arabidopsis thaliana*] (TAIR: AT1G08310.2); similar to hypothetical protein [*Vitis vinifera*] (GB: CAN60741.1); contains domain SSF53474 (SSF53474) [AT3G44510.1] | NM_114319 |
| A_84_P14054 | 2.38 | down | RHD2 | RHD2 (ROOT HAIR DEFECTIVE 2) [AT5G51060.1] | NM_124485 |
| A_84_P22736 | 2.13 | down | AT1G09500 | cinnamyl-alcohol dehydrogenase family/CAD family [AT1G09500.1] | NM_179294 |
| A_84_P606188 | 2.85 | down | AT3G28007 | nodulin MtN3 family protein [AT3G28007.1] | NM_113718 |
| A_84_P14426 | 1.55 | down | AT2G23300 | leucine-rich repeat transmembrane protein kinase, putative [AT2G23300.1] | NM_127894 |
| A_84_P12186 | 1.59 | down | AT5G57480 | AAA-type ATPase family protein [AT5G57480.1] | NM_125129 |
| A_84_P579612 | 1.8401 | down | AT4G27652 | similar to unknown protein [*Arabidopsis thaliana*] (TAIR: AT4G27657.1) [AT4G27652.1] | NM_118902 |
| A_84_P815576 | 1.68 | down | | | |
| A_84_P18359 | 2.81 | down | AGC2-1 | AGC2-1 (OXIDATIVE SIGNAL-INDUCIBLE1); kinase [AT3G25250.1] | NM_113431 |
| A_84_P96456 | 1.64 | down | MT1A | MT1A (METALLOTHIONEIN 1A) [AT1G07600.1] | NM_100633 |
| A_84_P15934 | 1.85 | down | SMG1 | SMG1 (SMALL MOLECULAR WEIGHT G-PROTEIN 1); GTP binding [AT5G47960.1] | NM_124170 |
| A_84_P803335 | 3.11 | down | AT3G28007 | nodulin MtN3 family protein [AT3G28007.1] | NM_113718 |
| A_84_P561097 | 2.08 | down | AT5G46295 | unknown protein [AT5G46295.1] | NM_123999 |
| A_84_P573240 | 3.9244 | down | AT3G43110 | similar to unknown protein [*Arabidopsis thaliana*] (TAIR: AT5G20790.1) [AT3G43110.1] | NM_114179 |
| A_84_P21275 | 2.51 | down | AT3G50930 | AAA-type ATPase family protein [AT3G50930.1] | NM_114953 |
| A_84_P15382 | 8.30 | down | CYP71A13 | CYP71A13 (CYTOCHROME P450, FAMILY 71, SUBFAMILY A, POLYPEPTIDE 13); indoleacetaldoxime dehydratase/oxygen binding [AT2G30770.1] | NM_128630 |
| A_84_P206058 | 2.6306 | down | AT4G37290 | similar to unknown protein [*Arabidopsis thaliana*] (TAIR: AT2G23270.1); similar to hypothetical protein [*Vitis vinifera*] (GB: CAN62855.1) [AT4G37290.1] | NM_119892 |
| A_84_P286120 | 2.12 | down | CYP707A1 | CYP707A1 (cytochrome P450, family 707, subfamily A, polypeptide 1); oxygen binding [AT4G19230.1] | NM_202845 |
| A_84_P804466 | 1.79 | down | AT3G28560 | similar to AAA-type ATPase family protein [*Arabidopsis thaliana*] (TAIR: AT3G28510.1); similar to hypothetical protein [*Vitis vinifera*] (GB: CAN79616.1); contains domain PTHR23070 (PTHR23070); contains | NM_113776 |

TABLE 6-continued

List of Genes Responsive to T1 Treatment

| ProbeName | Fold change | Regulation | Gene Symbol | Description | Genbank Accession |
|---|---|---|---|---|---|
| | | | | domain PTHR23070: SF1 (PTHR23070: SF1) [AT3G28560.1] | |
| A_84_P219668 | 1.99 | down | AT3G04640 | glycine-rich protein [AT3G04640.1] | NM_111336 |
| A_84_P762419 | 1.68 | down | AT3G15518 | similar to hypothetical protein [*Nicotiana benthamiana*] (GB: BAF02554.1) [AT3G15518.1] | NM_001125163 |
| A_84_P21746 | 4.00 | down | AT1G17710 | phosphoric monoester hydrolase [AT1G17710.1] | NM_001084087 |
| A_84_P21049 | 1.68 | down | PLP2 | PLP2 (PHOSPHOLIPASE A 2A); nutrient reservoir [AT2G26560.1] | NM_128213 |
| A_84_P555663 | 2.64 | down | AT5G03545 | unknown protein [AT5G03545.1] | NM_180427 |
| A_84_P857638 | 7.70 | down | CYP71A13 | CYP71A13 (CYTOCHROME P450, FAMILY 71, SUBFAMILY A, POLYPEPTIDE 13); indoleacetaldoxime dehydratase/oxygen binding [AT2G30770.1] | NM_128630 |
| A_84_P809477 | 2.69 | down | TMP-C | TMP-C (PLASMA MEMBRANE INTRINSIC PROTEIN 1; 4); water channel [AT4G00430.1] | NM_116268 |
| A_84_P66214 | 2.53 | down | AT3G02840 | immediate-early fungal elicitor family protein [AT3G02840.1] | NM_111152 |
| A_84_P595805 | 1.9338 | down | AT5G36925 | similar to unknown protein [*Arabidopsis thaliana*] (TAIR: AT5G36920.1) [AT5G36925.1] | NM_180586 |
| A_84_P301340 | 1.6799 | down | AT1G80120 | similar to unknown protein [*Arabidopsis thaliana*] (TAIR: AT3G15810.1); similar to unknown [*Populus trichocarpa*] (GB: ABK95691.1); contains InterPro domain Protein of unknown function DUF567 (InterPro: IPR007612) [AT1G80120.1] | NM_106661 |
| A_84_P12764 | 1.74 | down | GATL2 | GATL2 (Galacturonosyltransferase-like 2); polygalacturonate 4-alpha-galacturonosyltransferase/ transferase, transferring glycosyl groups/transferase, transferring hexosyl groups [AT3G50760.1] | NM_114936 |
| A_84_P23343 | 1.7307 | down | AT4G35110 | similar to unknown protein [*Arabidopsis thaliana*] (TAIR: AT2G16900.1); contains InterPro domain Phospholipase-like, *arabidopsis* (InterPro: IPR007942) [AT4G35110.1] | NM_001125647 |
| A_84_P845237 | 1.52 | down | | Q9FXE4_ARATH (Q9FXE4) F12A21.5, complete [TC289164] | |
| A_84_P13187 | 1.75 | down | MGD2 | MGD2 (monogalactosyldiacylglycerol synthase 2); 1,2-diacylglycerol 3-beta-galactosyltransferase/ transferase, transferring glycosyl groups [AT5G20410.1] | NM_122048 |
| A_84_P11698 | 1.80 | down | PLDP2 | PLDP2 (PHOSPHOLIPASE D ZETA 2); phospholipase D [AT3G05630.1] | NM_111436 |
| A_84_P755231 | 1.54 | down | AT2G14270 | pseudogene, protein phosphatase 2C, blastp match of 60% identity and 2.5e−08 P-value to GP [AT2G14270.1] | |
| A_84_P140849 | 2.3459 | down | AT1G32920 | similar to unknown protein [*Arabidopsis thaliana*] (TAIR: AT1G32928.1) [AT1G32920.1] | NM_103025 |
| A_84_P158205 | 2.6465 | down | AT1G22470 | similar to unknown protein [*Arabidopsis thaliana*] (TAIR: AT1G72240.1) [AT1G22470.1] | NM_102096 |
| A_84_P14331 | 3.36 | down | CML38 | CML38; calcium ion binding [AT1G76650.1] | NM_106315 |
| A_84_P17447 | 1.63 | down | ATBFRUCT1/ATCWINV1 | ATBFRUCT1/ATCWINV1 (*ARABIDOPSIS THALIANA* CELL WALL INVERTASE 1); beta-fructofuranosidase/ hydrolase, hydrolyzing O-glycosyl compounds [AT3G13790.1] | NM_112232 |
| A_84_P169313 | 3.57 | down | ProT3 | ProT3 (PROLINE TRANSPORTER 3); amino acid transmembrane transporter [AT2G36590.1] | NM_129215 |
| A_84_P869273 | 2.06 | down | AT3G44260 | CCR4-NOT transcription complex protein, putative [AT3G44260.1] | NM_114294 |
| A_84_P834970 | 1.83 | down | AT1G66830 | leucine-rich repeat transmembrane protein kinase, putative [AT1G66830.1] | NM_105354 |
| A_84_P870349 | 4.30 | down | AtMYB15/AtY19/MYB15 | AtMYB15/AtY19/MYB15 (myb domain protein 15); DNA binding [AT3G23250.2] | NM_001035670 |
| A_84_P11789 | 5.29 | down | AT3G43250 | cell cycle control protein-related [AT3G43250.1] | NM_114193 |
| A_84_P19511 | 1.95 | down | AT4G24380 | hydrolase, acting on ester bonds [AT4G24380.1] | NM_001036630 |
| A_84_P792696 | 1.52 | down | | *Arabidopsis thaliana* clone 92240 mRNA sequence [DQ108884] | |

TABLE 7

List of Genes Responsive to T2 treatment

| ProbeName | Fold change | Regulation | Gene Symbol | Description | Genbank Accessio |
|---|---|---|---|---|---|
| A_84_P840007 | 2.20 | up | AT1G18460 | lipase family protein [AT1G18460.1] | NM_101703 |
| A_84_P754651 | 1.97 | up | AT1G65484 | unknown protein [AT1G65484.1] | NM_001124078 |
| A_84_P827514 | 2.28 | up | AT1G79910 | similar to unknown protein [*Arabidopsis thaliana*] (TAIR: AT1G52315.1); similar to unnamed protein product [*Vitis vinifera*] (GB: CAO45916.1); contains InterPro domain Protein of unknown function DUF292, eukaryotic (InterPro: IPR005061) [AT1G79910.1] | NM_106640 |
| A_84_P816917 | 1.56 | up | | | |
| A_84_P10832 | 2.19 | up | AT3G32040 | geranylgeranyl pyrophosphate synthase, putative/ GGPP synthetase, putative/farnesyltranstransferase, putative [AT3G32040.1] | NM_114027 |
| A_84_P59580 | 2.35 | up | AT4G34560 | similar to unknown protein [*Arabidopsis thaliana*] (TAIR: AT5G66440.1); similar to hypothetical protein [Vitis vinifera] (GB: CAN77202.1) [AT4G34560.1] | NM_119622 |
| A_84_P819451 | 1.65 | up | AT5G13290 | protein kinase family protein [AT5G13290.3] | NM_001085108 |
| A_84_P831322 | 2.54 | up | AT3G18770 | similar to unknown protein [*Arabidopsis thaliana*] (TAIR: AT3G49590.1); similar to unknown protein [*Arabidopsis thaliana*] (TAIR: AT3G49590.2); similar to unnamed protein product [*Vitis vinifera*] (GB: CAO46479.1) [AT3G18770.1] | NM_112763 |
| A_84_P137499 | 1.51 | up | PIL5 | PIL5 (PHYTOCHROME INTERACTING FACTOR 3-LIKE 5); transcription factor [AT2G20180.1] | NM_179665 |
| A_84_P20366 | 1.60 | up | ACR4 | ACR4 (*ARABIDOPSIS* CRINKLY4); kinase [AT3G59420.1] | NM_115804 |
| A_84_P22506 | 1.52 | up | ATGID1C/GID1C | ATGID1C/GID1C (GA INSENSITIVE DWARF1C); hydrolase [AT5G27320.1] | NM_122614 |
| A_84_P849653 | 1.52 | up | AT2G01680 | ankyrin repeat family protein [AT2G01680.1] | NM_126229 |
| A_84_P853394 | 1.56 | up | HEMB1 | HEMB1 [AT1G69740.2] | NM_001084331 |
| A_84_P861596 | 1.87 | up | | Q9ZS01_ARATH (Q9ZS01) RNA helicase (Fragment), partial (35%) [TC313472] | |
| A_84_P826388 | 1.54 | up | BR6OX2/CYP85A2 | BR6OX2/CYP85A2 (BRASSINOSTEROID-6-OXIDASE 2); monooxygenase/oxygen binding [AT3G30180.1] | NM_113917 |
| A_84_P12198 | 1.53 | up | AT5G60200 | Dof-type zinc finger domain-containing protein [AT5G60200.1] | NM_125413 |
| A_84_P553411 | 1.78 | up | AT1G71870 | MATE efflux family protein [AT1G71870.1] | NM_105845 |
| A_84_P816867 | 1.51 | up | AT5G14260 | SET domain-containing protein [AT5G14260.2] | NM_121430 |
| A_84_P22437 | 1.84 | up | AT5G02140 | thaumatin-like protein, putative [AT5G02140.1] | NM_120292 |
| A_84_P802490 | 1.74 | up | AT1G01180 | similar to nucleic acid binding [*Arabidopsis thaliana*] (TAIR: AT5G19270.1); similar to hypothetical protein [*Vitis vinifera*] (GB: CAN77331.1); contains domain SSF53335 (SSF53335) [AT1G01180.1] | NM_100000 |
| A_84_P296824 | 2.17 | up | AT3G15450 | similar to unknown protein [*Arabidopsis thaliana*] (TAIR: AT4G27450.1); similar to unknown [*Populus trichocarpa*] (GB: ABK93866.1); contains domain PTHR11772 (PTHR11772); contains domain G3DSA: 3.60.20.10 (G3DSA: 3.60.20.10); contains domain SSF56235 (SSF56235) [AT3G15450.1] | NM_001035625 |
| A_84_P833057 | 1.77 | up | AT3G19553 | amino acid permease family protein [AT3G19553.1] | NM_112845 |
| A_84_P94699 | 1.82 | up | AT4G10865 | transposable element gene [AT4G10865.1] | |
| A_84_P16486 | 1.54 | up | CYP705A21 | CYP705A21 (cytochrome P450, family 705, subfamily A, polypeptide 21); oxygen binding [AT3G20120.1] | NM_112903 |
| A_84_P20551 | 1.68 | up | MLS | MLS (MALATE SYNTHASE); malate synthase [AT5G03860.1] | NM_120467 |
| A_84_P813537 | 1.51 | up | SBPASE | SBPASE (SEDOHEPTULOSE-BISPHOSPHATASE); phosphoric ester hydrolase/sedoheptulose-bisphosphatase [AT3G55800.1] | NM_115438 |
| A_84_P509156 | 1.52 | up | AT2G19240 | RabGAP/TBC domain-containing protein [AT2G19240.1] | NM_127481 |
| A_84_P849211 | 1.60 | up | KAT2/PED1 | KAT2/PED1 (PEROXISOME DEFECTIVE 1); acetyl-CoA C-acyltransferase [AT2G33150.1] | NM_128874 |
| A_84_P822005 | 1.59 | up | ICE1 | ICE1 (INDUCER OF CBF EXPRESSION 1); DNA binding [AT3G26744.2] | NM_001035697 |
| A_84_P836875 | 1.55 | up | AT3G13690 | protein kinase family protein [AT3G13690.1] | NM_112219 |
| A_84_P857924 | 2.57 | up | AT3G27470 | similar to unknown protein [*Arabidopsis thaliana*] (TAIR: AT1G67850.1); similar to unknown protein [*Arabidopsis thaliana*] (TAIR: AT1G67850.2); similar to unnamed protein product [*Vitis vinifera*] (GB: CAO14680.1); contains InterPro domain Protein of unknown function DUF707 (InterPro: IPR007877) [AT3G27470.2] | NM_001084748 |
| A_84_P848467 | 2.18 | up | AT1G36070 | WD-40 repeat family protein [AT1G36070.1] | NM_103303 |
| A_84_P836542 | 1.63 | up | CYP71B34 | CYP71B34 (cytochrome P450, family 71, subfamily B, polypeptide 34); oxygen binding [AT3G26300.1] | NM_113537 |

TABLE 7-continued

List of Genes Responsive to T2 treatment

| ProbeName | Fold change | Regulation | Gene Symbol | Description | Genbank Accessio |
|---|---|---|---|---|---|
| A_84_P207448 | 1.57 | up | PBB1 | PBB1 (20S proteasome beta subunit B 1); peptidase [AT3G27430.1] | NM_180310 |
| A_84_P21472 | 1.57 | up | ATSUV3 | ATSUV3 (embryo sac development arrest 15) [AT4G14790.1] | NM_117564 |
| A_84_P15177 | 1.64 | up | ATGLX1 | ATGLX1 (GLYOXALASE I HOMOLOG); lactoylglutathione lyase [AT1G11840.1] | NM_001035949 |
| A_84_P820397 | 1.67 | up | AT2G46550 | similar to unknown protein [*Arabidopsis thaliana*] (TAIR: AT1G01240.3); similar to unknown protein [*Arabidopsis thaliana*] (TAIR: AT1G01240.1); similar to unknown protein [*Arabidopsis thaliana*] (TAIR: AT1G01240.2); similar to unnamed protein product [*Vitis vinifera*] (GB: CAO14395.1) [AT2G46550.1] | NM_130220 |
| A_84_P832658 | 1.54 | up | CYP709B3 | CYP709B3 (cytochrome P450, family 709, subfamily B, polypeptide 3); oxygen binding [AT4G27710.1] | NM_118910 |
| A_84_P230039 | 1.99 | up | AT5G43065 | transposable element gene [AT5G43065.1] | |
| A_84_P843739 | 1.74 | up | AT2G47300 | ribonuclease P [AT2G47300.3] | NM_001084604 |
| A_84_P186764 | 1.82 | up | AT3G21100 | RNA recognition motif (RRM)-containing protein [AT3G21100.1] | NM_113004 |
| A_84_P513598 | 1.54 | up | AT2G22122 | unknown protein [AT2G22122.1] | NM_201779 |
| A_84_P818830 | 1.59 | up | | | |
| A_84_P613195 | 1.56 | up | AT3G02370 | similar to unknown protein [*Arabidopsis thaliana*] (TAIR: AT3G57360.1); similar to hypothetical protein [*Vitis vinifera*] (GB: CAN74373.1) [AT3G02370.1] | NM_111104 |
| A_84_P509692 | 1.56 | up | AT5G47900 | similar to unknown protein [*Arabidopsis thaliana*] (TAIR: AT5G27730.1); similar to unnamed protein product [*Vitis vinifera*] (GB: CAO68737.1) [AT5G47900.2] | NM_001125920 |
| A_84_P268580 | 2.13 | up | ATOFP13/OFP13 | ATOFP13/OFP13 (*Arabidopsis thaliana* ovate family protein 13) [AT5G04820.1] | NM_120564 |
| A_84_P609756 | 1.95 | up | AT3G50030 | binding [AT3G50030.1] | NM_114863 |
| A_84_P846067 | 1.58 | up | AT5G23060 | similar to unknown protein [*Arabidopsis thaliana*] (TAIR: AT3G59780.1); similar to extracellular Ca2+ sensing receptor [*Glycine max*] (GB: ABY57763.1); contains InterPro domain Rhodanese-like (InterPro: IPR001763) [AT5G23060.1] | NM_122212 |
| A_84_P822881 | 1.57 | up | IQD21 | IQD21 (IQ-DOMAIN 21, IQ-domain 21); calmodulin binding [AT3G49260.2] | NM_202676 |
| A_84_P767648 | 1.67 | up | AT5G47900 | similar to unknown protein [*Arabidopsis thaliana*] (TAIR: AT5G27730.1); similar to unnamed protein product [*Vitis vinifera*] (GB: CAO68737.1) [AT5G47900.1] | NM_001125921 |
| A_84_P20851 | 1.67 | up | AT1G75640 | leucine-rich repeat family protein/protein kinase family protein [AT1G75640.1] | NM_106216 |
| A_84_P812038 | 1.89 | up | DRM1 | DRM1 (DORMANCY-ASSOCIATED PROTEIN 1) [AT1G28330.2] | NM_179389 |
| A_84_P798436 | 2.16 | up | | AYBLI62TF pooled cDNA populations *Arabidopsis thaliana* cDNA, mRNA sequence [EG497537] | |
| A_84_P17063 | 2.20 | up | ATPUP4 | ATPUP4 (*Arabidopsis thaliana* purine permease 4); purine transmembrane transporter [AT1G30840.1] | NM_102821 |
| A_84_P22373 | 2.61 | up | AT1G08120 | ATP binding/protein kinase [AT1G08120.1] | NM_100688 |
| A_84_P830199 | 2.34 | up | AT1G73930 | similar to unnamed protein product [*Vitis vinifera*] (GB: CAO68016.1); similar to hypothetical protein OsJ_009810 [*Oryza sativa* (japonica cultivar-group)] (GB: EAZ26327.1); similar to hypothetical protein [*Vitis vinifera*] (GB: CAN70280.1); contains InterPro domain Protein of unknown function DUF1630 (InterPro: IPR012860) [AT1G73930.1] | NM_106052 |
| A_84_P812024 | 1.86 | up | DRM1 | DRM1 (DORMANCY-ASSOCIATED PROTEIN 1) [AT1G28330.1] | NM_102599 |
| A_84_P22397 | 1.58 | up | PIP3 | PIP3 (PLASMA MEMBRANE INTRINSIC PROTEIN 3); water channel [AT4G35100.1] | NM_119676 |
| A_84_P850714 | 1.61 | up | PLA IIIB/PLP9 | PLA IIIB/PLP9 (Patatin-like protein 9); nutrient reservoir [AT3G63200.1] | NM_116185 |
| A_84_P850969 | 1.51 | up | ATPDIL1-4 | ATPDIL1-4 (PDI-LIKE 1-4); thiol-disulfide exchange intermediate [AT5G60640.1] | NM_180903 |
| A_84_P17529 | 1.52 | up | AT3G59580 | RWP-RK domain-containing protein [AT3G59580.1] | NM_115820 |
| A_84_P848153 | 1.70 | up | AT1G70280 | NHL repeat-containing protein [AT1G70280.1] | NM_180643 |
| A_84_P16381 | 1.53 | up | AT2G34190 | xanthine/uracil permease family protein [AT2G34190.1] | NM_128970 |
| A_84_P790392 | 1.81 | up | | *Arabidopsis thaliana* Full-length cDNA Complete sequence from clone GSLTPGH72ZD06 of Hormone Treated Callus of strain col-0 of *Arabidopsis thaliana* (thale cress) [BX824789 ] | |

TABLE 7-continued

List of Genes Responsive to T2 treatment

| ProbeName | Fold change | Regulation | Gene Symbol | Description | Genbank Accessio |
|---|---|---|---|---|---|
| A_84_P849266 | 2.23 | up | AT5G20120 | similar to unnamed protein product [*Vitis vinifera*] (GB: CAO65640.1) [AT5G20120.1] | NM_122019 |
| A_84_P20928 | 2.81 | up | AT1G64470 | ubiquitin family protein [AT1G64470.1] | NM_105122 |
| A_84_P721943 | 1.62 | up | | GL11_ARATH (P92998) Germin-like protein subfamily 1 member 1 precursor, complete [TC298929] | |
| A_84_P16591 | 1.79 | up | TUBG1 | TUBG1 (GAMMA-TUBULIN); structural molecule [AT3G61650.1] | NM_116030 |
| A_84_P17073 | 1.66 | up | AT1G75500 | nodulin MtN21 family protein [AT1G75500.1] | NM_106203 |
| A_84_P854104 | 1.94 | up | AT5G58950 | protein kinase family protein [AT5G58950.1] | NM_125285 |
| A_84_P855440 | 2.04 | up | AT3G15450 | similar to unknown protein [*Arabidopsis thaliana*] (TAIR: AT4G27450.1); similar to unknown [*Populus trichocarpa*] (GB: ABK93866.1); contains domain N-terminal nucleophile aminohydrolases (Ntn hydrolases) (SSF56235); contains domain no description (G3DSA: 3.60.20.10) [AT3G15450.3] | NM_001035625 |
| A_84_P850976 | 1.92 | up | AT3G07310 | similar to unknown protein [*Arabidopsis thaliana*] (TAIR: AT5G48590.1); similar to expressed protein [*Oryza sativa (japonica* cultivar-group)] (GB: ABA93505.2); similar to expressed protein [*Oryza sativa (japonica* cultivar-group)] (GB: ABA93506.2); contains InterPro domain Protein of unknown function DUF760 (InterPro: IPR008479) [AT3G07310.1] | NM_111611 |
| A_84_P832965 | 1.56 | up | AT2G38300 | DNA binding/transcription factor [AT2G38300.1] | NM_129386 |
| A_84_P805355 | 1.52 | up | AT1G12460 | leucine-rich repeat transmembrane protein kinase, putative [AT1G12460.1] | NM_101118 |
| A_84_P514143 | 2.09 | up | AT5G55507 | hydroxyproline-rich glycoprotein family protein [AT5G55507.1] | NM_148134 |
| A_84_P16637 | 1.69 | up | AT4G11470 | protein kinase family protein [AT4G11470.1] | NM_117218 |
| A_84_P11274 | 3.49 | up | AGL68/MAF5 | AGL68/MAF5 (MADS AFFECTING FLOWERING 5); transcription factor [AT5G65080.1] | NM_001085330 |
| A_84_P17557 | 1.63 | up | ATGH9B13 | ATGH9B13 (*ARABIDOPSIS THALIANA* GLYCOSYL HYDROLASE 9B13); hydrolase, hydrolyzing O-glycosyl compounds [AT4G02290.1] | NM_116462 |
| A_84_P24058 | 1.52 | up | AT3G14100 | oligouridylate-binding protein, putative [AT3G14100.1] | NM_112266 |
| A_84_P819307 | 1.76 | up | AT2G43590 | chitinase, putative [AT2G43590.1] | NM_129921 |
| A_84_P852880 | 1.66 | up | WRKY3 | WRKY3 (WRKY DNA-binding protein 3); transcription factor [AT2G03340.1] | NM_126385 |
| A_84_P554830 | 1.58 | up | AT5G20635 | receptor [AT5G20635.1] | NM_147870 |
| A_84_P811499 | 1.60 | up | KAT2/PED1 | KAT2/PED1 (PEROXISOME DEFECTIVE 1); acetyl-CoA C-acyltransferase [AT2G33150.1] | NM_128874 |
| A_84_P583113 | 2.07 | up | AT4G02715 | similar to Os10g0423000 [*Oryza sativa (japonica* cultivar-group)] (GB: NP_001064634.1); similar to Os03g0160200 [*Oryza sativa (japonica* cultivar-group)] (GB: NP_001049036.1) [AT4G02715.1] | NM_148199 |
| A_84_P814104 | 1.57 | up | AT5G23060 | similar to unknown protein [*Arabidopsis thaliana*] (TAIR: AT3G59780.1); similar to extracellular Ca2+ sensing receptor [*Glycine max*] (GB: ABY57763.1); contains InterPro domain Rhodanese-like (InterPro: IPR001763) [AT5G23060.1] | NM_122212 |
| A_84_P22467 | 2.24 | up | AT5G11140 | similar to unknown protein [*Arabidopsis thaliana*] (TAIR: AT4G38560.1); contains InterPro domain Phospholipase-like, *arabidopsis* (InterPro: IPR007942) [AT5G11140.1] | NM_121152 |
| A_84_P12935 | 1.80 | up | AT4G34250 | fatty acid elongase, putative [AT4G34250.1] | NM_119589 |
| A_84_P846062 | 1.64 | up | AT3G26600 | armadillo/beta-catenin repeat family protein [AT3G26600.1] | NM_113569 |
| A_84_P251255 | 1.59 | up | MRH1 | MRH1 (morphogenesis of root hair 1); ATP binding/protein serine/threonine kinase [AT4G18640.1] | NM_117980 |
| A_84_P857396 | 1.67 | up | CYP71B34 | CYP71B34 (cytochrome P450, family 71, subfamily B, polypeptide 34); oxygen binding [AT3G26300.1] | NM_113537 |
| A_84_P851155 | 1.71 | up | AT5G58090 | glycosyl hydrolase family 17 protein [AT5G58090.1] | NM_125194 |
| A_84_P570378 | 2.41 | up | AT2G28690 | similar to unknown protein [*Arabidopsis thaliana*] (TAIR: AT5G59760.1); similar to unnamed protein product [*Vitis vinifera*] (GB: CAO21721.1); contains InterPro domain Protein of unknown function DUF1635 (InterPro: IPR012862) [AT2G28690.1] | NM_128430 |
| A_84_P855559 | 1.97 | up | | Q9LQZ3_ARATH (Q9LQZ3) F10A5.28, partial (35%) [TC309892] | |
| A_84_P16473 | 1.57 | up | AT3G13340 | WD-40 repeat family protein [AT3G13340.1] | NM_112179 |
| A_84_P833200 | 1.54 | up | | | |
| A_84_P246705 | 3.97 | up | AT3G53980 | protease inhibitor/seed storage/lipid transfer protein (LTP) family protein [AT3G53980.1] | NM_180369 |
| A_84_P867363 | 1.51 | up | SCPL25 | SCPL25 (serine carboxypeptidase-like 25); serine carboxypeptidase [AT3G02110.1] | NM_111077 |

TABLE 7-continued

List of Genes Responsive to T2 treatment

| ProbeName | Fold change | Regulation | Gene Symbol | Description | Genbank Accessio |
|---|---|---|---|---|---|
| A_84_P846163 | 1.58 | up | ATALMT9 | ATALMT9 (ALUMINUM-ACTIVATED MALATE TRANSPORTER 9); anion channel/[AT3G18440.1] | NM_112729 |
| A_84_P822097 | 1.56 | up | TCP4 | TCP4 (TCP FAMILY TRANSCRIPTION FACTOR 4); transcription factor [AT3G15030.2] | NM_180258 |
| A_84_P800170 | 3.07 | up | AT2G36980 | pentatricopeptide (PPR) repeat-containing protein [AT2G36980.1] | NM_129254 |
| A_84_P825225 | 2.34 | up | AGL68/MAF5 | AGL68/MAF5 (MADS AFFECTING FLOWERING 5) [AT5G65080.2] | NM_001085330 |
| A_84_P73044 | 1.50 | up | MIZ1 | MIZ1 (MIZU-KUSSEI 1) [AT2G41660.1] | NM_129729 |
| A_84_P21576 | 1.50 | up | AT5G39000 | protein kinase family protein [AT5G39000.1] | NM_123262 |
| A_84_P13703 | 1.59 | up | SRP34A | SRP34A (SER/ARG-RICH PROTEIN 34A); RNA binding [AT3G49430.1] | NM_114803 |
| A_84_P851410 | 1.91 | up | | Q9LE80_ARATH (Q9LE80) Arabidopsis thaliana genomic DNA, chromosome 3, P1 clone: MJK13 (AT3g15450/MJK13_11) (MJK13.11 protein), partial (75%) [TC306364] | |
| A_84_P846334 | 1.52 | up | CYP71B19 | CYP71B19 (cytochrome P450, family 71, subfamily B, polypeptide 19); oxygen binding [AT3G26170.1] | NM_113524 |
| A_84_P528968 | 1.78 | up | AT4G12450 | similar to unknown protein [Arabidopsis thaliana] (TAIR: AT4G22560.1); similar to unnamed protein product [Vitis vinifera] (GB: CAO70345.1); contains domain ADP-ribosylation (SSF56399) [AT4G12450.1] | NM_117315 |
| A_84_P805073 | 2.06 | up | | | |
| A_84_P596516 | 1.51 | up | AT4G14450 | Identical to Uncharacterized protein At4g14450, chloroplast precursor [Arabidopsis Thaliana] (GB: Q6NN02); similar to unknown protein [Arabidopsis thaliana] (TAIR: AT3G23170.1); similar to hypothetical protein [Vitis vinifera] (GB: CAN71216.1) [AT4G14450.1] | NM_117524 |
| A_84_P529858 | 2.33 | up | AT4G12540 | similar to unnamed protein product [Vitis vinifera] (GB: CAO45816.1) [AT4G12540.1] | NM_117324 |
| A_84_P229069 | 1.56 | up | AT5G57130 | protein binding [AT5G57130.1] | NM_125095 |
| A_84_P19283 | 1.70 | up | AT3G17290 | transposable element gene [AT3G17290.1] | |
| A_84_P851295 | 1.61 | up | WRKY39 | WRKY39 (WRKY DNA-binding protein 39); transcription factor [AT3G04670.1] | NM_111339 |
| A_84_P847480 | 1.86 | up | AT5G14480 | glycosyl transferase family 17 protein [AT5G14480.1] | NM_121452 |
| A_84_P833480 | 1.65 | up | | | |
| A_84_P23593 | 1.74 | up | AT5G08350 | GRAM domain-containing protein/ABA-responsive protein-related [AT5G08350.1] | NM_120919 |
| A_84_P17148 | 1.66 | up | ATSBT1.1 | ATSBT1.1; subtilase [AT1G01900.1] | NM_100070 |
| A_84_P10328 | 1.74 | up | MAF4 | MAF4 (MADS AFFECTING FLOWERING 4); transcription factor [AT5G65070.1] | NM_001126027 |
| A_84_P606349 | 2.85 | up | AT4G28460 | unknown protein [AT4G28460.1] | NM_118988 |
| A_84_P828562 | 1.68 | up | ATMPK7 | ATMPK7 (MAP KINASE 7); MAP kinase/kinase [AT2G18170.1] | NM_127374 |
| A_84_P274490 | 1.54 | up | AT4G14930 | acid phosphatase survival protein SurE, putative [AT4G14930.1] | NM_117579 |
| A_84_P819265 | 1.79 | up | AT3G18980 | F-box family protein [AT3G18980.2] | NM_001084716 |
| A_84_P813707 | 1.67 | up | CYP98A3 | CYP98A3 (CYTOCHROME P450, FAMILY 98, SUBFAMILY A, POLYPEPTIDE 3); monooxygenase/ p-coumarate 3-hydroxylase [AT2G40890.1] | NM_180006 |
| A_84_P854337 | 1.89 | up | G6PD5 | G6PD5 (GLUCOSE-6-PHOSPHATE DEHYDROGENASE 5); glucose-6-phosphate dehydrogenase [AT3G27300.2] | NM_001035703 |
| A_84_P853789 | 1.55 | up | AT1G75500 | nodulin MtN21 family protein [AT1G75500.1] | NM_106203 |
| A_84_P845631 | 1.85 | up | AT4G14930 | acid phosphatase survival protein SurE, putative [AT4G14930.1] | NM_117579 |
| A_84_P845713 | 1.93 | up | AT1G30820 | CTP synthase, putative/UTP--ammonia ligase, putative [AT1G30820.1] | NM_102819 |
| A_84_P13011 | 1.60 | up | AT5G11420 | similar to unknown protein [Arabidopsis thaliana] (TAIR: AT5G25460.1); similar to unknown [Ricinus communis] (GB: CAB02653.1); contains InterPro domain Protein of unknown function DUF642 (InterPro: IPR006946); contains InterPro domain Galactose-binding like (InterPro: IPR008979) [AT5G11420.1] | NM_121180 |
| A_84_P533182 | 1.51 | up | AT2G37380 | similar to unknown protein [Arabidopsis thaliana] (TAIR: AT2G39370.1); similar to unnamed protein product [Vitis vinifera] (GB: CAO41570.1) [AT2G37380.1] | NM_129293 |
| A_84_P807865 | 1.56 | up | LOS2 | LOS2 (Low expression of osmotically responsive genes 1); phosphopyruvate hydratase [AT2G36530.1] | NM_129209 |
| A_84_P135065 | 1.62 | up | AT5G20120 | similar to unnamed protein product [Vitis vinifera] (GB: CAO65640.1) [AT5G20120.1] | NM_122019 |
| A_84_P869990 | 2.21 | up | AT5G11140 | similar to unknown protein [Arabidopsis thaliana] | NM_121152 |

TABLE 7-continued

List of Genes Responsive to T2 treatment

| ProbeName | Fold change | Regulation | Gene Symbol | Description | Genbank Accessio |
|---|---|---|---|---|---|
| | | | | (TAIR: AT4G38560.1); contains InterPro domain Phospholipase-like, *arabidopsis* (InterPro: IPR007942) [AT5G11140.1] | |
| A_84_P846752 | 1.75 | up | | Q3HRQ2_9ROSI (Q3HRQ2) Glyoxal oxidase, partial (38%) [TC297818] | |
| A_84_P18014 | 1.52 | up | AT1G11950 | transcription factor [AT1G11950.1] | NM_101067 |
| A_84_P220438 | 1.53 | up | | NM_125000 ATARP8 (ACTIN-RELATED PROTEIN 8); structural constituent of cytoskeleton {*Arabidopsis thaliana*} (exp = −1; wgp = 0; cg = 0), partial (35%) [TC296867] | |
| A_84_P844453 | 2.19 | up | AT4G26760 | microtubule associated protein (MAP65/ASE1) family protein [AT4G26760.1] | NM_118810 |
| A_84_P763306 | 1.63 | up | AT4G06566 | transposable element gene [AT4G06566.1] | |
| A_84_P847165 | 2.34 | up | AT1G73970 | similar to unnamed protein product [*Vitis vinifera*] (GB: CAO63616.1) [AT1G73970.1] | NM_106056 |
| A_84_P22904 | 1.65 | up | AT2G28250 | protein kinase family protein. Binds AtRop4. [AT2G28250.1] | NM_179784 |
| A_84_P828607 | 1.52 | up | AT5G05450 | DEAD/DEAH box helicase, putative (RH18) [AT5G05450.1] | NM_120627 |
| A_84_P18625 | 1.62 | up | AT4G38670 | pathogenesis-related thaumatin family protein [AT4G38670.1] | NM_001125668 |
| A_84_P12443 | 1.52 | up | AT1G80440 | kelch repeat-containing F-box family protein [AT1G80440.1] | NM_106692 |
| A_84_P831327 | 2.29 | up | AT2G45500 | similar to ATPase [*Arabidopsis thaliana*] (TAIR: AT3G27120.1); similar to Tobacco mosaic virus helicase domain-binding protein [*Nicotiana tabacum*] (GB: AAL25088.1); contains InterPro domain AAA ATPase, conserved site; (InterPro: IPR003960); contains InterPro domain MIT (InterPro: IPR007330); contains InterPro domain AAA+ ATPase, core; (InterPro: IPR003593); contains InterPro domain AAA ATPase, core; (InterPro: IPR003959) [AT2G45500.2] | NM_001084594 |
| A_84_P786169 | 1.66 | up | AT5G23060 | similar to unknown protein [*Arabidopsis thaliana*] (TAIR: AT3G59780.1); similar to extracellular Ca2+ sensing receptor [*Glycine max*] (GB: ABY57763.1); contains InterPro domain Rhodanese-like (InterPro: IPR001763) [AT5G23060.1] | NM_122212 |
| A_84_P792877 | 1.60 | up | TUB4 | TUB4 (tubulin beta-4 chain) [AT5G44340.1] | NM_123801 |
| A_84_P12315 | 1.59 | up | ATMGL | ATMGL; catalytic/methionine gamma-lyase [AT1G64660.1] | NM_105141 |
| A_84_P21229 | 1.79 | up | AT3G21420 | oxidoreductase, 2OG-Fe(II) oxygenase family protein [AT3G21420.1] | NM_113037 |
| A_84_P21446 | 1.52 | up | CYCD3/CYCD3; 1/D3 | CYCD3/CYCD3; 1/D3 (CYCLIN D3; 1); cyclin-dependent protein kinase regulator/protein binding [AT4G34160.1] | NM_119579 |
| A_84_P824704 | 1.59 | up | AT2G47850 | zinc finger (CCCH-type) family protein [AT2G47850.1] | NM_130352 |
| A_84_P859145 | 1.88 | up | AT5G19140 | auxin/aluminum-responsive protein, putative [AT5G19140.2] | NM_001036823 |
| A_84_P805118 | 1.81 | up | AT3G15450 | similar to unknown protein [*Arabidopsis thaliana*] (TAIR: AT4G27450.1); similar to unknown [*Populus trichocarpa*] (GB: ABK93866.1); contains domain N-terminal nucleophile aminohydrolases (Ntn hydrolases) (SSF56235); contains domain no description (G3DSA: 3.60.20.10) [AT3G15450.3] | NM_001035625 |
| A_84_P795676 | 1.87 | up | AT5G01850 | BP866957 RAFL21 *Arabidopsis thaliana* cDNA clone RAFL21-79-G22 5', mRNA sequence [BP866957] | |
| A_84_P503065 | 1.75 | up | AT3G05470 | formin homology 2 domain-containing protein/FH2 domain-containing protein [AT3G05470.1] | NM_111420 |
| A_84_P831143 | 1.56 | up | AT1G04010 | phosphatidylcholine-sterol O-acyltransferase [AT1G04010.1] | NM_100282 |
| A_84_P861362 | 1.75 | up | AT1G25440 | zinc finger (B-box type) family protein [AT1G25440.1] | NM_102355 |
| A_84_P192414 | 2.06 | up | AT5G51790 | basix helix-loop-helix (bHLH) family protein [AT5G51790.1] | NM_124558 |
| A_84_P852572 | 1.56 | up | AT4G24290 | similar to NSL1 (NECROTIC SPOTTED LESIONS 1) [*Arabidopsis thaliana*] (TAIR: AT1G28380.1); similar to unnamed protein product [*Vitis vinifera*] (GB: CAO46862.1); similar to unnamed protein product [*Vitis vinifera*] (GB: CAO71620.1); similar to Membrane attack complex component/perforin/complement C9 [*Medicago truncatula*] (GB: ABE79564.1); contains InterPro domain Membrane attack complex component/perforin/complement C9 (InterPro: IPR001862) [AT4G24290.2] | NM_179102 |

TABLE 7-continued

List of Genes Responsive to T2 treatment

| ProbeName | Fold change | Regulation | Gene Symbol | Description | Genbank Accessio |
|---|---|---|---|---|---|
| A_84_P808016 | 1.57 | up | AREB3 | AREB3 (ABA-RESPONSIVE ELEMENT BINDING PROTEIN 3); DNA binding/transcription activator/transcription factor [AT3G56850.1] | NM_115544 |
| A_84_P14837 | 1.75 | up | ANT | ANT (AINTEGUMENTA); DNA binding/transcription factor [AT4G37750.1] | NM_119937 |
| A_84_P796007 | 1.57 | up | AT2G03120 | signal peptide peptidase family protein [AT2G03120.1] | NM_126363 |
| A_84_P831862 | 1.55 | down | AT3G23980 | similar to hypothetical protein OsI_004770 [*Oryza sativa* (*indica* cultivar-group)] (GB: EAY76923.1); contains domain Spectrin repeat (SSF46966) [AT3G23980.1] | NM_113303 |
| A_84_P823733 | 1.76 | down | GATL10 | GATL10 (Galacturonosyltransferase-like 10); polygalacturonate 4-alpha-galacturonosyltransferase/transferase, transferring hexosyl groups [AT3G28340.1] | NM_113753 |
| A_84_P586644 | 2.17 | down | DVL20/RTFL1 | DVL20/RTFL1 (*ROTUNDIFOLIA* 1) [AT3G53232.1] | NM_202692 |
| A_84_P13372 | 1.54 | down | AT1G69840 | band 7 family protein [AT1G69840.1] | NM_202387 |
| A_84_P571830 | 1.54 | down | AT5G65925 | similar to unknown protein [*Arabidopsis thaliana*] (TAIR: AT3G49820.1) [AT5G65925.1] | NM_148165 |
| A_84_P834919 | 2.51 | down | AT1G17210 | zinc ion binding [AT1G17210.1] | NM_101582 |
| A_84_P170813 | 1.67 | down | AT1G74330 | ATP binding/protein kinase [AT1G74330.1] | NM_106093 |
| A_84_P13494 | 2.59 | down | AT2G36690 | oxidoreductase, 2OG-Fe(II) oxygenase family protein [AT2G36690.1] | NM_129224 |
| A_84_P530104 | 1.82 | down | AT5G52740 | heavy-metal-associated domain-containing protein [AT5G52740.1] | NM_124652 |
| A_84_P231379 | 1.55 | down | AT5G46230 | similar to unknown protein [*Arabidopsis thaliana*] (TAIR: AT1G09310.1); similar to unnamed protein product [*Vitis vinifera*] (GB: CAO14438.1); contains InterPro domain Protein of unknown function DUF538 (InterPro: IPR007493) [AT5G46230.1] | NM_123992 |
| A_84_P159915 | 1.66 | down | SLAH2 | SLAH2 (SLAC1 HOMOLOGUE 2); transporter [AT4G27970.1] | NM_118935 |
| A_84_P15523 | 1.55 | down | MUB4 | MUB4 (MEMBRANE-ANCHORED UBIQUITIN-FOLD PROTEIN 4 PRECURSOR) [AT3G26980.1] | NM_113612 |
| A_84_P232439 | 1.70 | down | WRKY18 | WRKY18 (WRKY DNA-binding protein 18); transcription factor [AT4G31800.1] | NM_119329 |
| A_84_P851315 | 1.70 | down | AT1G63750 | ATP binding/nucleoside-triphosphatase/nucleotide binding/protein binding [AT1G63750.2] | NM_001084299 |
| A_84_P115322 | 1.94 | down | AT5G24040 | F-box family protein [AT5G24040.1] | NM_122309 |
| A_84_P13104 | 2.63 | down | WRKY48 | WRKY48 (WRKY DNA-binding protein 48); transcription factor [AT5G49520.1] | NM_124329 |
| A_84_P23024 | 1.74 | down | AT2G47140 | short-chain dehydrogenase/reductase (SDR) family protein [AT2G47140.1] | NM_130282 |
| A_84_P715317 | 1.84 | down | AT1G72416 | heat shock protein binding [AT1G72416.3] | NM_001124117 |
| A_84_P601919 | 2.16 | down | AT4G34550 | similar to F-box family protein [*Arabidopsis thaliana*] (TAIR: AT2G16365.3); similar to F-box family protein [*Arabidopsis thaliana*] (TAIR: AT2G16365.1); similar to unnamed protein product [*Vitis vinifera*] (GB: CAO47597.1) [AT4G34550.1] | NM_119620 |
| A_84_P306860 | 1.82 | down | AT5G10695 | similar to unknown protein [*Arabidopsis thaliana*] (TAIR: AT5G57123.1); similar to unknown [*Picea sitchensis*] (GB: ABK22689.1) [AT5G10695.1] | NM_121107 |
| A_84_P762197 | 1.53 | down | AT3G03341 | similar to Os01g0644200 [*Oryza sativa* (*japonica* cultivar-group)] (GB: NP_001043697.1); similar to unknown [*Picea sitchensis*] (GB: ABK22613.1) [AT3G03341.1] | NM_001125087 |
| A_84_P813079 | 1.65 | down | AT1G69840 | band 7 family protein [AT1G69840.3] | NM_202387 |
| A_84_P14985 | 1.68 | down | ATERF-2/ATERF2/ERF2 | ATERF-2/ATERF2/ERF2 (ETHYLENE RESPONSE FACTOR 2); DNA binding/transcription activator/transcription factor [AT5G47220.1] | NM_124093 |
| A_84_P787702 | 1.80 | down | AGP20 | AGP20 (ARABINOGALACTAN PROTEIN 20) [AT3G61640.1] | NM_116029 |
| A_84_P102986 | 2.46 | down | AT2G27080 | harpin-induced protein-related/HIN1-related/harpin-responsive protein-related [AT2G27080.1] | NM_128266 |
| A_84_P127291 | 1.84 | down | AT5G62860 | F-box family protein-related [AT5G62860.1] | NM_125681 |
| A_84_P13077 | 5.07 | down | CML37/CML39 | CML37/CML39; calcium ion binding [AT5G42380.1] | NM_123603 |
| A_84_P113182 | 3.34 | down | AT4G39670 | glycolipid binding/glycolipid transporter [AT4G39670.1] | NM_120127 |
| A_84_P10528 | 2.41 | down | AT1G51800 | leucine-rich repeat protein kinase, putative [AT1G51800.1] | NM_104059 |
| A_84_P786490 | 1.55 | down | WRKY46 | WRKY46 (WRKY DNA-binding protein 46); transcription factor [AT2G46400.1] | NM_130204 |
| A_84_P19207 | 1.76 | down | AT2G40340 | AP2 domain-containing transcription factor, putative (DRE2B) [AT2G40340.1] | NM_129594 |
| A_84_P511702 | 4.35 | down | AT1G53625 | unknown protein [AT1G53625.1] | NM_179473 |

TABLE 7-continued

List of Genes Responsive to T2 treatment

| ProbeName | Fold change | Regulation | Gene Symbol | Description | Genbank Accessio |
|---|---|---|---|---|---|
| A_84_P21970 | 1.82 | down | AT2G22200 | AP2 domain-containing transcription factor [AT2G22200.1] | NM_127788 |
| A_84_P20728 | 1.63 | down | ABR1 | ABR1 (ABA REPRESSOR1); DNA binding/ transcription factor [AT5G64750.1] | NM_125871 |
| A_84_P762519 | 1.71 | down | AT3G21781 | other RNA [AT3G21781.1] | NR_022759 |
| A_84_P14034 | 1.67 | down | AtRABA1c | AtRABA1c (*Arabidopsis* Rab GTPase homolog A1c); GTP binding [AT5G45750.1] | NM_123942 |
| A_84_P183724 | 2.08 | down | AT2G35290 | similar to unnamed protein product [*Vitis vinifera*] (GB: CAO63442.1) [AT2G35290.1] | NM_129081 |
| A_84_P18291 | 2.16 | down | AT2G27500 | glycosyl hydrolase family 17 protein [AT2G27500.1] | NM_128310 |
| A_84_P528200 | 1.89 | down | FHL | FHL (FAR-RED-ELONGATED HYPOCOTYL1-LIKE); protein binding [AT5G02200.1] | NM_120298 |
| A_84_P15501 | 5.36 | down | ATEXPA12 | ATEXPA12 (*ARABIDOPSIS THALIANA* EXPANSIN 12) [AT3G15370.1] | NM_112405 |
| A_84_P17380 | 1.77 | down | ATPK19 | ATPK19 (*ARABIDOPSIS THALIANA* PROTEIN KINASE 19); kinase [AT3G08720.1] | NM_180212 |
| A_84_P71934 | 1.56 | down | AT1G08050 | zinc finger (C3HC4-type RING finger) family protein [AT1G08050.1] | NM_100679 |
| A_84_P17328 | 3.18 | down | AT2G39350 | ABC transporter family protein [AT2G39350.1] | NM_129492 |
| A_84_P592444 | 2.57 | down | AT1G19200 | senescence-associated protein-related [AT1G19200.1] | NM_101778 |
| A_84_P829746 | 2.68 | down | AT2G42360 | zinc finger (C3HC4-type RING finger) family protein [AT2G42360.1] | NM_129798 |
| A_84_P12056 | 3.49 | down | AT5G08030 | glycerophosphoryl diester phosphodiesterase family protein [AT5G08030.1] | NM_120885 |
| A_84_P825699 | 2.04 | down | AT5G35970 | DNA-binding protein, putative [AT5G35970.1] | NM_122988 |
| A_84_P13013 | 1.60 | down | AT1G18380 | Identical to Uncharacterized protein At1g18380 precursor [*Arabidopsis Thaliana*] (GB: Q5BQ05; GB: Q5Q0G6; GB: Q8RX30; GB: Q9LPQ6); similar to unknown protein [*Arabidopsis thaliana*] (TAIR: AT1G67025.1); similar to unnamed protein product [*Vitis vinifera*] (GB: CAO68096.1) [AT1G18380.1] | NM_101696 |
| A_84_P847209 | 1.70 | down | | Q9FLP4_ARATH (Q9FLP4) Beta-1,3-glucanase-like protein, complete [TC298987] | |
| A_84_P23220 | 3.28 | down | AT3G63380 | calcium-transporting ATPase, plasma membrane-type, putative/Ca(2+)-ATPase, putative (ACA12) [AT3G63380.1] | NM_116203 |
| A_84_P786098 | 4.06 | down | AT1G32920 | 07-E012992-019-004-M01-SP6r MPIZ-ADIS-019 *Arabidopsis thaliana* cDNA clone MPIZp768M014Q 3-PRIME, mRNA sequence [CB253198] | |
| A_84_P607940 | 2.50 | down | AT3G25060 | pentatricopeptide (PPR) repeat-containing protein [AT3G25060.1] | NM_113410 |
| A_84_P868011 | 1.83 | down | SAG21 | SAG21 (SENESCENCE-ASSOCIATED GENE 21) [AT4G02380.1] | NM_116471 |
| A_84_P802502 | 1.79 | down | | *Arabidopsis thaliana* clone 36178 mRNA sequence [DQ108853] | |
| A_84_P769817 | 1.61 | down | | Encodes the D1 subunit of photosystem I and II reaction centers. [ATCG00340.1] | |
| A_84_P16925 | 2.12 | down | AT5G60280 | lectin protein kinase family protein [AT5G60280.1] | NM_125421 |
| A_84_P15734 | 8.95 | down | XTR6 | XTR6 (XYLOGLUCAN ENDOTRANSGLYCOSYLASE 6); hydrolase, acting on glycosyl bonds [AT4G25810.1] | NM_118713 |
| A_84_P120372 | 2.15 | down | ATDTX1 | ATDTX1; antiporter/multidrug efflux pump/multidrug transporter/transporter [AT2G04040.1] | NM_126443 |
| A_84_P242895 | 2.10 | down | AT1G66160 | U-box domain-containing protein [AT1G66160.1] | NM_105287 |
| A_84_P784671 | 1.80 | down | BETA-UP | ATTS6098 AC16H *Arabidopsis thaliana* cDNA clone TAP0254 3' similar to beta-alanine synthetase, mRNA sequence [F20059] | |
| A_84_P289964 | 1.77 | down | AT1G19020 | similar to unknown protein [*Arabidopsis thaliana*] (TAIR: AT3G48180.1); similar to unnamed protein product [*Vitis vinifera*] (GB: CAO40966.1) [AT1G19020.1] | NM_101759 |
| A_84_P18819 | 1.62 | down | ATNRT2.3 | ATNRT2.3 (*Arabidopsis thaliana* high affinity nitrate transporter 2.3); nitrate transmembrane transporter [AT5G60780.1] | NM_125471 |
| A_84_P247225 | 1.61 | down | AT1G01130 | similar to unknown protein [*Arabidopsis thaliana*] (TAIR: AT5G47170.1); contains domain CALCIUM/CALMODULIN-DEPENDENT PROTEIN KINASE-RELATED (PTHR22982); contains domain CBL-INTERACTING PROTEIN KINASE-RELATED (PTHR22982: SF45) [AT1G01130.1] | NM_099995 |

TABLE 7-continued

List of Genes Responsive to T2 treatment

| ProbeName | Fold change | Regulation | Gene Symbol | Description | Genbank Accessio |
|---|---|---|---|---|---|
| A_84_P228659 | 3.07 | down | AT2G32190 | similar to unknown protein [*Arabidopsis thaliana*] (TAIR: AT2G32210.1); similar to unknown [*Populus trichocarpa*] (GB: ABK92801.1); contains domain PD188784 (PD188784) [AT2G32190.1] | NM_001084521 |
| A_84_P605694 | 2.13 | down | AT5G64450 | similar to unknown protein [*Arabidopsis thaliana*] (TAIR: AT3G62200.1); similar to unnamed protein product [*Vitis vinifera*] (GB: CAO40196.1); contains InterPro domain Protein of unknown function DUF537 (InterPro: IPR007491) [AT5G64450.1] | NM_125841 |
| A_84_P82909 | 1.79 | down | AT1G17830 | similar to unknown protein [*Arabidopsis thaliana*] (TAIR: AT1G73210.1); similar to unnamed protein product [*Vitis vinifera*] (GB: CAO45300.1); contains InterPro domain Protein of unknown function DUF789 (InterPro: IPR008507) [AT1G17830.1] | NM_101646 |
| A_84_P136355 | 1.64 | down | AGP20 | AGP20 (ARABINOGALACTAN PROTEIN 20) [AT3G61640.1] | NM_116029 |
| A_84_P12212 | 5.26 | down | AT1G56060 | similar to unknown protein [*Arabidopsis thaliana*] (TAIR: AT2G32190.1); similar to unnamed protein product [*Vitis vinifera*] (GB: CAO68639.1); contains domain PD188784 (PD188784) [AT1G56060.1] | NM_104484 |
| A_84_P512655 | 4.06 | down | AT1G77640 | AP2 domain-containing transcription factor, putative [AT1G77640.1] | NM_106412 |
| A_84_P18989 | 2.71 | down | ATMC8 | ATMC8 (METACASPASE 8); caspase [AT1G16420.1] | NM_101508 |
| A_84_P172941 | 1.88 | down | AT2G18690 | similar to unknown protein [*Arabidopsis thaliana*] (TAIR: AT2G18680.1); similar to hypothetical protein OsI_029427 [*Oryza sativa* (*indica* cultivar-group)] (GB: EAZ08195.1) [AT2G18690.1] | NM_127425 |
| A_84_P597276 | 6.80 | down | AT3G25240 | similar to unknown protein [*Arabidopsis thaliana*] (TAIR: AT3G07350.1); similar to unnamed protein product [*Vitis vinifera*] (GB: CAO39951.1); contains InterPro domain Protein of unknown function DUF506, plant (InterPro: IPR006502) [AT3G25240.1] | NM_113430 |
| A_84_P91079 | 2.51 | down | AT5G22520 | similar to unknown protein [*Arabidopsis thaliana*] (TAIR: AT5G22530.1) [AT5G22520.1] | NM_122157 |
| A_84_P22924 | 8.06 | down | AT2G47550 | pectinesterase family protein [AT2G47550.1] | NM_130323 |
| A_84_P20470 | 1.76 | down | AT1G21910 | AP2 domain-containing transcription factor family protein [AT1G21910.1] | NM_102039 |
| A_84_P15201 | 1.52 | down | ATPAO4 | ATPAO4 (POLYAMINE OXIDASE 4); amine oxidase [AT1G65840.1] | NM_105256 |
| A_84_P18566 | 1.82 | down | AT4G24570 | mitochondrial substrate carrier family protein [AT4G24570.1] | NM_118590 |
| A_84_P16568 | 2.40 | down | AT3G55840 | similar to unknown protein [*Arabidopsis thaliana*] (TAIR: AT2G40000.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT3G55840.1] | NM_115442 |
| A_84_P840068 | 2.20 | down | | GB | |
| A_84_P791120 | 4.10 | down | AT3G25240 | similar to unknown protein [*Arabidopsis thaliana*] (TAIR: AT3G07350.1); similar to unnamed protein product [*Vitis vinifera*] (GB: CAO39951.1); contains InterPro domain Protein of unknown function DUF506, plant (InterPro: IPR006502) [AT3G25240.1] | NM_113430 |
| A_84_P247395 | 1.76 | down | AT3G26470 | similar to ADR1-L1 (ADR1-LIKE 1), ATP binding/ protein binding [*Arabidopsis thaliana*] (TAIR: AT4G33300.2); similar to ADR1-L1 (ADR1-LIKE 1), ATP binding/protein binding [*Arabidopsis thaliana*] (TAIR: AT4G33300.1); similar to unnamed protein product [*Vitis vinifera*] (GB: CAO61278.1); contains InterPro domain Disease resistance, plant (InterPro: IPR014011) [AT3G26470.1] | NM_113554 |
| A_84_P12218 | 2.11 | down | AT5G64870 | similar to unknown protein [*Arabidopsis thaliana*] (TAIR: AT5G25250.1); similar to unknown protein [*Arabidopsis thaliana*] (TAIR: AT5G25260.1); similar to 80C09_16 [*Brassica rapa* subsp. *pekinensis*] (GB: AAZ41827.1); contains domain PTHR13806: SF3 (PTHR13806: SF3); contains domain PTHR13806 (PTHR13806) [AT5G64870.1] | NM_125885 |
| A_84_P19193 | 1.85 | down | AT2G37980 | similar to unknown protein [*Arabidopsis thaliana*] (TAIR: AT5G01100.1); similar to unknown protein [*Arabidopsis thaliana*] (TAIR: AT3G54100.1); similar to unnamed protein product [*Vitis vinifera*] (GB: CAO15763.1); similar to hypothetical protein | NM_129355 |

TABLE 7-continued

List of Genes Responsive to T2 treatment

| ProbeName | Fold change | Regulation | Gene Symbol | Description | Genbank Accessio |
|---|---|---|---|---|---|
| | | | | [*Vitis vinifera*] (GB: CAN72579.1); contains InterPro domain Protein of unknown function DUF246, plant (InterPro: IPR004348) [AT2G37980.1] | |
| A_84_P68014 | 1.64 | down | AT4G34150 | C2 domain-containing protein [AT4G34150.1] | NM_119578 |
| A_84_P585099 | 2.03 | down | AT5G24200 | triacylglycerol lipase [AT5G24200.1] | NM_122326 |
| A_84_P847464 | 1.63 | down | AT1G75860 | *Arabidopsis thaliana* At1g75860 mRNA sequence [AY080723] | |
| A_84_P51530 | 4.90 | down | AGP2 | AGP2 (ARABINOGALACTAN-PROTEIN 2) [AT2G22470.1] | NM_127812 |
| A_84_P21160 | 1.66 | down | AT3G10720 | pectinesterase, putative [AT3G10720.1] | NM_111908 |
| A_84_P23919 | 2.82 | down | YLS9 | YLS9 (YELLOW-LEAF-SPECIFIC GENE 9) [AT2G35980.1] | NM_129157 |
| A_84_P24128 | 1.63 | down | AT3G54150 | embryo-abundant protein-related [AT3G54150.1] | NM_115275 |
| A_84_P15802 | 1.54 | down | AT4G16500 | cysteine protease inhibitor family protein/cystatin family protein [AT4G16500.1] | NM_117748 |
| A_84_P797066 | 2.02 | down | | AYAFD87TR pooled cDNA populations *Arabidopsis thaliana* cDNA, mRNA sequence [EG438208] | |
| A_84_P262200 | 1.67 | down | AT5G43420 | zinc finger (C3HC4-type RING finger) family protein [AT5G43420.1] | NM_123708 |
| A_84_P23233 | 1.71 | down | SAG21 | SAG21 (SENESCENCE-ASSOCIATED GENE 21) [AT4G02380.1] | NM_001084877 |
| A_84_P288954 | 2.82 | down | AT2G03020 | heat shock protein-related [AT2G03020.1] | NM_201679 |
| A_84_P229729 | 2.03 | down | AT2G20142 | transmembrane receptor [AT2G20142.1] | NM_201758 |
| A_84_P14224 | 1.68 | down | GLP5 | GLP5 (GERMIN-LIKE PROTEIN 5); manganese ion binding/metal ion binding/nutrient reservoir [AT1G09560.1] | NM_100827 |
| A_84_P212828 | 5.63 | down | ATXTH18/XTH18 | ATXTH18/XTH18 (XYLOGLUCAN ENDOTRANSGLUCOSYLASE/HYDROLASE 18); hydrolase, acting on glycosyl bonds [AT4G30280.1] | NM_119174 |
| A_84_P18092 | 2.16 | down | AT1G51620 | protein kinase family protein [AT1G51620.1] | NM_104040 |
| A_84_P804241 | 2.16 | down | AT1G03370 | C2 domain-containing protein/GRAM domain-containing protein [AT1G03370.1] | NM_100219 |
| A_84_P57250 | 3.41 | down | AT1G80160 | lactoylglutathione lyase family protein/glyoxalase I family protein [AT1G80160.1] | NM_001084382 |
| A_84_P20175 | 1.70 | down | ATPAP1 | ATPAP1 (PHOSPHATIDIC ACID PHOSPHATASE 1); phosphatidate phosphatase [AT2G01180.1] | NM_201660 |
| A_84_P554567 | 2.13 | down | GATL10 | GATL10 (Galacturonosyltransferase-like 10); polygalacturonate 4-alpha-galacturonosyltransferase/transferase, transferring hexosyl groups [AT3G28340.1] | NM_113753 |
| A_84_P18416 | 4.02 | down | AT3G46080 | zinc finger (C2H2 type) family protein [AT3G46080.1] | NM_114477 |
| A_84_P54170 | 1.55 | down | AT3G57450 | similar to unnamed protein product [*Vitis vinifera*] (GB: CAO40798.1) [AT3G57450.1] | NM_115605 |
| A_84_P101246 | 2.84 | down | AT5G22530 | similar to unknown protein [*Arabidopsis thaliana*] (TAIR: AT5G22520.1) [AT5G22530.1] | NM_122158 |
| A_84_P14274 | 3.74 | down | AT1G52690 | late embryogenesis abundant protein, putative/LEA protein, putative [AT1G52690.1] | NM_202280 |
| A_84_P14505 | 3.16 | down | AT2G32140 | transmembrane receptor [AT2G32140.1] | NM_128773 |
| A_84_P818437 | 4.67 | down | CML37/CML39 | CML37/CML39; calcium ion binding [AT5G42380.1] | NM_123603 |
| A_84_P249785 | 1.56 | down | ATVAMP723 | ATVAMP723 (*Arabidopsis thaliana* vesicle-associated membrane protein 723) [AT2G33110.1] | NM_179870 |
| A_84_P18557 | 3.46 | down | AT4G22470 | protease inhibitor/seed storage/lipid transfer protein (LTP) family protein [AT4G22470.1] | NM_118373 |
| A_84_P11470 | 1.72 | down | AT1G66400 | calmodulin-related protein, putative [AT1G66400.1] | NM_105311 |
| A_84_P15329 | 1.63 | down | AT2G40000 | similar to unknown protein [*Arabidopsis thaliana*] (TAIR: AT3G55840.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] | NM_129558 |
| A_84_P17859 | 3.89 | down | TCH4 | TCH4 (TOUCH 4); hydrolase, acting on glycosyl bonds/xyloglucan:xyloglucosyl transferase [AT5G57560.1] | NM_125137 |
| A_84_P813874 | 1.77 | down | AtNUDT7 | AtNUDT7 (*ARABIDOPSIS THALIANA* NUDIX HYDROLASE HOMOLOG 7); hydrolase [AT4G12720.2] | NM_179036 |
| A_84_P110752 | 1.59 | down | AGP12 | AGP12 (ARABINOGALACTAN PROTEIN 12) [AT3G13520.1] | NM_112198 |
| A_84_P713547 | 1.70 | down | AT1G52618 | *Arabidopsis thaliana* mRNA for hypothetical protein, partial cds, clone: RAFL15-08-C02 [AK228475] | |
| A_84_P810381 | 2.24 | down | HSP91 | HSP91 (Heat shock protein 91) [AT1G79930.1] | NM_106642 |
| A_84_P297064 | 5.12 | down | ATXTH17 | ATXTH17 (XYLOGLUCAN ENDOTRANSGLUCOSYLASE/HYDROLASE 17); hydrolase, acting on glycosyl bonds [AT1G65310.1] | NM_105205 |

TABLE 7-continued

List of Genes Responsive to T2 treatment

| ProbeName | Fold change | Regulation | Gene Symbol | Description | Genbank Accessio |
|---|---|---|---|---|---|
| A_84_P17111 | 1.95 | down | AT1G02820 | late embryogenesis abundant 3 family protein/LEA3 family protein [AT1G02820.1] | NM_100163 |
| A_84_P843221 | 2.08 | down | GB | | |
| A_84_P582920 | 3.01 | down | BAP2 | BAP2 (BON ASSOCIATION PROTEIN 2) [AT2G45760.1] | NM_130139 |
| A_84_P14106 | 2.10 | down | AGP1 | AGP1 (ARABINOGALACTAN-PROTEIN 1) [AT5G64310.1] | NM_125827 |
| A_84_P17614 | 2.98 | down | CRK13/HIG1 | CRK13/HIG1; kinase [AT4G23210.1] | NM_001084966 |
| A_84_P763881 | 1.53 | down | AT4G20830 | FAD-binding domain-containing protein [AT4G20830.1] | NM_202851 |
| A_84_P22532 | 1.72 | down | AT5G41740 | disease resistance protein (TIR-NBS-LRR class), putative [AT5G41740.1] | NM_123539 |
| A_84_P97916 | 3.01 | down | AT4G29780 | similar to unknown protein [*Arabidopsis thaliana*] (TAIR: AT5G12010.1); similar to unnamed protein product [*Vitis vinifera*] (GB: CAO43835.1); contains domain PTHR22930 (PTHR22930) [AT4G29780.1] | NM_119124 |
| A_84_P10224 | 1.67 | down | TCH2 | TCH2 (TOUCH 2); calcium ion binding [AT5G37770.1] | NM_123136 |
| A_84_P22854 | 1.62 | down | AT1G51790 | kinase [AT1G51790.1] | NM_104058 |
| A_84_P861742 | 1.94 | down | | NUDT7_ARATH (Q9SU14) Nudix hydrolase 7 (AtNUDT7) (ADP-ribose pyrophosphatase) (NADH pyrophosphatase), partial (27%) [TC313556] | |
| A_84_P148418 | 2.00 | down | MT1C | MT1C (metallothionein 1C) [AT1G07610.1] | NM_100634 |
| A_84_P20394 | 4.50 | down | AT4G02170 | similar to unknown protein [*Arabidopsis thaliana*] (TAIR: AT5G38700.1); similar to unnamed protein product [*Vitis vinifera*] (GB: CAO40081.1) [AT4G02170.1] | NM_116449 |
| A_84_P16642 | 1.71 | down | AtNUDT7 | AtNUDT7 (*ARABIDOPSIS THALIANA* NUDIX HYDROLASE HOMOLOG 7); hydrolase/nucleoside-diphosphatase [AT4G12720.1] | NM_179036 |
| A_84_P793354 | 1.74 | down | AT1G25400 | *Arabidopsis thaliana* mRNA for hypothetical protein, complete cds, clone: RAFL21-85-I12 [AK229804] | |
| A_84_P762507 | 3.37 | down | AT3G25573 | unknown protein [AT3G25573.1] | NM_001125226 |
| A_84_P823870 | 1.59 | down | HYH | HYH (HY5-HOMOLOG); DNA binding/transcription factor [AT3G17609.3] | NM_001035640 |
| A_84_P16437 | 1.87 | down | AT3G09870 | auxin-responsive family protein [AT3G09870.1] | NM_111822 |
| A_84_P20045 | 2.52 | down | AT1G57630 | disease resistance protein (TIR class), putative [AT1G57630.1] | NM_104560 |
| A_84_P22442 | 1.69 | down | AT-HSFA3 | AT-HSFA3 (*Arabidopsis thaliana* heat shock transcription factor A3); DNA binding/transcription factor [AT5G03720.1] | NM_120453 |
| A_84_P833734 | 1.77 | down | | Q27GL6_ARATH (Q27GL6) Protein At2g07724, complete [TC304412] | |
| A_84_P503876 | 1.72 | down | AT2G27660 | DC1 domain-containing protein [AT2G27660.1] | NM_128325 |
| A_84_P268090 | 1.81 | down | AT2G01300 | similar to unknown protein [*Arabidopsis thaliana*] (TAIR: AT1G15010.1); similar to unnamed protein product [*Vitis vinifera*] (GB: CAO42242.1) [AT2G01300.1] | NM_126191 |
| A_84_2175491 | 1.99 | down | SRO5 | SRO5 (SIMILAR TO RCD ONE 5); NAD+ ADP-ribosyltransferase [AT5G62520.1] | NM_203252 |
| A_84_P821763 | 2.01 | down | | | |
| A_84_P209868 | 2.94 | down | AT2G32130 | similar to UNE1 (unfertilized embryo sac 1) [*Arabidopsis thaliana*] (TAIR: AT1G29300.1); similar to unnamed protein product [*Vitis vinifera*] (GB: CAO48018.1); contains InterPro domain Protein of unknown function DUF641, plant (InterPro: IPR006943) [AT2G32130.1] | NM_128772 |
| A_84_P18553 | 1.59 | down | B120 | B120; protein kinase/sugar binding [AT4G21390.1] | NM_118259 |
| A_84_P168493 | 1.54 | down | AT3G46620 | zinc finger (C3HC4-type RING finger) family protein [AT3G46620.1] | NM_114529 |
| A_84_P715787 | 1.96 | down | AT1G32928 | similar to unknown protein [*Arabidopsis thaliana*] (TAIR: AT1G32920.1) [AT1G32928.1] | NM_001036055 |
| A_84_P862479 | 4.27 | down | | | |
| A_84_P10996 | 3.10 | down | AT4G23070 | rhomboid family protein [AT4G23070.1] | NM_118436 |
| A_84_P762701 | 20.29 | down | AT3G56891 | metal ion binding [AT3G56891.1] | NM_001125377 |
| A_84_P816512 | 1.94 | down | AT2G18690 | similar to unknown protein [*Arabidopsis thaliana*] (TAIR: AT2G18680.1); similar to hypothetical protein OsI_029427 [*Oryza sativa* (indica cultivar-group)] (GB: EAZ08195.1) [AT2G18690.1] | NM_127425 |
| A_84_P17343 | 2.23 | down | ATERF13/EREBP | ATERF13/EREBP (ETHYLENE-RESPONSIVE ELEMENT BINDING FACTOR 13); DNA binding/transcription factor [AT2G44840.1] | NM_130048 |
| A_84_P14186 | 1.73 | down | AT1G05000 | tyrosine specific protein phosphatase family protein [AT1G05000.1] | NM_100379 |

TABLE 7-continued

List of Genes Responsive to T2 treatment

| ProbeName | Fold change | Regulation | Gene Symbol | Description | Genbank Accessio |
|---|---|---|---|---|---|
| A_84_P19363 | 3.52 | down | ATHSP17.4 | ATHSP17.4 (*Arabidopsis thaliana* heat shock protein 17.4) [AT3G46230.1] | NM_114492 |
| A_84_P10964 | 2.16 | down | AT4G11190 | disease resistance-responsive family protein/dirigent family protein [AT4G11190.1] | NM_117190 |
| A_84_P21264 | 1.84 | down | BT2 | BT2 (BTB AND TAZ DOMAIN PROTEIN 2); protein binding/transcription factor/transcription regulator [AT3G48360.1] | NM_114697 |
| A_84_P11694 | 3.23 | down | AT3G01830 | calmodulin-related protein, putative [AT3G01830.1] | NM_111049 |
| A_84_P23913 | 1.82 | down | AT2G38870 | protease inhibitor, putative [AT2G38870.1] | NM_129444 |
| A_84_P12815 | 1.80 | down | ATGSTF13 | ATGSTF13 (*Arabidopsis thaliana* Glutathione S-transferase (class phi) 13); glutathione transferase [AT3G62760.1] | NM_116141 |
| A_84_P287570 | 1.67 | down | AT5G55180 | glycosyl hydrolase family 17 protein [AT5G55180.1] | NM_124900 |
| A_84_P849049 | 3.70 | down | | NM_113740 PMZ {*Arabidopsis thaliana*} (exp = −1; wgp = 0; cg = 0), partial (76%) [TC302412] | |
| A_84_P18076 | 2.29 | down | GA4H | GA4H (gibberellin 3 beta-hydroxylase); gibberellin 3-beta-dioxygenase [AT1G80340.1] | NM_106683 |
| A_84_P769565 | 1.77 | down | AT5G44585 | unknown protein [AT5G44585.1] | NM_001125900 |
| A_84_P21001 | 2.48 | down | AT1G44130 | nucellin protein, putative [AT1G44130.1] | NM_103539 |
| A_84_P22181 | 3.47 | down | PMZ | PMZ; zinc ion binding [AT3G28210.1] | NM_113740 |
| A_84_P811255 | 1.59 | down | AGP12 | AGP12 (ARABINOGALACTAN PROTEIN 12) [AT3G13520.1] | NM_112198 |
| A_84_P557122 | 3.65 | down | AT2G45130 | SPX (SYG1/Pho81/XPR1) domain-containing protein [AT2G45130.1] | NM_130076 |
| A_84_P844006 | 5.18 | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] | NM_179772 |
| A_84_P597566 | 2.14 | down | SLAH3 | SLAH3 (SLAC1 HOMOLOGUE 3); transporter [AT5G24030.1] | NM_122308 |
| A_84_P810552 | 1.87 | down | BT2 | BT2 (BTB AND TAZ DOMAIN PROTEIN 2); protein binding/transcription factor/transcription regulator [AT3G48360.1] | NM_114697 |
| A_84_P823988 | 2.07 | down | SKS9 | SKS9 (SKU5 Similar 9); copper ion binding/oxidoreductase [AT4G38420.1] | NM_120004 |
| A_84_P217688 | 1.89 | down | AT1G76600 | similar to unknown protein [*Arabidopsis thaliana*] (TAIR: AT1G21010.1); similar to hypothetical protein [*Vitis vinifera*] (GB: CAN67638.1) [AT1G76600.1] | NM_106310 |
| A_84_P16848 | 1.83 | down | AT5G39580 | peroxidase, putative [AT5G39580.1] | NM_123320 |
| A_84_P537920 | 1.55 | down | AT4G33985 | similar to unknown protein [*Arabidopsis thaliana*] (TAIR: AT2G15590.2); similar to unnamed protein product [*Vitis vinifera*] (GB: CAO71847.1); contains InterPro domain Protein of unknown function DUF1685 (InterPro: IPR012881) [AT4G33985.1] | NM_119560 |
| A_84_P21390 | 2.60 | down | ATGA2OX8 | ATGA2OX8 (GIBBERELLIN 2-OXIDASE 8); gibberellin 2-beta-dioxygenase [AT4G21200.1] | NM_118239 |
| A_84_P800901 | 2.16 | down | AT1G66160 | U-box domain-containing protein [AT1G66160.1] | NM_105287 |
| A_84_P65254 | 2.05 | down | AT5G60260 | unknown protein [AT5G60260.1] | NM_125419 |
| A_84_P839984 | 1.87 | down | AT1G63580 | protein kinase-related [AT1G63580.1] | NM_105036 |
| A_84_P156125 | 2.95 | down | BAP1 | BAP1 (BON ASSOCIATION PROTEIN 1) [AT3G61190.1] | NM_115983 |
| A_84_P819549 | 1.87 | down | AT5G41740 | disease resistance protein (TIR-NBS-LRR class), putative [AT5G41740.1] | NM_123539 |
| A_84_P12896 | 1.85 | down | SHB1 | SHB1 (SHORT HYPOCOTYL UNDER BLUE1) [AT4G25350.1] | NM_118667 |
| A_84_P19028 | 4.36 | down | ORA47 | ORA47; DNA binding/transcription factor [AT1G74930.1] | NM_106151 |
| A_84_P766473 | 3.50 | down | AT5G25260 | similar to unknown protein [*Arabidopsis thaliana*] (TAIR: AT5G25250.1); similar to unknown protein [*Arabidopsis thaliana*] (TAIR: AT5G64870.1); similar to unnamed protein product [*Vitis vinifera*] (GB: CAO44306.1); similar to hypothetical protein [*Vitis vinifera*] (GB: CAN77054.1); similar to 80C09_16 [*Brassica rapa* subsp. *pekinensis*] (GB: AAZ41827.1); contains domain PTHR13806: SF3 (PTHR13806: SF3); contains domain PTHR13806 (PTHR13806) [AT5G25260.1] | NM_122435 |
| A_84_P13393 | 1.50 | down | AT1G66090 | disease resistance protein (TIR-NBS class), putative [AT1G66090.1] | NM_105280 |
| A_84_P14480 | 3.08 | down | AT2G38250 | DNA-binding protein-related [AT2G38250.1] | NM_129382 |
| A_84_P835500 | 1.72 | down | AT3G07400 | lipase class 3 family protein [AT3G07400.1] | NM_111619 |
| A_84_P20998 | 5.03 | down | PHI-1 | PHI-1 (PHOSPHATE-INDUCED 1) [AT1G35140.1] | NM_103210 |
| A_84_P22991 | 1.63 | down | AT2G37430 | zinc finger (C2H2 type) family protein (ZAT11) [AT2G37430.1] | NM_129298 |

TABLE 7-continued

List of Genes Responsive to T2 treatment

| ProbeName | Fold change | Regulation | Gene Symbol | Description | Genbank Accessio |
|---|---|---|---|---|---|
| A_84_P11921 | 1.61 | down | IP5PII | IP5PII (INOSITOL POLYPHOSPHATE 5-PHOSPHATASE II); inositol-polyphosphate 5-phosphatase [AT4G18010.1] | NM_179071 |
| A_84_P13546 | 2.96 | down | AT2G42360 | zinc finger (C3HC4-type RING finger) family protein [AT2G42360.1] | NM_129798 |
| A_84_P13086 | 1.58 | down | AT5G44910 | Toll-Interleukin-Resistance (TIR) domain-containing protein [AT5G44910.1] | NM_123859 |
| A_84_P16923 | 2.53 | down | RHL41 | RHL41 (RESPONSIVE TO HIGH LIGHT 41); nucleic acid binding/transcription factor/zinc ion binding [AT5G59820.1] | NM_125374 |
| A_84_P230389 | 2.21 | down | AT3G21080 | ABC transporter-related [AT3G21080.1] | NM_113002 |
| A_84_P787353 | 1.78 | down | AT5G17350 | similar to unknown protein [Arabidopsis thaliana] (TAIR: AT3G03280.1); similar to unknown [Populus trichocarpa] (GB: ABK95625.1) [AT5G17350.1] | NM_121741 |
| A_84_P22039 | 1.64 | down | AT2G31010 | protein kinase family protein [AT2G31010.1] | NM_128655 |
| A_84_P17628 | 4.77 | down | ACS7 | ACS7 (1-Amino-cyclopropane-1-carboxylate synthase 7); 1-aminocyclopropane-1-carboxylate synthase [AT4G26200.1] | NM_118753 |
| A_84_P599288 | 1.62 | down | WAVE3 | WAVE3 [AT5G01730.1] | NM_120251 |
| A_84_P790938 | 1.78 | down | AT5G65130 | AP2 domain-containing transcription factor, putative [AT5G65130.1] | NM_125912 |
| A_84_P740606 | 1.69 | down | | NM_125960 metalloendopeptidase {Arabidopsis thaliana} (exp = −1; wgp = 0; cg = 0), complete [TC295240] | |
| A_84_P13990 | 1.88 | down | AT5G26010 | protein serine/threonine phosphatase [AT5G26010.1] | NM_122502 |
| A_84_P275730 | 1.77 | down | TMAC2 | TMAC2 (TWO OR MORE ABRES-CONTAINING GENE 2) [AT3G02140.1] | NM_111081 |
| A_84_P836893 | 1.73 | down | | Encodes an unknown protein. This gene is regulated by AtSIG6 transcriptionally. [ATCG00860.1] | |
| A_84_P21874 | 2.02 | down | STZ | STZ (SALT TOLERANCE ZINC FINGER); nucleic acid binding/transcription factor/zinc ion binding [AT1G27730.1] | NM_102538 |
| A_84_P23448 | 2.46 | down | AT5G25910 | disease resistance family protein [AT5G25910.1] | NM_122492 |
| A_84_P21253 | 2.50 | down | AT3G45880 | similar to transcription factor jumonji (jmjC) domain-containing protein [Arabidopsis thaliana] (TAIR: AT5G19840.1); similar to unnamed protein product [Vitis vinifera] (GB: CAO63727.1); contains InterPro domain Transcription factor jumonji/aspartyl beta-hydroxylase (InterPro: IPR003347) [AT3G45880.1] | NM_114457 |
| A_84_P23754 | 3.14 | down | AIG1 | AIG1 (AVRRPT2-INDUCED GENE 1); GTP binding [AT1G33960.1] | NM_103118 |
| A_84_P567134 | 2.46 | down | AT4G27657 | similar to unknown protein [Arabidopsis thaliana] (TAIR: AT4G27652.1) [AT4G27657.1] | NM_118904 |
| A_84_P21931 | 1.88 | down | ATERF11/ERF11 | ATERF11/ERF11 (ERF domain protein 11); DNA binding/transcription factor/transcription repressor [AT1G28370.1] | NM_102603 |
| A_84_P15304 | 1.55 | down | ATPP2-A5 | ATPP2-A5; carbohydrate binding [AT1G65390.1] | NM_202365 |
| A_84_P869292 | 1.92 | down | ATERF-1 | ATERF-1 (ETHYLENE RESPONSIVE ELEMENT BINDING FACTOR 1); DNA binding/transcription activator/transcription factor [AT4G17500.1] | NM_117855 |
| A_84_P16770 | 1.76 | down | AT5G04970 | pectinesterase, putative [AT5G04970.1] | NM_120579 |
| A_84_P10949 | 2.92 | down | AtMYB74 | AtMYB74 (myb domain protein 74); DNA binding/transcription factor [AT4G05100.1] | NM_116749 |
| A_84_P15331 | 2.09 | down | AT2G43620 | chitinase, putative [AT2G43620.1] | NM_129924 |
| A_84_P269630 | 7.00 | down | AT2G27505 | similar to F-box family protein [Arabidopsis thaliana] (TAIR: AT5G44950.1); contains InterPro domain FBD (InterPro: IPR013596); contains InterPro domain FBD-like (InterPro: IPR006566) [AT2G27505.1] | NM_179772 |
| A_84_P869713 | 1.63 | down | AT5G52760 | heavy-metal-associated domain-containing protein [AT5G52760.1] | NM_124654 |
| A_84_P160753 | 1.63 | down | AT2G41800 | similar to unknown protein [Arabidopsis thaliana] (TAIR: AT2G41810.1); similar to unnamed protein product [Vitis vinifera] (GB: CAO23583.1); similar to hypothetical protein [Vitis vinifera] (GB: CAN80832.1); contains InterPro domain Protein of unknown function DUF642 (InterPro: IPR006946); contains InterPro domain Galactose-binding like (InterPro: IPR008979) [AT2G41800.1] | NM_129744 |
| A_84_P17802 | 1.62 | down | ATCHX18 | ATCHX18 (cation/hydrogen exchanger 18); monovalent cation: proton antiporter [AT5G41610.1] | NM_123525 |
| A_84_P811555 | 2.07 | down | AT2G05915 | 11065864 CERES-AN65 Arabidopsis thaliana cDNA clone 1345449 5', mRNA sequence [DR262979] | |

TABLE 7-continued

List of Genes Responsive to T2 treatment

| ProbeName | Fold change | Regulation | Gene Symbol | Description | Genbank Accessio |
|---|---|---|---|---|---|
| A_84_P844663 | 1.51 | down | | O23614_ARATH (O23614) PSII D1 protein processing enzyme (AT4g17740/dl4905c), complete [TC283823] | |
| A_84_P19559 | 1.87 | down | AT1G15010 | similar to unknown protein [*Arabidopsis thaliana*] (TAIR: AT2G01300.1); similar to unnamed protein product [*Vitis vinifera*] (GB: CAO42242.1) [AT1G15010.1] | NM_101370 |
| A_84_P821712 | 5.49 | down | PHI-1 | PHI-1 (PHOSPHATE-INDUCED 1) [AT1G35140.1] | NM_103210 |
| A_84_P14159 | 1.53 | down | AT2G07705 | unknown protein [AT2G07705.1] | NM_126749 |
| A_84_P573393 | 5.33 | down | AT4G27654 | unknown protein [AT4G27654.1] | NM_118903 |
| A_84_P19362 | 3.22 | down | ZAT7 | ZAT7; nucleic acid binding/transcription factor/zinc ion binding [AT3G46090.1] | NM_114478 |
| A_84_P13197 | 2.02 | down | AT5G09470 | mitochondrial substrate carrier family protein [AT5G09470.1] | NM_120984 |
| A_84_P18823 | 1.97 | down | AT5G61560 | protein kinase family protein [AT5G61560.1] | NM_125549 |
| A_84_P12981 | 1.54 | down | AT5G02430 | WD-40 repeat family protein [AT5G02430.1] | NM_120321 |
| A_84_P272600 | 7.36 | down | AT5G21960 | AP2 domain-containing transcription factor, putative [AT5G21960.1] | NM_147879 |
| A_84_P754300 | 2.43 | down | AT1G65481 | other RNA [AT1G65481.1] | NR_022368 |
| A_84_P10496 | 1.69 | down | ATUGT85A1/UGT85A1 | ATUGT85A1/UGT85A1 (UDP-GLUCOSYL TRANSFERASE 85A1); UDP-glycosyltransferase/glucuronosyltransferase/transferase, transferring glycosyl groups/transferase, transferring hexosyl groups [AT1G22400.1] | NM_102089 |
| A_84_P20057 | 1.97 | down | AT1G63580 | protein kinase-related [AT1G63580.1] | NM_105036 |
| A_84_P805748 | 1.70 | down | CPK29 | CPK29 (calcium-dependent protein kinase 29); calmodulin-dependent protein kinase/kinase [AT1G76040.2] | NM_202421 |
| A_84_P12358 | 1.58 | down | HSR8/MUR4/UXE1 | HSR8/MUR4/UXE1 (MURUS 4); UDP-arabinose 4-epimerase/catalytic [AT1G30620.1] | NM_001036041 |
| A_84_P800627 | 1.62 | down | | *Arabidopsis thaliana* unknown mRNA transcribed from the opposite strand of At2g02700 [DQ077902] | |
| A_84_P12186 | 1.59 | down | AT5G57480 | AAA-type ATPase family protein [AT5G57480.1] | NM_125129 |
| A_84_P15939 | 1.72 | down | AtMYB111 | AtMYB111 (myb domain protein 111); DNA binding/transcription factor [AT5G49330.1] | NM_124310 |
| A_84_P601466 | 1.77 | down | AT1G70910 | zinc finger (C3HC4-type RING finger) family protein [AT1G70910.1] | NM_105759 |
| A_84_P870644 | 2.34 | down | AT1G24380 | similar to unknown protein [*Arabidopsis thaliana*] (TAIR: AT4G10230.1); similar to conserved hypothetical protein [*Asparagus officinalis*] (GB: ABB55300.1) [AT1G24380.1] | NM_102284 |
| A_84_P579612 | 2.21 | down | AT4G27652 | similar to unknown protein [*Arabidopsis thaliana*] (TAIR: AT4G27657.1) [AT4G27652.1] | NM_118902 |
| A_84_P23274 | 1.91 | down | AT1G29290 | similar to hypothetical protein [*Vitis vinifera*] (GB: CAN69942.1) [AT1G29290.1] | NM_102669 |
| A_84_P561097 | 1.59 | down | AT5G46295 | unknown protein [AT5G46295.1] | NM_123999 |
| A_84_P21275 | 1.72 | down | AT3G50930 | AAA-type ATPase family protein [AT3G50930.1] | NM_114953 |
| A_84_P758556 | 2.60 | down | AT2G35658 | similar to unknown protein [*Arabidopsis thaliana*] (TAIR: AT4G16840.1); similar to unnamed protein product [*Vitis vinifera*] (GB: CAO22322.1) [AT2G35658.1] | NM_001124975 |
| A_84_P286120 | 1.56 | down | CYP707A1 | CYP707A1 (cytochrome P450, family 707, subfamily A, polypeptide 1); oxygen binding [AT4G19230.1] | NM_202845 |
| A_84_P166733 | 1.69 | down | AT5G17350 | similar to unknown protein [*Arabidopsis thaliana*] (TAIR: AT3G03280.1); similar to unknown [*Populus trichocarpa*] (GB: ABK95625.1) [AT5G17350.1] | NM_121741 |
| A_84_P220868 | 3.15 | down | AT2G17740 | DC1 domain-containing protein [AT2G17740.1] | NM_127328 |
| A_84_P802310 | 2.02 | down | | 205o16.p1 AtM1 *Arabidopsis thaliana* cDNA clone MPMGp2011O16205 5-PRIME, mRNA sequence [CK120817] | |
| A_84_P23502 | 7.61 | down | ATXTH20 | ATXTH20 (XYLOGLUCAN ENDOTRANSGLUCOSYLASE/HYDROLASE 20); hydrolase, acting on glycosyl bonds [AT5G48070.1] | NM_124181 |
| A_84_P809218 | 1.75 | down | AT4G28760 | similar to unknown protein [*Arabidopsis thaliana*] (TAIR: AT2G20240.1); similar to hypothetical protein [*Vitis vinifera*] (GB: CAN81514.1); contains domain PTHR21726: SF7 (PTHR21726: SF7); contains domain PTHR21726 (PTHR21726) [AT4G28760.1] | NM_119020 |
| A_84_P595805 | 1.79 | down | AT5G36925 | similar to unknown protein [*Arabidopsis thaliana*] (TAIR: AT5G36920.1) [AT5G36925.1] | NM_180586 |
| A_84_P17320 | 2.16 | down | ATCNGC14 | ATCNGC14 (cyclic nucleotide gated channel 14); calmodulin binding/cyclic nucleotide binding/ion channel [AT2G24610.1] | NM_179725 |

TABLE 7-continued

List of Genes Responsive to T2 treatment

| ProbeName | Fold change | Regulation | Gene Symbol | Description | Genbank Accessio |
|---|---|---|---|---|---|
| A_84_P23217 | 1.77 | down | ATXT1 | ATXT1; UDP-xylosyltransferase/transferase/transferase, transferring glycosyl groups [AT3G62720.1] | NM_116137 |
| A_84_P21341 | 1.90 | down | ATPMEPCRB | ATPMEPCRB; pectinesterase [AT4G02330.1] | NM_116466 |
| A_84_P140849 | 2.34 | down | AT1G32920 | similar to unknown protein [Arabidopsis thaliana] (TAIR: AT1G32928.1) [AT1G32920.1] | NM_103025 |
| A_84_P737368 | 2.40 | down | AT1G36622 | similar to unknown protein [Arabidopsis thaliana] (TAIR: AT1G36640.1) [AT1G36622.1] | NM_001084200 |
| A_84_P158205 | 2.76 | down | AT1G22470 | similar to unknown protein [Arabidopsis thaliana] (TAIR: AT1G72240.1) [AT1G22470.1] | NM_102096 |
| A_84_P576295 | 1.57 | down | AT1G03106 | unknown protein [AT1G03106.1] | NM_202021 |
| A_84_P829388 | 1.77 | down | MAPKKK13 | MAPKKK13 (Mitogen-activated protein kinase kinase kinase 13); kinase [AT1G07150.1] | NM_100589 |
| A_84_P15812 | 4.53 | down | AT5G01380 | transcription factor [AT5G01380.1] | NM_120216 |
| A_84_P531612 | 2.29 | down | AT4G04745 | similar to unknown protein [Arabidopsis thaliana] (TAIR: AT4G21902.1); similar to hypothetical protein [Vitis vinifera] (GB: CAN76789.1) [AT4G04745.1] | NM_148231 |
| A_84_P837475 | 2.16 | down | AT2G01130 | ATP binding/helicase/nucleic acid binding [AT2G01130.1] | NM_126175 |
| A_84_P16997 | 3.95 | down | AT1G20520 | similar to unknown protein [Arabidopsis thaliana] (TAIR: AT1G76210.1); similar to hypothetical protein [Vitis vinifera] (GB: CAN69930.1); contains InterPro domain Protein of unknown function DUF241, plant (InterPro: IPR004320) [AT1G20520.1] | NM_101902 |

TABLE 8

List of Genes Responsive to T1 and T2

| ProbeName | Fold change | Comparison | Regulation | Gene Symbol | Description |
|---|---|---|---|---|---|
| A_84_P102986 | 2.29 | T1 vs control | down | AT2G27080 | harpin-induced protein-related/HIN1-related/harpin-responsive protein-related [AT2G27080.1] |
| A_84_P102986 | 2.46 | T2 vs control | down | AT2G27080 | harpin-induced protein-related/HIN1-related/harpin-responsive protein-related [AT2G27080.1] |
| A_84_P10496 | 1.59 | T1 vs control | down | ATUGT85A1/UGT85A1 | ATUGT85A1/UGT85A1 (UDP-GLUCOSYL TRANSFERASE 85A1); UDP-glycosyltransferase/glucuronosyltransferase/transferase, transferring glycosyl groups/transferase, transferring hexosyl groups [AT1G22400.1] |
| A_84_P10496 | 1.69 | T2 vs control | down | ATUGT85A1/UGT85A1 | ATUGT85A1/UGT85A1 (UDP-GLUCOSYL TRANSFERASE 85A1); UDP-glycosyltransferase/glucuronosyltransferase/transferase, transferring glycosyl groups/transferase, transferring hexosyl groups [AT1G22400.1] |
| A_84_P10528 | 2.41 | T2 vs control | down | AT1G51800 | leucine-rich repeat protein kinase, putative [AT1G51800.1] |
| A_84_P10528 | 2.52 | T1 vs control | down | AT1G51800 | leucine-rich repeat protein kinase, putative [AT1G51800.1] |
| A_84_P113182 | 3.34 | T2 vs control | down | AT4G39670 | glycolipid binding/glycolipid transporter [AT4G39670.1] |
| A_84_P113182 | 3.67 | T1 vs control | down | AT4G39670 | glycolipid binding/glycolipid transporter [AT4G39670.1] |
| A_84_P11694 | 3.23 | T2 vs control | down | AT3G01830 | calmodulin-related protein, putative [AT3G01830.1] |
| A_84_P11694 | 3.62 | T1 vs control | down | AT3G01830 | calmodulin-related protein, putative [AT3G01830.1] |
| A_84_P11921 | 1.57 | T1 vs control | down | IP5PII | IP5PII (INOSITOL POLYPHOSPHATE 5-PHOSPHATASE II); inositol-polyphosphate 5-phosphatase [AT4G18010.1] |
| A_84_P11921 | 1.61 | T2 vs control | down | IP5PII | IP5PII (INOSITOL POLYPHOSPHATE 5-PHOSPHATASE II); inositol-polyphosphate 5-phosphatase [AT4G18010.1] |

TABLE 8-continued

List of Genes Responsive to T1 and T2

| ProbeName | Fold change | Comparison | Regulation | Gene Symbol | Description |
|---|---|---|---|---|---|
| A_84_P12056 | 2.95 | T1 vs control | down | AT5G08030 | glycerophosphoryl diester phosphodiesterase family protein [AT5G08030.1] |
| A_84_P12056 | 3.49 | T2 vs control | down | AT5G08030 | glycerophosphoryl diester phosphodiesterase family protein [AT5G08030.1] |
| A_84_P12186 | 1.59 | T1 vs control | down | AT5G57480 | AAA-type ATPase family protein [AT5G57480.1] |
| A_84_P12186 | 1.59 | T2 vs control | down | AT5G57480 | AAA-type ATPase family protein [AT5G57480.1] |
| A_84_P12212 | 2.90 | T1 vs control | down | AT1G56060 | similar to unknown protein [Arabidopsis thaliana] (TAIR: AT2G32190.1); similar to unnamed protein product [Vitis vinifera] (GB: CAO68639.1); contains domain PD188784 (PD188784) [AT1G56060.1] |
| A_84_P12212 | 5.26 | T2 vs control | down | AT1G56060 | similar to unknown protein [Arabidopsis thaliana] (TAIR: AT2G32190.1); similar to unnamed protein product [Vitis vinifera] (GB: CAO68639.1); contains domain PD188784 (PD188784) [AT1G56060.1] |
| A_84_P12218 | 1.72 | T1 vs control | down | AT5G64870 | similar to unknown protein [Arabidopsis thaliana] (TAIR: AT5G25250.1); similar to unknown protein [Arabidopsis thaliana] (TAIR: AT5G25260.1); similar to 80C09_16 [Brassica rapa subsp. pekinensis] (GB: AAZ41827.1); contains domain PTHR13806: SF3 (PTHR13806: SF3); contains domain PTHR13806 (PTHR13806) [AT5G64870.1] |
| A_84_P12218 | 2.11 | T2 vs control | down | AT5G64870 | similar to unknown protein [Arabidopsis thaliana] (TAIR: AT5G25250.1); similar to unknown protein [Arabidopsis thaliana] (TAIR: AT5G25260.1); similar to 80C09_16 [Brassica rapa subsp. pekinensis] (GB: AAZ41827.1); contains domain PTHR13806: SF3 (PTHR13806: SF3); contains domain PTHR13806 (PTHR13806) [AT5G64870.1] |
| A_84_P12896 | 1.85 | T2 vs control | down | SHB1 | SHB1 (SHORT HYPOCOTYL UNDER BLUE1) [AT4G25350.1] |
| A_84_P12896 | 1.92 | T1 vs control | down | SHB1 | SHB1 (SHORT HYPOCOTYL UNDER BLUE1) [AT4G25350.1] |
| A_84_P13013 | 1.60 | T2 vs control | down | AT1G18380 | Identical to Uncharacterized protein At1g18380 precursor [Arabidopsis thaliana] (GB: Q5BQ05; GB: Q5Q0G6; GB: Q8RX30; GB: Q9LPQ6); similar to unknown protein [Arabidopsis thaliana] (TAIR: AT1G67025.1); similar to unnamed protein product [Vitis vinifera] (GB: CAO68096.1) [AT1G18380.1] |
| A_84_P13013 | 1.64 | T1 vs control | down | AT1G18380 | Identical to Uncharacterized protein At1g18380 precursor [Arabidopsis thaliana] (GB: Q5BQ05; GB: Q5Q0G6; GB: Q8RX30; GB: Q9LPQ6); similar to unknown protein [Arabidopsis thaliana] (TAIR: AT1G67025.1); similar to unnamed protein product [Vitis vinifera] (GB: CAO68096.1) [AT1G18380.1] |
| A_84_P13077 | 5.07 | T2 vs control | down | CML37/CML39 | CML37/CML39; calcium ion binding [AT5G42380.1] |
| A_84_P13077 | 5.54 | T1 vs control | down | CML37/CML39 | CML37/CML39; calcium ion binding [AT5G42380.1] |
| A_84_P13086 | 1.58 | T2 vs control | down | AT5G44910 | Toll-Interleukin-Resistance (TIR) domain-containing protein [AT5G44910.1] |
| A_84_P13086 | 1.69 | T1 vs control | down | AT5G44910 | Toll-Interleukin-Resistance (TIR) domain-containing protein [AT5G44910.1] |
| A_84_P13104 | 2.63 | T2 vs control | down | WRKY48 | WRKY48 (WRKY DNA-binding protein 48); transcription factor [AT5G49520.1] |
| A_84_P13104 | 2.79 | T1 vs control | down | WRKY48 | WRKY48 (WRKY DNA-binding protein 48); transcription factor [AT5G49520.1] |

TABLE 8-continued

List of Genes Responsive to T1 and T2

| ProbeName | Fold change | Comparison | Regulation | Gene Symbol | Description |
|---|---|---|---|---|---|
| A_84_P13393 | 1.50 | T2 vs control | down | AT1G66090 | disease resistance protein (TIR-NBS class), putative [AT1G66090.1] |
| A_84_P13393 | 2.02 | T1 vs control | down | AT1G66090 | disease resistance protein (TIR-NBS class), putative [AT1G66090.1] |
| A_84_P13494 | 2.59 | T2 vs control | down | AT2G36690 | oxidoreductase, 2OG-Fe(II) oxygenase family protein [AT2G36690.1] |
| A_84_P13494 | 3.99 | T1 vs control | down | AT2G36690 | oxidoreductase, 2OG-Fe(II) oxygenase family protein [AT2G36690.1] |
| A_84_P140849 | 2.34 | T2 vs control | down | AT1G32920 | similar to unknown protein [*Arabidopsis thaliana*] (TAIR: AT1G32928.1) [AT1G32920.1] |
| A_84_P140849 | 2.35 | T1 vs control | down | AT1G32920 | similar to unknown protein [*Arabidopsis thaliana*] (TAIR: AT1G32928.1) [AT1G32920.1] |
| A_84_P14274 | 3.74 | T2 vs control | down | AT1G52690 | late embryogenesis abundant protein, putative/LEA protein, putative [AT1G52690.1] |
| A_84_P14274 | 4.95 | T1 vs control | down | AT1G52690 | late embryogenesis abundant protein, putative/LEA protein, putative [AT1G52690.1] |
| A_84_P14480 | 2.90 | T1 vs control | down | AT2G38250 | DNA-binding protein-related [AT2G38250.1] |
| A_84_P14480 | 3.08 | T2 vs control | down | AT2G38250 | DNA-binding protein-related [AT2G38250.1] |
| A_84_P14505 | 3.16 | T2 vs control | down | AT2G32140 | transmembrane receptor [AT2G32140.1] |
| A_84_P14505 | 3.42 | T1 vs control | down | AT2G32140 | transmembrane receptor [AT2G32140.1] |
| A_84_P148418 | 2.00 | T2 vs control | down | MT1C | MT1C (metallothionein 1C) [AT1G07610.1] |
| A_84_P148418 | 2.60 | T1 vs control | down | MT1C | MT1C (metallothionein 1C) [AT1G07610.1] |
| A_84_P14985 | 1.68 | T2 vs control | down | ATERF-2/ATERF2/ERF2 | ATERF-2/ATERF2/ERF2 (ETHYLENE RESPONSE FACTOR 2); DNA binding/ transcription activator/transcription factor [AT5G47220.1] |
| A_84_P14985 | 1.70 | T1 vs control | down | ATERF-2/ATERF2/ERF2 | ATERF-2/ATERF2/ERF2 (ETHYLENE RESPONSE FACTOR 2); DNA binding/ transcription activator/transcription factor [AT5G47220.1] |
| A_84_P15329 | 1.63 | T2 vs control | down | AT2G40000 | similar to unknown protein [*Arabidopsis thaliana*] (TAIR: AT3G55840.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] |
| A_84_P15329 | 1.96 | T1 vs control | down | AT2G40000 | similar to unknown protein [*Arabidopsis thaliana*] (TAIR: AT3G55840.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT2G40000.1] |
| A_84_P15331 | 1.69 | T1 vs control | down | AT2G43620 | chitinase, putative [AT2G43620.1] |
| A_84_P15331 | 2.09 | T2 vs control | down | AT2G43620 | chitinase, putative [AT2G43620.1] |
| A_84_P156125 | 2.95 | T2 vs control | down | BAP1 | BAP1 (BON ASSOCIATION PROTEIN 1) [AT3G61190.1] |
| A_84_P156125 | 3.78 | T1 vs control | down | BAP1 | BAP1 (BON ASSOCIATION PROTEIN 1) [AT3G61190.1] |
| A_84_P158205 | 2.65 | T1 vs control | down | AT1G22470 | similar to unknown protein [*Arabidopsis thaliana*] (TAIR: AT1G72240.1) [AT1G22470.1] |
| A_84_P158205 | 2.76 | T2 vs control | down | AT1G22470 | similar to unknown protein [*Arabidopsis thaliana*] (TAIR: AT1G72240.1) [AT1G22470.1] |
| A_84_P16568 | 2.40 | T2 vs control | down | AT3G55840 | similar to unknown protein [*Arabidopsis thaliana*] (TAIR: AT2G40000.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT3G55840.1] |

TABLE 8-continued

List of Genes Responsive to T1 and T2

| ProbeName | Fold change | Comparison | Regulation | Gene Symbol | Description |
|---|---|---|---|---|---|
| A_84_P16568 | 2.58 | T1 vs control | down | AT3G55840 | similar to unknown protein [*Arabidopsis thaliana*] (TAIR: AT2G40000.1); similar to unnamed protein product [*Vitis vinifera*] (GB: CAO41329.1); contains InterPro domain Hs1pro-1, C-terminal (InterPro: IPR009743); contains InterPro domain Hs1pro-1, N-terminal (InterPro: IPR009869) [AT3G55840.1] |
| A_84_P16848 | 1.58 | T1 vs control | down | AT5G39580 | peroxidase, putative [AT5G39580.1] |
| A_84_P16848 | 1.83 | T2 vs control | down | AT5G39580 | peroxidase, putative [AT5G39580.1] |
| A_84_P168493 | 1.54 | T2 vs control | down | AT3G46620 | zinc finger (C3HC4-type RING finger) family protein [AT3G46620.1] |
| A_84_P168493 | 1.72 | T1 vs control | down | AT3G46620 | zinc finger (C3HC4-type RING finger) family protein [AT3G46620.1] |
| A_84_P16923 | 2.53 | T2 vs control | down | RHL41 | RHL41 (RESPONSIVE TO HIGH LIGHT 41); nucleic acid binding/transcription factor/zinc ion binding [AT5G59820.1] |
| A_84_P16923 | 3.06 | T1 vs control | down | RHL41 | RHL41 (RESPONSIVE TO HIGH LIGHT 41); nucleic acid binding/transcription factor/zinc ion binding [AT5G59820.1] |
| A_84_P17111 | 1.54 | T1 vs control | down | AT1G02820 | late embryogenesis abundant 3 family protein/LEA3 family protein [AT1G02820.1] |
| A_84_P17111 | 1.95 | T2 vs control | down | AT1G02820 | late embryogenesis abundant 3 family protein/LEA3 family protein [AT1G02820.1] |
| A_84_P172941 | 1.59 | T1 vs control | down | AT2G18690 | similar to unknown protein [*Arabidopsis thaliana*] (TAIR: AT2G18680.1); similar to hypothetical protein OsI_029427 [*Oryza sativa* (*indica* cultivar-group)] (GB: EAZ08195.1) [AT2G18690.1] |
| A_84_P172941 | 1.88 | T2 vs control | down | AT2G18690 | similar to unknown protein [*Arabidopsis thaliana*] (TAIR: AT2G18680.1); similar to hypothetical protein OsI_029427 [*Oryza sativa* (*indica* cultivar-group)] (GB: EAZ08195.1) [AT2G18690.1] |
| A_84_P17328 | 3.18 | T2 vs control | down | AT2G39350 | ABC transporter family protein [AT2G39350.1] |
| A_84_P17328 | 3.38 | T1 vs control | down | AT2G39350 | ABC transporter family protein [AT2G39350.1] |
| A_84_P17343 | 2.23 | T2 vs control | down | ATERF13/EREBP | ATERF13/EREBP (ETHYLENE-RESPONSIVE ELEMENT BINDING FACTOR 13); DNA binding/transcription factor [AT2G44840.1] |
| A_84_P17343 | 4.33 | T1 vs control | down | ATERF13/EREBP | ATERF13/EREBP (ETHYLENE-RESPONSIVE ELEMENT BINDING FACTOR 13); DNA binding/transcription factor [AT2G44840.1] |
| A_84_P17614 | 2.98 | T2 vs control | down | CRK13/HIG1 | CRK13/HIG1; kinase [AT4G23210.1] |
| A_84_P17614 | 3.03 | T1 vs control | down | CRK13/HIG1 | CRK13/HIG1; kinase [AT4G23210.1] |
| A_84_P17802 | 1.62 | T2 vs control | down | ATCHX18 | ATCHX18 (cation/hydrogen exchanger 18); monovalent cation:proton antiporter [AT5G41610.1] |
| A_84_P17802 | 1.84 | T1 vs control | down | ATCHX18 | ATCHX18 (cation/hydrogen exchanger 18); monovalent cation:proton antiporter [AT5G41610.1] |
| A_84_P18553 | 1.59 | T2 vs control | down | B120 | B120; protein kinase/sugar binding [AT4G21390.1] |
| A_84_P18553 | 1.89 | T1 vs control | down | B120 | B120; protein kinase/sugar binding [AT4G21390.1] |
| A_84_P18557 | 3.14 | T1 vs control | down | AT4G22470 | protease inhibitor/seed storage/lipid transfer protein (LTP) family protein [AT4G22470.1] |
| A_84_P18557 | 3.46 | T2 vs control | down | AT4G22470 | protease inhibitor/seed storage/lipid transfer protein (LTP) family protein [AT4G22470.1] |
| A_84_P18566 | 1.82 | T2 vs control | down | AT4G24570 | mitochondrial substrate carrier family protein [AT4G24570.1] |
| A_84_P18566 | 2.20 | T1 vs control | down | AT4G24570 | mitochondrial substrate carrier family protein [AT4G24570.1] |
| A_84_P18823 | 1.58 | T1 vs control | down | AT5G61560 | protein kinase family protein [AT5G61560.1] |
| A_84_P18823 | 1.97 | T2 vs control | down | AT5G61560 | protein kinase family protein [AT5G61560.1] |

TABLE 8-continued

List of Genes Responsive to T1 and T2

| ProbeName | Fold change | Comparison | Regulation | Gene Symbol | Description |
|---|---|---|---|---|---|
| A_84_P18989 | 2.71 | T2 vs control | down | ATMC8 | ATMC8 (METACASPASE 8); caspase [AT1G16420.1] |
| A_84_P18989 | 3.12 | T1 vs control | down | ATMC8 | ATMC8 (METACASPASE 8); caspase [AT1G16420.1] |
| A_84_P19028 | 4.36 | T2 vs control | down | ORA47 | ORA47; DNA binding/transcription factor [AT1G74930.1] |
| A_84_P19028 | 6.17 | T1 vs control | down | ORA47 | ORA47; DNA binding/transcription factor [AT1G74930.1] |
| A_84_P19193 | 1.57 | T1 vs control | down | AT2G37980 | similar to unknown protein [*Arabidopsis thaliana*] (TAIR: AT5G01100.1); similar to unknown protein [*Arabidopsis thaliana*] (TAIR: AT3G54100.1); similar to unnamed protein product [*Vitis vinifera*] (GB: CAO15763.1); similar to hypothetical protein [*Vitis vinifera*] (GB: CAN72579.1); contains InterPro domain Protein of unknown function DUF246, plant (InterPro: IPR004348) [AT2G37980.1] |
| A_84_P19193 | 1.85 | T2 vs control | down | AT2G37980 | similar to unknown protein [*Arabidopsis thaliana*] (TAIR: AT5G01100.1); similar to unknown protein [*Arabidopsis thaliana*] (TAIR: AT3G54100.1); similar to unnamed protein product [*Vitis vinifera*] (GB: CAO15763.1); similar to hypothetical protein [*Vitis vinifera*] (GB: CAN72579.1); contains InterPro domain Protein of unknown function DUF246, plant (InterPro: IPR004348) [AT2G37980.1] |
| A_84_P20728 | 1.63 | T2 vs control | down | ABR1 | ABR1 (ABA REPRESSOR1); DNA binding/transcription factor [AT5G64750.1] |
| A_84_P20728 | 1.67 | T1 vs control | down | ABR1 | ABR1 (ABA REPRESSOR1); DNA binding/transcription factor [AT5G64750.1] |
| A_84_P209868 | 2.94 | T2 vs control | down | AT2G32130 | similar to UNE1 (unfertilized embryo sac 1) [*Arabidopsis thaliana*] (TAIR: AT1G29300.1); similar to unnamed protein product [*Vitis vinifera*] (GB: CAO48018.1); contains InterPro domain Protein of unknown function DUF641, plant (InterPro: IPR006943) [AT2G32130.1] |
| A_84_P209868 | 3.01 | T1 vs control | down | AT2G32130 | similar to UNE1 (unfertilized embryo sac 1) [*Arabidopsis thaliana*] (TAIR: AT1G29300.1); similar to unnamed protein product [*Vitis vinifera*] (GB: CAO48018.1); contains InterPro domain Protein of unknown function DUF641, plant (InterPro: IPR006943) [AT2G32130.1] |
| A_84_P20998 | 3.18 | T1 vs control | down | PHI-1 | PHI-1 (PHOSPHATE-INDUCED 1) [AT1G35140.1] |
| A_84_P20998 | 5.03 | T2 vs control | down | PHI-1 | PHI-1 (PHOSPHATE-INDUCED 1) [AT1G35140.1] |
| A_84_P21275 | 1.72 | T2 vs control | down | AT3G50930 | AAA-type ATPase family protein [AT3G50930.1] |
| A_84_P21275 | 2.51 | T1 vs control | down | AT3G50930 | AAA-type ATPase family protein [AT3G50930.1] |
| A_84_P217688 | 1.89 | T2 vs control | down | AT1G76600 | similar to unknown protein [*Arabidopsis thaliana*] (TAIR: AT1G21010.1); similar to hypothetical protein [*Vitis vinifera*] (GB: CAN67638.1) [AT1G76600.1] |
| A_84_217688 | 2.15 | T1 vs control | down | AT1G76600 | similar to unknown protein [*Arabidopsis thaliana*] (TAIR: AT1G21010.1); similar to hypothetical protein [*Vitis vinifera*] (GB: CAN67638.1) [AT1G76600.1] |
| A_84_P21874 | 2.02 | T2 vs control | down | STZ | STZ (SALT TOLERANCE ZINC FINGER); nucleic acid binding/transcription factor/zinc ion binding [AT1G27730.1] |
| A_84_P21874 | 2.69 | T1 vs control | down | STZ | STZ (SALT TOLERANCE ZINC FINGER); nucleic acid binding/transcription factor/zinc ion binding [AT1G27730.1] |

TABLE 8-continued

List of Genes Responsive to T1 and T2

| ProbeName | Fold change | Comparison | Regulation | Gene Symbol | Description |
|---|---|---|---|---|---|
| A_84_P21931 | 1.88 | T2 vs control | down | ATERF11/ERF11 | ATERF11/ERF11 (ERF domain protein 11); DNA binding/transcription factor/ transcription repressor [AT1G28370.1] |
| A_84_P21931 | 2.58 | T1 vs control | down | ATERF11/ERF11 | ATERF11/ERF11 (ERF domain protein 11); DNA binding/transcription factor/ transcription repressor [AT1G28370.1] |
| A_84_P21970 | 1.82 | T2 vs control | down | AT2G22200 | AP2 domain-containing transcription factor [AT2G22200.1] |
| A_84_P21970 | 2.55 | T1 vs control | down | AT2G22200 | AP2 domain-containing transcription factor [AT2G22200.1] |
| A_84_P22181 | 2.28 | T1 vs control | down | PMZ | PMZ; zinc ion binding [AT3G28210.1] |
| A_84_P22181 | 3.47 | T2 vs control | down | PMZ | PMZ; zinc ion binding [AT3G28210.1] |
| A_84_P22532 | 1.57 | T1 vs control | down | AT5G41740 | disease resistance protein (TIR-NBS-LRR class), putative [AT5G41740.1] |
| A_84_P22532 | 1.72 | T2 vs control | down | AT5G41740 | disease resistance protein (TIR-NBS-LRR class), putative [AT5G41740.1] |
| A_84_P22854 | 1.62 | T2 vs control | down | AT1G51790 | kinase [AT1G51790.1] |
| A_84_P22854 | 1.65 | T1 vs control | down | AT1G51790 | kinase [AT1G51790.1] |
| A_84_P228659 | 3.05 | T1 vs control | down | AT2G32190 | similar to unknown protein [*Arabidopsis thaliana*] (TAIR: AT2G32210.1); similar to unknown [*Populus trichocarpa*] (GB: ABK92801.1); contains domain PD188784 (PD188784) [AT2G32190.1] |
| A_84_P228659 | 3.07 | T2 vs control | down | AT2G32190 | similar to unknown protein [*Arabidopsis thaliana*] (TAIR: AT2G32210.1); similar to unknown [*Populus trichocarpa*] (GB: ABK92801.1); contains domain PD188784 (PD188784) [AT2G32190.1] |
| A_84_P22924 | 2.94 | T1 vs control | down | AT2G47550 | pectinesterase family protein [AT2G47550.1] |
| A_84_P22924 | 8.06 | T2 vs control | down | AT2G47550 | pectinesterase family protein [AT2G47550.1] |
| A_84_P229729 | 1.91 | T1 vs control | down | AT2G20142 | transmembrane receptor [AT2G20142.1] |
| A_84_P229729 | 2.03 | T2 vs control | down | AT2G20142 | transmembrane receptor [AT2G20142.1] |
| A_84_P232439 | 1.59 | T1 vs control | down | WRKY18 | WRKY18 (WRKY DNA-binding protein 18); transcription factor [AT4G31800.1] |
| A_84_P232439 | 1.70 | T2 vs control | down | WRKY18 | WRKY18 (WRKY DNA-binding protein 18); transcription factor [AT4G31800.1] |
| A_84_P23913 | 1.76 | T1 vs control | down | AT2G38870 | protease inhibitor, putative [AT2G38870.1] |
| A_84_P23913 | 1.82 | T2 vs control | down | AT2G38870 | protease inhibitor, putative [AT2G38870.1] |
| A_84_P23919 | 2.82 | T2 vs control | down | YLS9 | YLS9 (YELLOW-LEAF-SPECIFIC GENE 9) [AT2G35980.1] |
| A_84_P23919 | 3.56 | T1 vs control | down | YLS9 | YLS9 (YELLOW-LEAF-SPECIFIC GENE 9) [AT2G35980.1] |
| A_84_P242895 | 1.74 | T1 vs control | down | AT1G66160 | U-box domain-containing protein [AT1G66160.1] |
| A_84_P242895 | 2.10 | T2 vs control | down | AT1G66160 | U-box domain-containing protein [AT1G66160.1] |
| A_84_P262200 | 1.67 | T2 vs control | down | AT5G43420 | zinc finger (C3HC4-type RING finger) family protein [AT5G43420.1] |
| A_84_P262200 | 2.14 | T1 vs control | down | AT5G43420 | zinc finger (C3HC4-type RING finger) family protein [AT5G43420.1] |
| A_84_P269630 | 7.00 | T2 vs control | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] |
| A_84_P269630 | 7.23 | T1 vs control | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] |
| A_84_P286120 | 1.56 | T2 vs control | down | CYP707A1 | CYP707A1 (cytochrome P450, family 707, subfamily A, polypeptide 1); oxygen binding [AT4G19230.1] |
| A_84_P286120 | 2.12 | T1 vs control | down | CYP707A1 | CYP707A1 (cytochrome P450, family 707, subfamily A, polypeptide 1); oxygen binding [AT4G19230.1] |
| A_84_P288954 | 2.67 | T1 vs control | down | AT2G03020 | heat shock protein-related [AT2G03020.1] |

TABLE 8-continued

List of Genes Responsive to T1 and T2

| ProbeName | Fold change | Comparison | Regulation | Gene Symbol | Description |
|---|---|---|---|---|---|
| A_84_P288954 | 2.82 | T2 vs control | down | AT2G03020 | heat shock protein-related [AT2G03020.1] |
| A_84_P289964 | 1.61 | T1 vs control | down | AT1G19020 | similar to unknown protein [Arabidopsis thaliana] (TAIR: AT3G48180.1); similar to unnamed protein product [Vitis vinifera] (GB: CAO40966.1) [AT1G19020.1] |
| A_84_P289964 | 1.77 | T2 vs control | down | AT1G19020 | similar to unknown protein [Arabidopsis thaliana] (TAIR: AT3G48180.1); similar to unnamed protein product [Vitis vinifera] (GB: CAO40966.1) [AT1G19020.1] |
| A_84_P306860 | 1.63 | T1 vs control | down | AT5G10695 | similar to unknown protein [Arabidopsis thaliana] (TAIR: AT5G57123.1); similar to unknown [Picea sitchensis] (GB: ABK22689.1) [AT5G10695.1] |
| A_84_P306860 | 1.82 | T2 vs control | down | AT5G10695 | similar to unknown protein [Arabidopsis thaliana] (TAIR: AT5G57123.1); similar to unknown [Picea sitchensis] (GB: ABK22689.1) [AT5G10695.1] |
| A_84_P54170 | 1.55 | T2 vs control | down | AT3G57450 | similar to unnamed protein product [Vitis vinifera] (GB: CAO40798.1) [AT3G57450.1] |
| A_84_P54170 | 1.78 | T1 vs control | down | AT3G57450 | similar to unnamed protein product [Vitis vinifera] (GB: CAO40798.1) [AT3G57450.1] |
| A_84_P554567 | 1.90 | T1 vs control | down | GATL10 | GATL10 (Galacturonosyltransferase-like 10); polygalacturonate 4-alpha-galacturonosyltransferase/transferase, transferring hexosyl groups [AT3G28340.1] |
| A_84_P554567 | 2.13 | T2 vs control | down | GATL10 | GATL10 (Galacturonosyltransferase-like 10); polygalacturonate 4-alpha-galacturonosyltransferase/transferase, transferring hexosyl groups [AT3G28340.1] |
| A_84_P554830 | 1.58 | T2 vs control | up | AT5G20635 | receptor [AT5G20635.1] |
| A_84_P554830 | 1.80 | T1 vs control | up | AT5G20635 | receptor [AT5G20635.1] |
| A_84_P557122 | 3.65 | T2 vs control | down | AT2G45130 | SPX (SYG1/Pho81/XPR1) domain-containing protein [AT2G45130.1] |
| A_84_P557122 | 3.91 | T1 vs control | down | AT2G45130 | SPX (SYG1/Pho81/XPR1) domain-containing protein [AT2G45130.1] |
| A_84_P561097 | 1.59 | T2 vs control | down | AT5G46295 | unknown protein [AT5G46295.1] |
| A_84_P561097 | 2.08 | T1 vs control | down | AT5G46295 | unknown protein [AT5G46295.1] |
| A_84_P567134 | 1.72 | T1 vs control | down | AT4G27657 | similar to unknown protein [Arabidopsis thaliana] (TAIR: AT4G27652.1) [AT4G27657.1] |
| A_84_P567134 | 2.46 | T2 vs control | down | AT4G27657 | similar to unknown protein [Arabidopsis thaliana] (TAIR: AT4G27652.1) [AT4G27657.1] |
| A_84_P573393 | 4.07 | T1 vs control | down | AT4G27654 | unknown protein [AT4G27654.1] |
| A_84_P573393 | 5.33 | T2 vs control | down | AT4G27654 | unknown protein [AT4G27654.1] |
| A_84_P579612 | 1.84 | T1 vs control | down | AT4G27652 | similar to unknown protein [Arabidopsis thaliana] (TAIR: AT4G27657.1) [AT4G27652.1] |
| A_84_P579612 | 2.21 | T2 vs control | down | AT4G27652 | similar to unknown protein [Arabidopsis thaliana] (TAIR: AT4G27657.1) [AT4G27652.1] |
| A_84_P582920 | 2.88 | T1 vs control | down | BAP2 | BAP2 (BON ASSOCIATION PROTEIN 2) [AT2G45760.1] |
| A_84_P582920 | 3.01 | T2 vs control | down | BAP2 | BAP2 (BON ASSOCIATION PROTEIN 2) [AT2G45760.1] |
| A_84_P586644 | 2.17 | T2 vs control | down | DVL20/RTFL1 | DVL20/RTFL1 (ROTUNDIFOLIA 1) [AT3G53232.1] |
| A_84_P586644 | 2.37 | T1 vs control | down | DVL20/RTFL1 | DVL20/RTFL1 (ROTUNDIFOLIA 1) [AT3G53232.1] |
| A_84_P592444 | 2.07 | T1 vs control | down | AT1G19200 | senescence-associated protein-related [AT1G19200.1] |
| A_84_P592444 | 2.57 | T2 vs control | down | AT1G19200 | senescence-associated protein-related [AT1G19200.1] |
| A_84_P595805 | 1.79 | T2 vs control | down | AT5G36925 | similar to unknown protein [Arabidopsis thaliana] (TAIR: AT5G36920.1) [AT5G36925.1] |
| A_84_P595805 | 1.93 | T1 vs control | down | AT5G36925 | similar to unknown protein [Arabidopsis thaliana] (TAIR: AT5G36920.1) [AT5G36925.1] |

TABLE 8-continued

List of Genes Responsive to T1 and T2

| ProbeName | Fold change | Comparison | Regulation | Gene Symbol | Description |
|---|---|---|---|---|---|
| A_84_P68014 | 1.56 | T1 vs control | down | AT4G34150 | C2 domain-containing protein [AT4G34150.1] |
| A_84_P68014 | 1.64 | T2 vs control | down | AT4G34150 | C2 domain-containing protein [AT4G34150.1] |
| A_84_P715787 | 1.55 | T1 vs control | down | AT1G32928 | similar to unknown protein [Arabidopsis thaliana] (TAIR: AT1G32920.1) [AT1G32928.1] |
| A_84_P715787 | 1.96 | T2 vs control | down | AT1G32928 | similar to unknown protein [Arabidopsis thaliana] (TAIR: AT1G32920.1) [AT1G32928.1] |
| A_84_P762507 | 3.37 | T2 vs control | down | AT3G25573 | unknown protein [AT3G25573.1] |
| A_84_P762507 | 5.62 | T1 vs control | down | AT3G25573 | unknown protein [AT3G25573.1] |
| A_84_P763881 | 1.53 | T2 vs control | down | AT4G20830 | FAD-binding domain-containing protein [AT4G20830.1] |
| A_84_P763881 | 1.58 | T1 vs control | down | AT4G20830 | FAD-binding domain-containing protein [AT4G20830.1] |
| A_84_P786098 | 2.38 | T1 vs control | down | AT1G32920 | 07-E012992-019-004-M01-SP6r MPIZ-ADIS-019 Arabidopsis thaliana cDNA clone MPIZp768M014Q 3-PRIME, mRNA sequence [CB253198] |
| A_84_P786098 | 4.06 | T2 vs control | down | AT1G32920 | 07-E012992-019-004-M01-SP6r MPIZ-ADIS-019 Arabidopsis thaliana cDNA clone MPIZp768M014Q 3-PRIME, mRNA sequence [CB253198] |
| A_84_P786490 | 1.55 | T2 vs control | down | WRKY46 | WRKY46 (WRKY DNA-binding protein 46); transcription factor [AT2G46400.1] |
| A_84_P786490 | 2.35 | T1 vs control | down | WRKY46 | WRKY46 (WRKY DNA-binding protein 46); transcription factor [AT2G46400.1] |
| A_84_P791120 | 4.10 | T2 vs control | down | AT3G25240 | similar to unknown protein [Arabidopsis thaliana] (TAIR: AT3G07350.1); similar to unnamed protein product [Vitis vinifera] (GB: CAO39951.1); contains InterPro domain Protein of unknown function DUF506, plant (InterPro: IPR006502) [AT3G25240.1] |
| A_84_P791120 | 6.24 | T1 vs control | down | AT3G25240 | similar to unknown protein [Arabidopsis thaliana] (TAIR: AT3G07350.1); similar to unnamed protein product [Vitis vinifera] (GB: CAO39951.1); contains InterPro domain Protein of unknown function DUF506, plant (InterPro: IPR006502) [AT3G25240.1] |
| A_84_P797066 | 2.02 | T2 vs control | down | | AYAFD87TR pooled cDNA populations Arabidopsis thaliana cDNA, mRNA sequence [EG438208] |
| A_84_P797066 | 2.40 | T1 vs control | down | | AYAFD87TR pooled cDNA populations Arabidopsis thaliana cDNA, mRNA sequence [EG438208] |
| A_84_P816512 | 1.65 | T1 vs control | down | AT2G18690 | similar to unknown protein [Arabidopsis thaliana] (TAIR: AT2G18680.1); similar to hypothetical protein OsI_029427 [Oryza sativa (indica cultivar-group)] (GB: EAZ08195.1) [AT2G18690.1] |
| A_84_P816512 | 1.94 | T2 vs control | down | AT2G18690 | similar to unknown protein [Arabidopsis thaliana] (TAIR: AT2G18680.1); similar to hypothetical protein OsI_029427 [Oryza sativa (indica cultivar-group)] (GB: EAZ08195.1) [AT2G18690.1] |
| A_84_P818437 | 4.67 | T2 vs control | down | CML37/CML39 | CML37/CML39; calcium ion binding [AT5G42380.1] |
| A_84_P818437 | 4.95 | T1 vs control | down | CML37/CML39 | CML37/CML39; calcium ion binding [AT5G42380.1] |
| A_84_P819307 | 1.76 | T2 vs control | up | AT2G43590 | chitinase, putative [AT2G43590.1] |
| A_84_P819307 | 1.84 | T1 vs control | down | AT2G43590 | chitinase, putative [AT2G43590.1] |
| A_84_P819549 | 1.87 | T2 vs control | down | AT5G41740 | disease resistance protein (TIR-NBS-LRR class), putative [AT5G41740.1] |
| A_84_P819549 | 2.45 | T1 vs control | down | AT5G41740 | disease resistance protein (TIR-NBS-LRR class), putative [AT5G41740.1] |
| A_84_P823733 | 1.73 | T1 vs control | down | GATL10 | GATL10 (Galacturonosyltransferase-like 10); polygalacturonate 4-alpha-galacturonosyltransferase/transferase, transferring hexosyl groups [AT3G28340.1] |
| A_84_P823733 | 1.76 | T2 vs control | down | GATL10 | GATL10 (Galacturonosyltransferase-like 10); polygalacturonate 4-alpha- |

TABLE 8-continued

List of Genes Responsive to T1 and T2

| ProbeName | Fold change | Comparison | Regulation | Gene Symbol | Description |
|---|---|---|---|---|---|
| A_84_P82909 | 1.79 | T2 vs control | down | AT1G17830 | galacturonosyltransferase/transferase, transferring hexosyl groups [AT3G28340.1] similar to unknown protein [*Arabidopsis thaliana*] (TAIR: AT1G73210.1); similar to unnamed protein product [*Vitis vinifera*] (GB: CAO45300.1); contains InterPro domain Protein of unknown function DUF789 (InterPro: IPR008507) [AT1G17830.1] |
| A_84_P82909 | 2.01 | T1 vs control | down | AT1G17830 | similar to unknown protein [*Arabidopsis thaliana*] (TAIR: AT1G73210.1); similar to unnamed protein product [*Vitis vinifera*] (GB: CAO45300.1); contains InterPro domain Protein of unknown function DUF789 (InterPro: IPR008507) [AT1G17830.1] |
| A_84_P839984 | 1.62 | T1 vs control | down | AT1G63580 | protein kinase-related [AT1G63580.1] |
| A_84_P839984 | 1.87 | T2 vs control | down | AT1G63580 | protein kinase-related [AT1G63580.1] |
| A_84_P844006 | 3.39 | T1 vs control | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] |
| A_84_P844006 | 5.18 | T2 vs control | down | AT2G27505 | similar to F-box family protein [*Arabidopsis thaliana*] (TAIR: AT5G44950.1); contains InterPro domain FBD (InterPro: IPR013596); contains InterPro domain FBD-like (InterPro: IPR006566) [AT2G27505.1] |
| A_84_P849049 | 2.30 | T1 vs control | down | | NM_113740 PMZ {*Arabidopsis thaliana*} (exp = −1; wgp = 0; cg = 0), partial (76%) [TC302412] |
| A_84_P849049 | 3.70 | T2 vs control | down | | NM_113740 PMZ {*Arabidopsis thaliana*} (exp = −1; wgp = 0; cg = 0), partial (76%) [TC302412] |
| A_84_P862479 | 4.27 | T2 vs control | down | | |
| A_84_P862479 | 4.52 | T1 vs control | down | | |
| A_84_P97916 | 3.01 | T2 vs control | down | AT4G29780 | similar to unknown protein [*Arabidopsis thaliana*] (TAIR: AT5G12010.1); similar to unnamed protein product [*Vitis vinifera*] (GB: CAO43835.1); contains domain PTHR22930 (PTHR22930) [AT4G29780.1] |
| A_84_P97916 | 3.84 | T1 vs control | down | AT4G29780 | similar to unknown protein [*Arabidopsis thaliana*] (TAIR: AT5G12010.1); similar to unnamed protein product [*Vitis vinifera*] (GB: CAO43835.1); contains domain PTHR22930 (PTHR22930) [AT4G29780.1] |

TABLE 9

List of 11 Transcription Factor Genes Responsive to T1 and T2

| ProbeName | Fold chang | Response to | Comparison | Regulation | Gene Symbol | Description |
|---|---|---|---|---|---|---|
| A_84_P13104 | 2.63 | T1 & T2 | T2 vs control | down | WRKY48 | WRKY48 (WRKY DNA-binding protein 48); transcription factor [AT5G49520.1] |
| A_84_P13104 | 2.79 | T1 & T2 | T1 vs control | down | WRKY48 | WRKY48 (WRKY DNA-binding protein 48); transcription factor [AT5G49520.1] |
| A_84_P14985 | 1.68 | T1 & T2 | T2 vs control | down | ATERF-2/ATERF2/ERF2 | ATERF-2/ATERF2/ERF2 (ETHYLENE RESPONSE FACTOR 2); DNA binding/transcription activator/ transcription factor [AT5G47220.1] |
| A_84_P14985 | 1.70 | T1 & T2 | T1 vs control | down | ATERF-2/ATERF2/ERF2 | ATERF-2/ATERF2/ERF2 (ETHYLENE RESPONSE FACTOR 2); DNA binding/transcription activator/ transcription factor [AT5G47220.1] |
| A_84_P16923 | 2.53 | T1 & T2 | T2 vs control | down | RHL41 | RHL41 (RESPONSIVE TO HIGH LIGHT 41); nucleic acid binding/transcription factor/zinc ion binding [AT5G59820.1] |

TABLE 9-continued

List of 11 Transcription Factor Genes Responsive to T1 and T2

| ProbeName | Fold chang | Response to | Comparison | Regulation | Gene Symbol | Description |
|---|---|---|---|---|---|---|
| A_84_P16923 | 3.06 | T1 & T2 | T1 vs control | down | RHL41 | RHL41 (RESPONSIVE TO HIGH LIGHT 41); nucleic acid binding/transcription factor/zinc ion binding [AT5G59820.1] |
| A_84_P17343 | 2.23 | T1 & T2 | T2 vs control | down | ATERF13/EREBP | ATERF13/EREBP (ETHYLENE-RESPONSIVE ELEMENT BINDING FACTOR 13); DNA binding/transcription factor [AT2G44840.1] |
| A_84_P17343 | 4.33 | T1 & T2 | T1 vs control | down | ATERF13/EREBP | ATERF13/EREBP (ETHYLENE-RESPONSIVE ELEMENT BINDING FACTOR 13); DNA binding/transcription factor [AT2G44840.1] |
| A_84_P19028 | 4.36 | T1 & T2 | T2 vs control | down | ORA47 | ORA47; DNA binding/transcription factor [AT1G74930.1] |
| A_84_P19028 | 6.17 | T1 & T2 | T1 vs control | down | ORA47 | ORA47; DNA binding/transcription factor [AT1G74930.1] |
| A_84_P20728 | 1.63 | T1 & T2 | T2 vs control | down | ABR1 | ABR1 (ABA REPRESSOR1); DNA binding/transcription factor [AT5G64750.1] |
| A_84_P20728 | 1.67 | T1 & T2 | T1 vs control | down | ABR1 | ABR1 (ABA REPRESSOR1); DNA binding/transcription factor [AT5G64750.1] |
| A_84_P21874 | 2.02 | T1 & T2 | T2 vs control | down | STZ | STZ (SALT TOLERANCE ZINC FINGER); nucleic acid binding/transcription factor/zinc ion binding [AT1G27730.1] |
| A_84_P21874 | 2.69 | T1 & T2 | T1 vs control | down | STZ | STZ (SALT TOLERANCE ZINC FINGER); nucleic acid binding/transcription factor/zinc ion binding [AT1G27730.1] |
| A_84_P21931 | 1.88 | T1 & T2 | T2 vs control | down | ATERF11/ERF11 | ATERF11/ERF11 (ERF domain protein 11); DNA binding/transcription factor/transcription repressor [AT1G28370.1] |
| A_84_P21931 | 2.58 | T1 & T2 | T1 vs control | down | ATERF11/ERF11 | ATERF11/ERF11 (ERF domain protein 11); DNA binding/transcription factor/transcription repressor [AT1G28370.1] |
| A_84_P21970 | 1.82 | T1 & T2 | T2 vs control | down | AT2G22200 | AP2 domain-containing transcription factor [AT2G22200.1] |
| A_84_P21970 | 2.55 | T1 & T2 | T1 vs control | down | AT2G22200 | AP2 domain-containing transcription factor [AT2G22200.1] |
| A_84_P232439 | 1.59 | T1 & T2 | T1 vs control | down | WRKY18 | WRKY18 (WRKY DNA-binding protein 18); transcription factor [AT4G31800.1] |
| A_84_P232439 | 1.70 | T1 & T2 | T2 vs control | down | WRKY18 | WRKY18 (WRKY DNA-binding protein 18); transcription factor [AT4G31800.1] |
| A_84_P786490 | 1.55 | T1 & T2 | T2 vs control | down | WRKY46 | WRKY46 (WRKY DNA-binding protein 46); transcription factor [AT2G46400.1] |
| A_84_P786490 | 2.35 | T1 & T2 | T1 vs control | down | WRKY46 | WRKY46 (WRKY DNA-binding protein 46); transcription factor [AT2G46400.1] |

The invention claimed is:

1. A method of improving abiotic stress-response in a plant, the method comprising contacting a part of a seed, a plant, or a locus thereof with a composition of matter at a rate of about 0.01 gram/hectare to about 10.0 gram/hectare dry weight, the composition of matter comprising two or more of:
   a. a mixture of condensed hydrocarbons, lignins, and tannins and/or condensed tannins;
   b. an oxygen-to-carbon ratio for the composition of matter of greater than about 0.5;
   c. a total number of tannin compounds greater than about 200, the tannin compounds having a hydrogen to carbon ratio of about 0.5 to about 1.4, and an aromaticity index of less than about 0.7 as measured by mass spectroscopy; or
   d. a mass distribution of about 55-60% lignin compounds, 27-35% tannin compounds, and about 8-15% condensed hydrocarbon as measured by mass spectroscopy and improving the abiotic stress response of a plant exposed to an abiotic stress.

2. The method of claim 1, wherein said composition of matter up regulates a cell surface receptor of the plant.

3. The method of claim 1, wherein the composition of matter down regulates at least one plant gene selected from WRKY element, an ethylene-responsive element, ABA repressor, salt tolerance zinc finger motif, high light responsive element, a putative disease resistance gene, putative chitinase protein, calcium ion binding proteins, zinc ion binding proteins, phosphate induced protein, ABC transporter family protein, cation/hydrogen exchanger, glycolipid transporter gene, calmodulin-related protein, protein kinase/sugar binding, protease inhibitor genes, pectinesterase family protein, oxidoreductase, transmembrane receptor gene, heat-shock protein gene, or senescence associated protein.

4. The method of claim 1, wherein said composition of matter up regulates at least one plant gene selected from plant regulator production or responses, auxin-responsive family proteins, gibberellin 20 oxidase genes, encoding amino acid transporters, carbohydrate transporters, purine transporters, genes encoding enzyme, defense-related genes, genes encoding transcription factor or transcription regulators, or genes encoding ATPase/ion movement.

5. The method of claim 1, wherein said composition of matter up regulates at least one plant gene selected from genes encoding transcription factors, genes encoding enzymes, protein kinases or hydrolases.

6. The method of claim 1, wherein said composition of matter up regulates at least one plant gene selected from plant regulator production or responses, auxin-responsive family proteins, gibberellin 20 oxidase genes, encoding amino acid transporters, carbohydrate transporters, purine transporters, genes encoding enzyme, defense-related genes, genes encoding transcription factor or transcription regulators, or genes encoding ATPase/ion movement; and down regulates at least one plant gene selected from transcription factors, transcription regulators, growth, defense, metabolism, or ion transport.

7. The method of claim 1, wherein the composition of matter comprises a mixture of condensed hydrocarbons, lignins, and tannins and/or condensed tannins, wherein at least 10% of the total % of compounds of the composition are tannins and/or condensed tannins.

8. The method of claim 1, wherein the composition of matter comprises a mixture of condensed hydrocarbons, lignins, and tannins and/or condensed tannins, wherein at least 20% of the total % of compounds of the composition are tannins and/or condensed tannins.

9. The method of claim 1, wherein the improvement in stress response comprises improved agronomical recovery of the plant after said stress is reduced or discontinued as compared to a similar plant species not treated with said composition of matter.

10. The method of claim 1, wherein the stress is drought.

11. The method of claim 1, wherein the stress is exposure to saline water.

12. A method of regulating at least one gene of a plant species, the method comprising
   contacting a part of a plant or a locus thereof with a composition of matter at a rate of about 0.01 gram/hectare to about 10.0 gram/hectare dry weight, the composition of matter comprising two or more of:
   a. a mixture of condensed hydrocarbons, lignins, and tannins and/or condensed tannins;
   b. an oxygen-to-carbon ratio for the composition of matter of greater than about 0.5;
   c. a total number of tannin compounds greater than about 200, the tannin compounds having a hydrogen to carbon ratio of about 0.5 to about 1.4, and an aromaticity index of less than about 0.7 as measured by mass spectroscopy; or
   d. a mass distribution of about 55-60% lignin compounds, 27-35% tannin compounds, and about 8-15% condensed hydrocarbon as measured by mass spectroscopy;
   wherein the at least one gene regulates plant function associated with growth, defense, metabolism, or ion transport.

13. The method of claim 12, wherein the at least one gene regulates at least one plant gene selected from genes encoding transcription factors, genes encoding enzymes, protein kinases or hydrolases.

14. The method of claim 12, wherein the composition of matter comprises a mixture of condensed hydrocarbons, lignins, and tannins and/or condensed tannins, wherein at least 10% of the total % of compounds of the composition are tannins and/or condensed tannins.

15. The method of claim 12, wherein the composition of matter comprises a mixture of condensed hydrocarbons, lignins, and tannins and/or condensed tannins, wherein at least 20% of the total % of compounds of the composition are tannins and/or condensed tannins.

16. The method of claim 12, wherein the at least one gene regulated provides improved agronomical recovery of the plant after an environmental stress is reduced or discontinued as compared to a similar plant species not treated with said composition of matter.

17. The method of claim 16, wherein the environmental stress is drought.

18. The method of claim 16, wherein the environmental stress is exposure to saline water.

19. The method of claim 2, wherein said composition of matter up regulates a cell surface receptor of the plant and down regulates another cell surface receptor of the plant.

20. The method of claim 13, wherein said composition of matter up regulates at least one plant gene selected from plant regulator production or responses, auxin-responsive family proteins, gibberellin 20 oxidase genes, encoding amino acid transporters, carbohydrate transporters, purine transporters, genes encoding enzyme, defense-related genes, genes encoding transcription factor or transcription regulators, or genes encoding ATPase/ion movement; or down regulates at least one plant gene selected from transcription factors, transcription regulators, growth, defense, metabolism, or ion transport.

21. A method of improving abiotic stress-response in a plant, the method comprising contacting a foliar surface of a plant with a composition of matter at a rate of about 0.01 gram/hectare to about 10.0 gram/hectare dry weight, the composition of matter comprising two or more of:
   a. a mixture of condensed hydrocarbons, lignins, tannins and/or condensed tannins;
   b. an oxygen-to-carbon-ratio for the composition of matter of greater than about 0.5;
   c. a total number of tannin compounds greater than about 200, the tannin compounds having a hydrogen to carbon ratio of about 0.5 to about 1.4, and an aromaticity index of less than about 0.7 as measured by mass spectroscopy; or
   d. a mass distribution of about 55-60% lignin compounds, 27-35% tannin compounds, and about 8-15% condensed hydrocarbon as measured by mass spectroscopy and
   improving the abiotic stress response of a plant exposed to an abiotic stress.

* * * * *